US006809809B2

(12) United States Patent
Kinney et al.

(10) Patent No.: US 6,809,809 B2
(45) Date of Patent: Oct. 26, 2004

(54) OPTICAL METHOD AND APPARATUS FOR INSPECTING LARGE AREA PLANAR OBJECTS

(75) Inventors: Patrick D. Kinney, Hayward, CA (US); Anand Gupta, Phoenix, AZ (US); Nagaraja P. Rao, San Carlos, CA (US)

(73) Assignee: Real Time Metrology, Inc., Castro Valley, CA (US)

( * ) Notice: Subject to any disclaimer, the term of this patent is extended or adjusted under 35 U.S.C. 154(b) by 0 days.

(21) Appl. No.: 10/379,016

(22) Filed: Mar. 4, 2003

(65) Prior Publication Data

US 2004/0012775 A1 Jan. 22, 2004

Related U.S. Application Data

(63) Continuation-in-part of application No. 09/994,021, filed on Nov. 14, 2001, now Pat. No. 6,630,996.
(60) Provisional application No. 60/361,799, filed on Mar. 5, 2002, provisional application No. 60/297,660, filed on Jun. 12, 2001, and provisional application No. 60/249,000, filed on Nov. 15, 2000.

(51) Int. Cl.[7] .............................................. G01N 21/00
(52) U.S. Cl. ............................. 356/237.5; 356/237.1; 356/237.4
(58) Field of Search ........................ 356/237.1–237.6, 356/600–601, 609, 614; 250/201.1, 201.2, 201.3, 201.4, 250, 559.28, 559.31

(56) References Cited

U.S. PATENT DOCUMENTS

| | | | |
|---|---|---|---|
| 3,790,287 A | 2/1974 | Cuthbert et al. | 356/120 |
| 4,342,515 A | 8/1982 | Akiba et al. | 356/237 |
| 4,373,805 A | 2/1983 | Mallinson | 356/1 |
| 4,377,340 A | 3/1983 | Green et al. | 356/237 |
| 4,378,159 A | 3/1983 | Galbraith | 356/237 |
| 4,482,424 A | 11/1984 | Katzir et al. | 156/626 |
| 4,569,695 A | 2/1986 | Yamashita et al. | 134/1 |
| 4,614,427 A | 9/1986 | Koizumi et al. | 356/237 |
| 4,655,592 A | 4/1987 | Allemand | 356/237 |
| 4,692,223 A | 9/1987 | Lampert et al. | 204/34.5 |
| 4,716,299 A | * 12/1987 | Tanaka et al. | 250/559.01 |
| 4,764,969 A | * 8/1988 | Ohtombe et al. | 382/148 |
| 4,772,126 A | 9/1988 | Allemand et al. | 356/336 |
| 4,827,143 A | 5/1989 | Munakata et al. | 250/574 |
| 4,895,446 A | 1/1990 | Maldari et al. | 356/336 |

(List continued on next page.)

OTHER PUBLICATIONS

W.P. Shaw and R.P. Sopher. "High Speed Automatic Particle Counter", IBM Technical Disclosure Bulletin, vol. 17, No. 9, Feb. 1975.

(List continued on next page.)

*Primary Examiner*—Frank G. Font
*Assistant Examiner*—Sang H. Nguyen
(74) *Attorney, Agent, or Firm*—Westman, Champlin & Kelly

(57) ABSTRACT

An optical inspection module is provided for detecting defects on a substrate having first and second opposite planar surfaces. The module includes a substrate holding position and first and second measurement instruments. The first instrument includes a first illumination path extending to the substrate holding position and having a grazing angle of incidence with the first surface, which illuminates substantially the entire first surface. A first optical element is oriented to collect non-specularly reflected light scattered by the first surface. A first photodetector has a plurality of pixels positioned within a focal plane of the first lens, which together form a field of view that covers substantially the entire first surface. The second instrument includes a sensor oriented for sensing a physical characteristic of the second surface when the substrate is held in the substrate holding position and the first surface is being illuminated.

15 Claims, 22 Drawing Sheets

U.S. PATENT DOCUMENTS

| | | | |
|---|---|---|---|
| 4,979,815 A | 12/1990 | Tsikos | 356/1 |
| 5,177,559 A | 1/1993 | Batchelder et al. | 356/237 |
| 5,189,481 A | 2/1993 | Jann et al. | 356/73 |
| 5,274,434 A | 12/1993 | Morioka et al. | 356/237 |
| 5,317,380 A | 5/1994 | Allemand | 356/338 |
| 5,355,212 A | 10/1994 | Wells et al. | 356/237 |
| 5,417,537 A | 5/1995 | Miller | 414/217 |
| 5,428,442 A | 6/1995 | Lin et al. | 356/237 |
| 5,450,205 A | 9/1995 | Sawin et al. | 356/382 |
| 5,479,252 A | 12/1995 | Worster et al. | 356/237 |
| 5,493,123 A | 2/1996 | Knollenberg et al. | 250/372 |
| 5,608,155 A | 3/1997 | Ye et al. | 73/28.01 |
| 5,628,954 A | 5/1997 | Sato | 438/16 |
| 5,629,768 A | 5/1997 | Hagiwara | 356/237.1 |
| 5,631,733 A | 5/1997 | Henley | 356/237 |
| 5,659,390 A | 8/1997 | Danko | 356/237 |
| 5,777,729 A | 7/1998 | Aiyer et al. | 356/237 |
| 5,808,278 A | 9/1998 | Moon et al. | 219/506 |
| 5,838,433 A * | 11/1998 | Hagiwara | 356/364 |
| 5,854,674 A | 12/1998 | Lin | 356/237 |
| 5,859,698 A | 1/1999 | Chau et al. | 356/237 |
| 5,864,394 A | 1/1999 | Jordan, III et al. | 356/237 |
| 5,909,276 A | 6/1999 | Kinney et al. | 356/237 |
| 5,970,168 A | 10/1999 | Montesanto et al. | 382/149 |
| 5,987,160 A | 11/1999 | Harlow et al. | 382/145 |
| 6,084,664 A | 7/2000 | Matsumoto et al. | 356/237.4 |
| 6,104,481 A * | 8/2000 | Sekine et al. | 356/237.5 |
| 6,115,120 A | 9/2000 | Moriya et al. | 356/337 |
| 6,156,580 A | 12/2000 | Wooten et al. | 438/16 |
| 6,169,602 B1 | 1/2001 | Taniguchi et al. | 356/399 |
| 6,204,917 B1 | 3/2001 | Smedt | 356/237.5 |
| 6,292,260 B1 | 9/2001 | Lin et al. | 356/237.4 |
| 6,392,738 B1 | 5/2002 | van de Pasch et al. | 355/30 |
| 6,401,008 B1 | 6/2002 | Ehrichs et al. | 700/228 |
| 6,407,373 B1 | 6/2002 | Dotan | 250/201.3 |

OTHER PUBLICATIONS

D.R. Oswald and D.F. Munro, "A Laser Scan Technique for Electronic Materials Surface Evaluation", Journal of Electronic Materials, vol. 3, No. 1, 1974.

H, Altendorfer, G. Kren et al. "Unpatterned Surface Inspection for Next Generation Devices", Solid State Technology, 1996, pp 93–99.

C. Bakolias and A.K. Forrest, "Dark Field, Scheimpflug Imaging for Surface Inspection", Machine Vision Applications in Industrial Inspection V, 1997, San Jose, CA SPIE.

P. Burggraaf, "Patterned Wafer Inspection: Now Required !", Semiconductor International 17(14) : pp 57–58 60, 1994.

D.L. Cavan, L.H. Lin et al., "Patterned Wafer Inspection Using Laser Holographer and Spatial Frequency Filter," Journal of Vacuum Science and Technology, 6(6): pp 1934–1939, 1988.

R. Ceton, R. Goodner, et al., "Comparison of Patterned Wafer effect Detection Tools for General In–Line Monitors," IEEE/SEMI Advanced Semiconductor Manufacturing Conference, IEEE, 1996.

F.E. Doany, R.N. Singh et al., "Projection Display Throughout: Efficiency of Optical Transmission and Light–Source Collection," IBM Journal of Research and Development, 42(3) pp 387–400, 1998.

B.E. Dom, R. Bonner et al., "The P300: A System for Automatic Patterned Wafer Inspection," Machine Vision and Applications, vol. 1, pp 205–221, 1988.

R.S. Howland, K.B. Wells et al., "High–Speed Detection of Pattern Defects using Laser Scattering," Solid State Technology, 38(11): pp 123–126, 1995.

H. Moench, G. Derra et al., "Optimised Light Sources for Projection Displays,".

H. Moench, G. Derra et al., "Arc Stabilization for Short Arc Projection Lamps," SID 2000, Society of Information Display, 2000.

W. Morrow, R. Howland et al., "High–Speed Pattern Defect Detection Using Laser Scattering," Proceedings of the Institute of Environmental Sciences, pp 232–236, 1996.

A.K. Prasad, "Stereoscopic Particle Image Velocimetry," Experiments in Fluids, vol. 29, pp 103–116, 2000.

T. Reuter and U. Bohmler, "Using Laser–Based Patterned–Wafer Inspection for Memory and Logic Applications," Micro pp 89–95, 1999.

D. Roudin, P.D. Kinney et al., "New Sample Preparation Method for Improved Defect Characterization Yield on Bare Wafers," In–Line Methods and Monitors for Process and Yield Improvement, Santa Clara, CA, SPIE, 1999.

P. Sandland, "Automated Defect Inspection: Past, Present & Future," SPIE 1998.

S.O. Schellenberg, and U. Herdickerhoff, "Recognition of Defects of the Surfscan Installation Tencor 7600 Depending on the Situation and Size of the Defect," SPIE Conference on Microelectronic Manufacturing Yield, Reliability, and Failure Analysis IV, Santa Clara, CA SPIE 1998.

M.A. Taubenblatt and J.S. Batchelder, "Patterned Wafer Inspection Using Spatial Filtering for the Cluster Environment," Applied Optics, 31(17) pp 3354–3362, 1992.

B.M. Trafas, M. Nikoonahad et al. "Extendibility of Laser Scanning tools for Advanced Wafer Inspection," Proceedings of SPIE, 2439, pp 164–173, 1995.

L.S. Watkins, "Inspection of Periodic Patterns with Intensity Spatial Filters," Solid State Technology, 12(2), pp 35–38, 1969.

C.D. Allemand and J.J. Danko, "Heuristic Approach to Particle Detection on Virgin and Patterned Silicon Wafers," Optical Engineering, 34(2) pp 548–563, 1995.

K. Komatsu et al., "Automatic Macro Inspection System," SPIE Conference on Metrology, Inspection, and Process control for Microlithography XIII, Santa Clara, CA Mar. 1999, pp 764–771.

\* cited by examiner

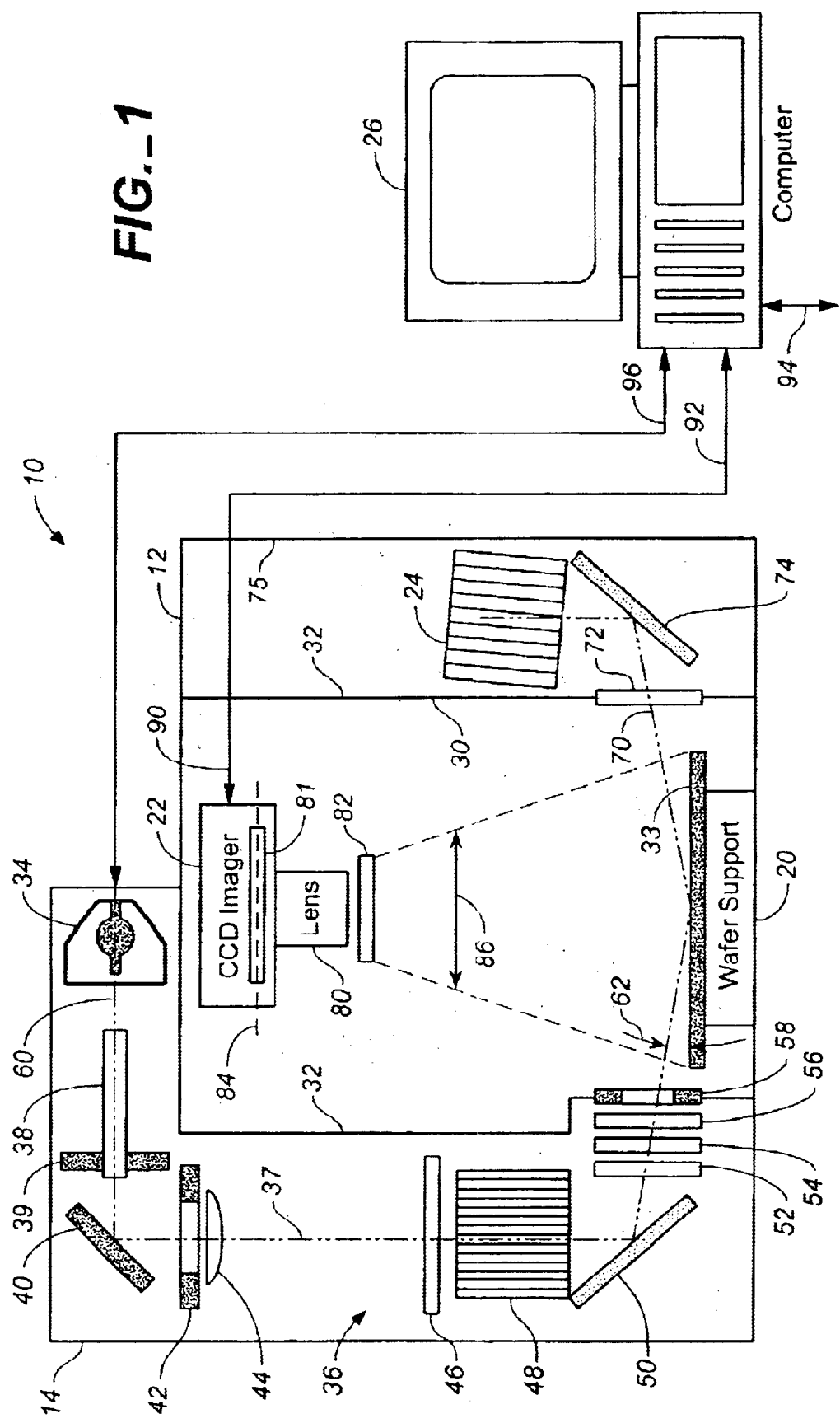
FIG._1

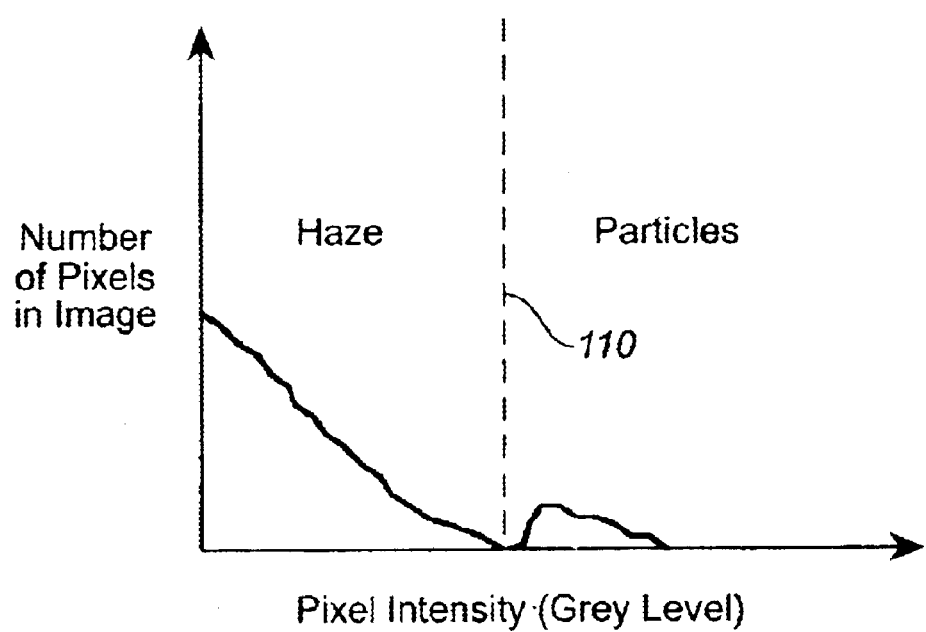
FIG._2

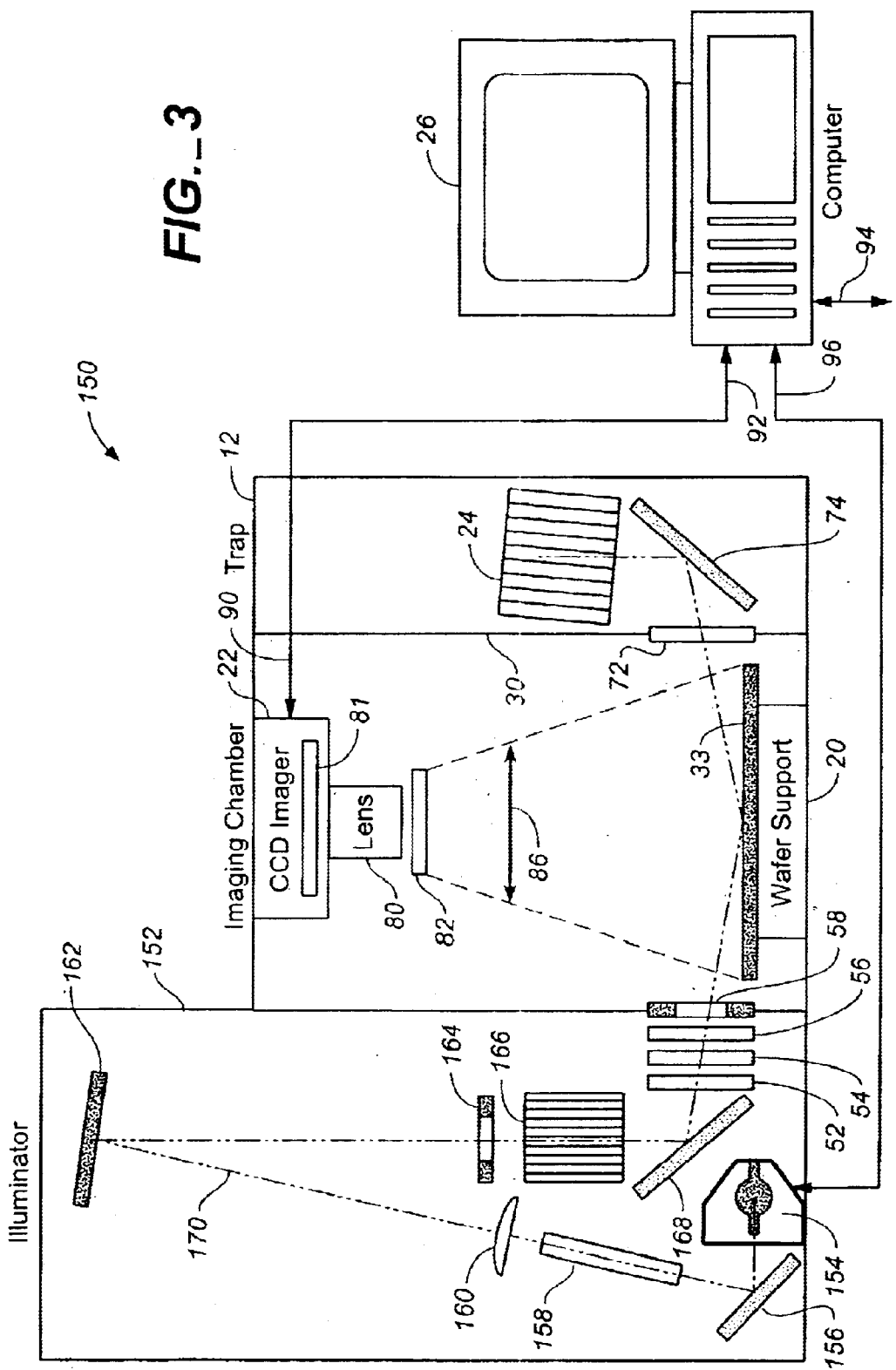
FIG._3

FIG._4A  FIG._4B  FIG._4C

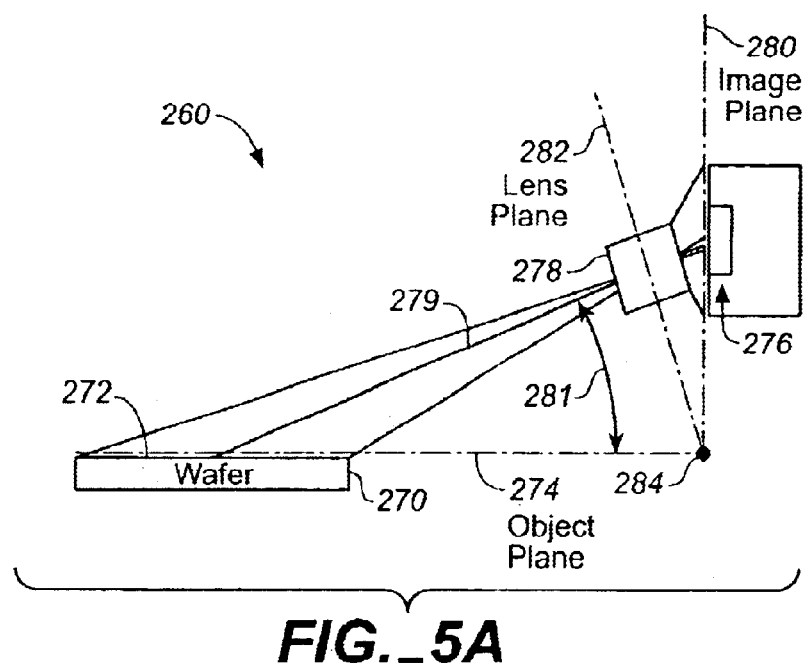
FIG._5A
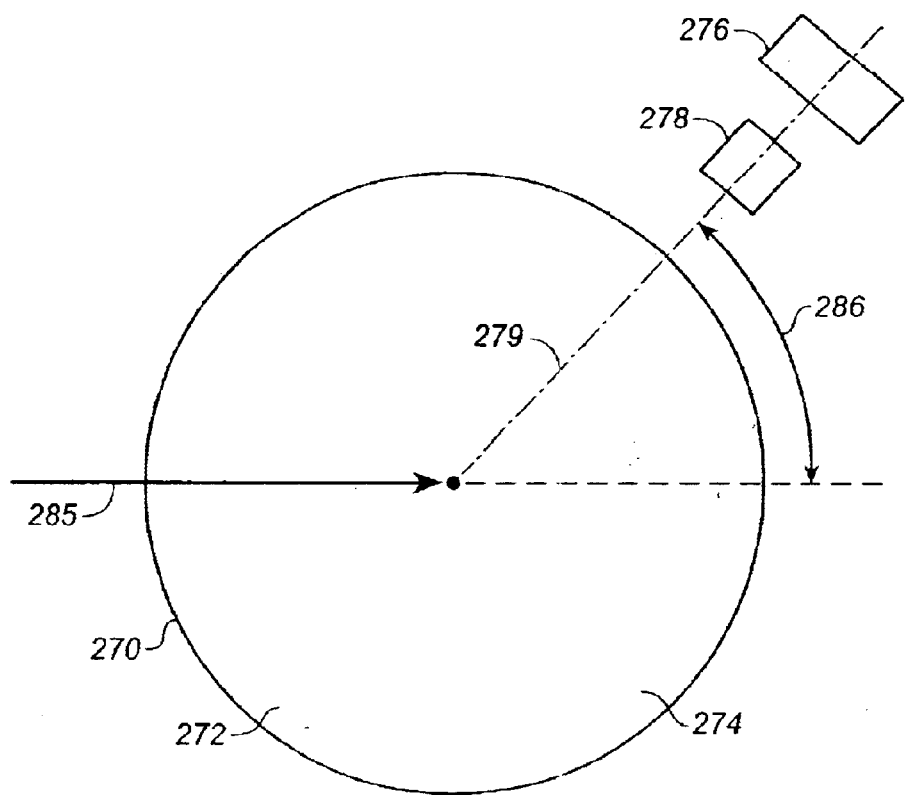
FIG._5B

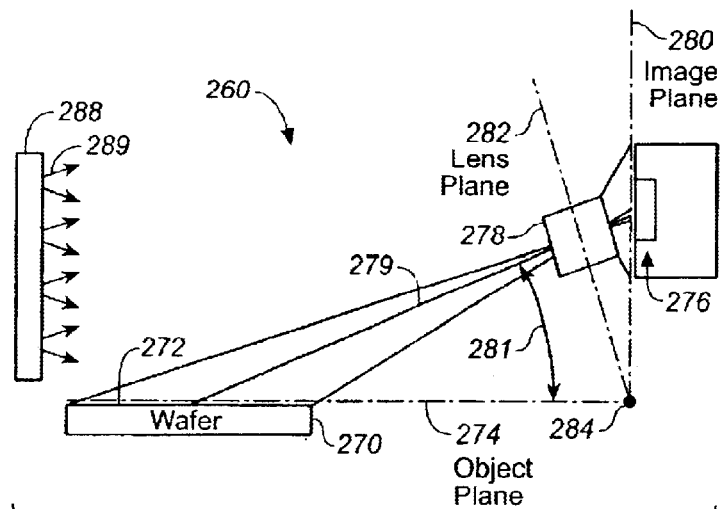
FIG._5C
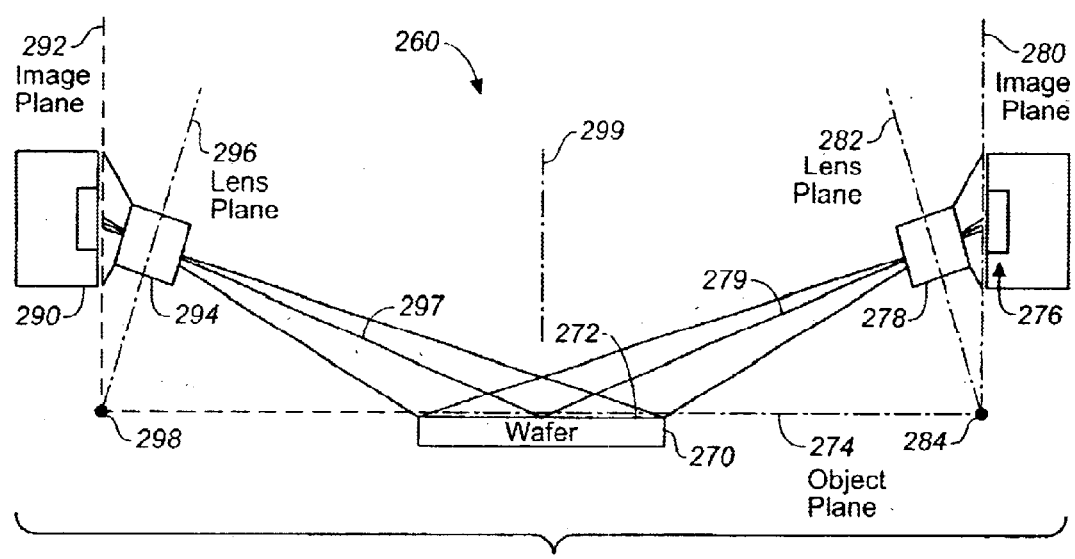
FIG._5D

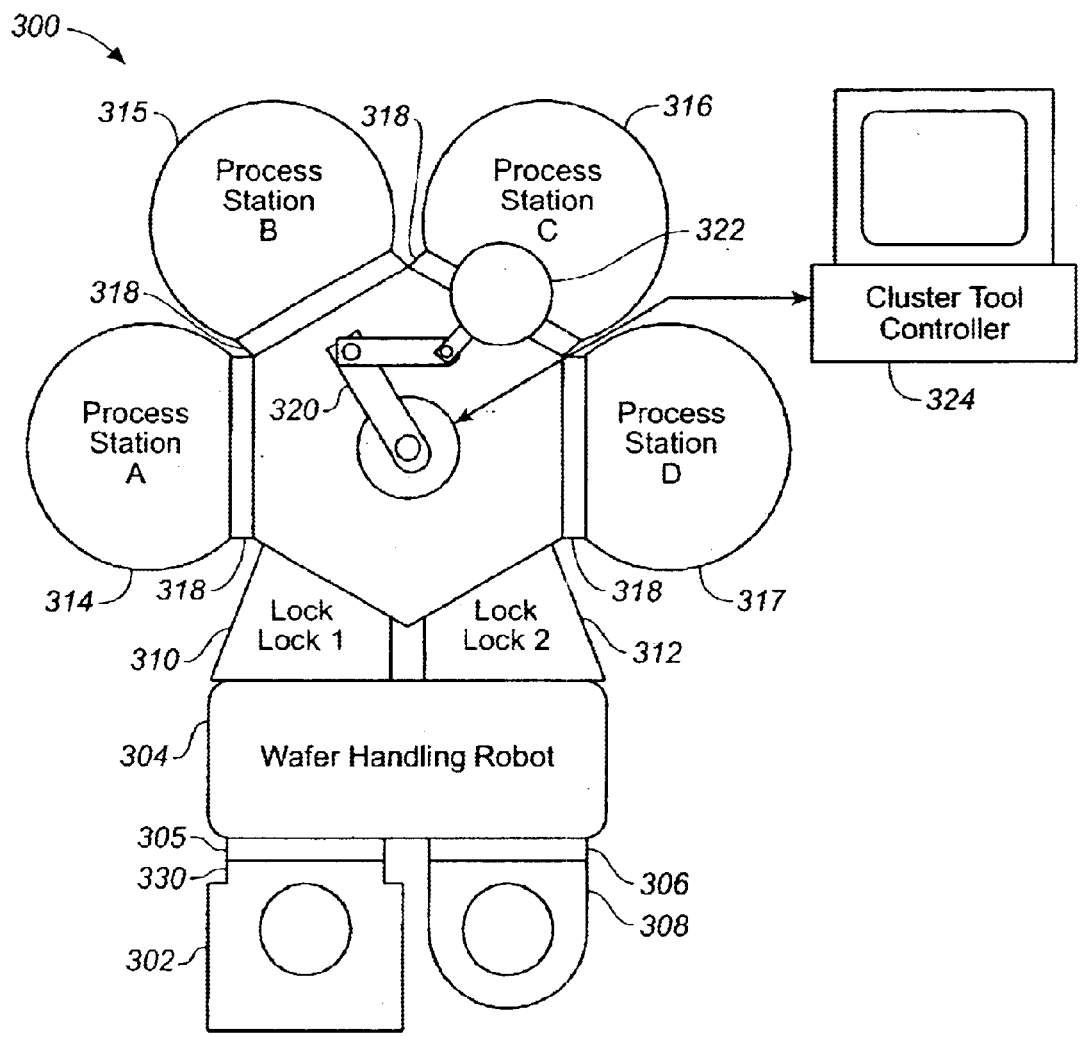
FIG._6

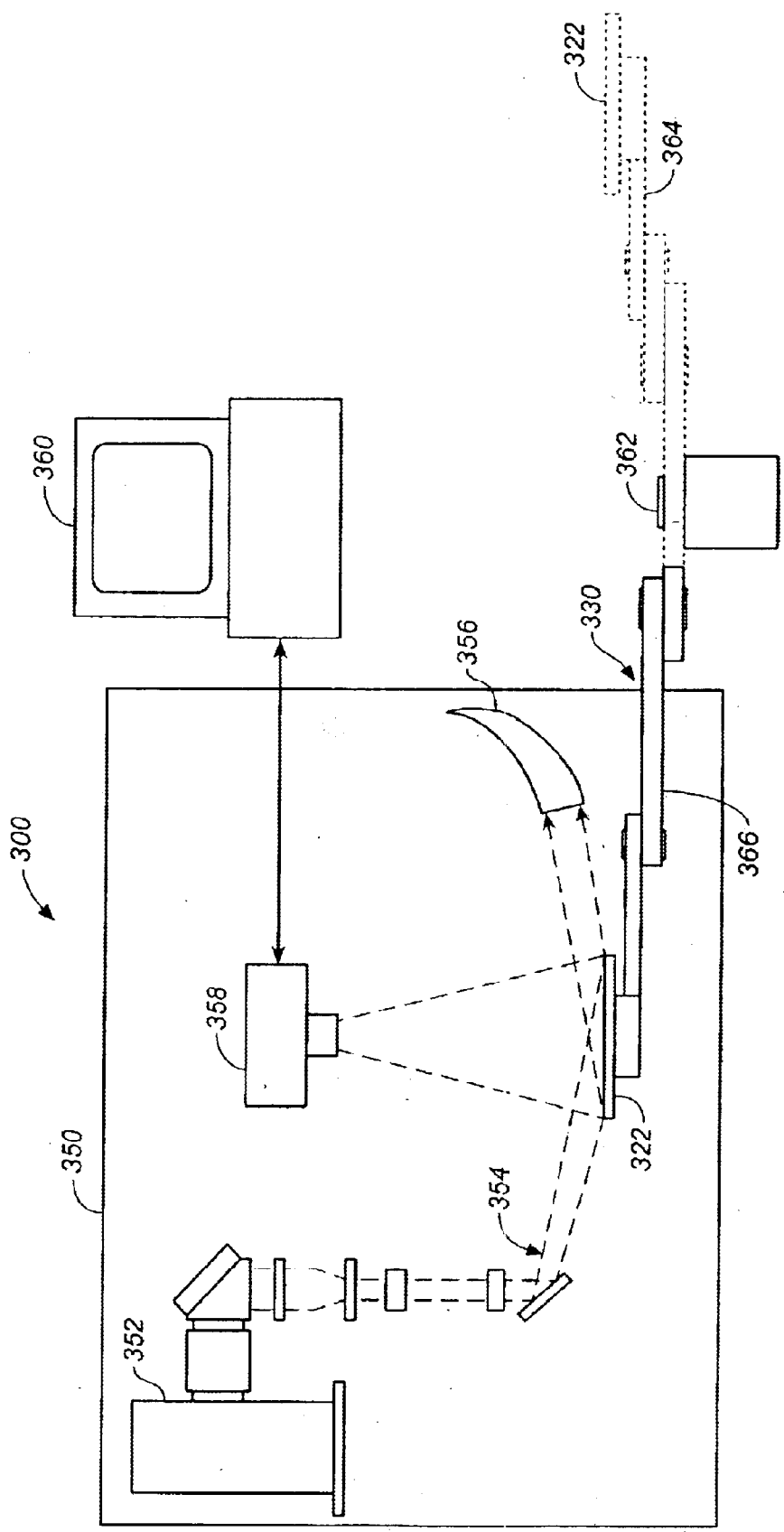
FIG._7

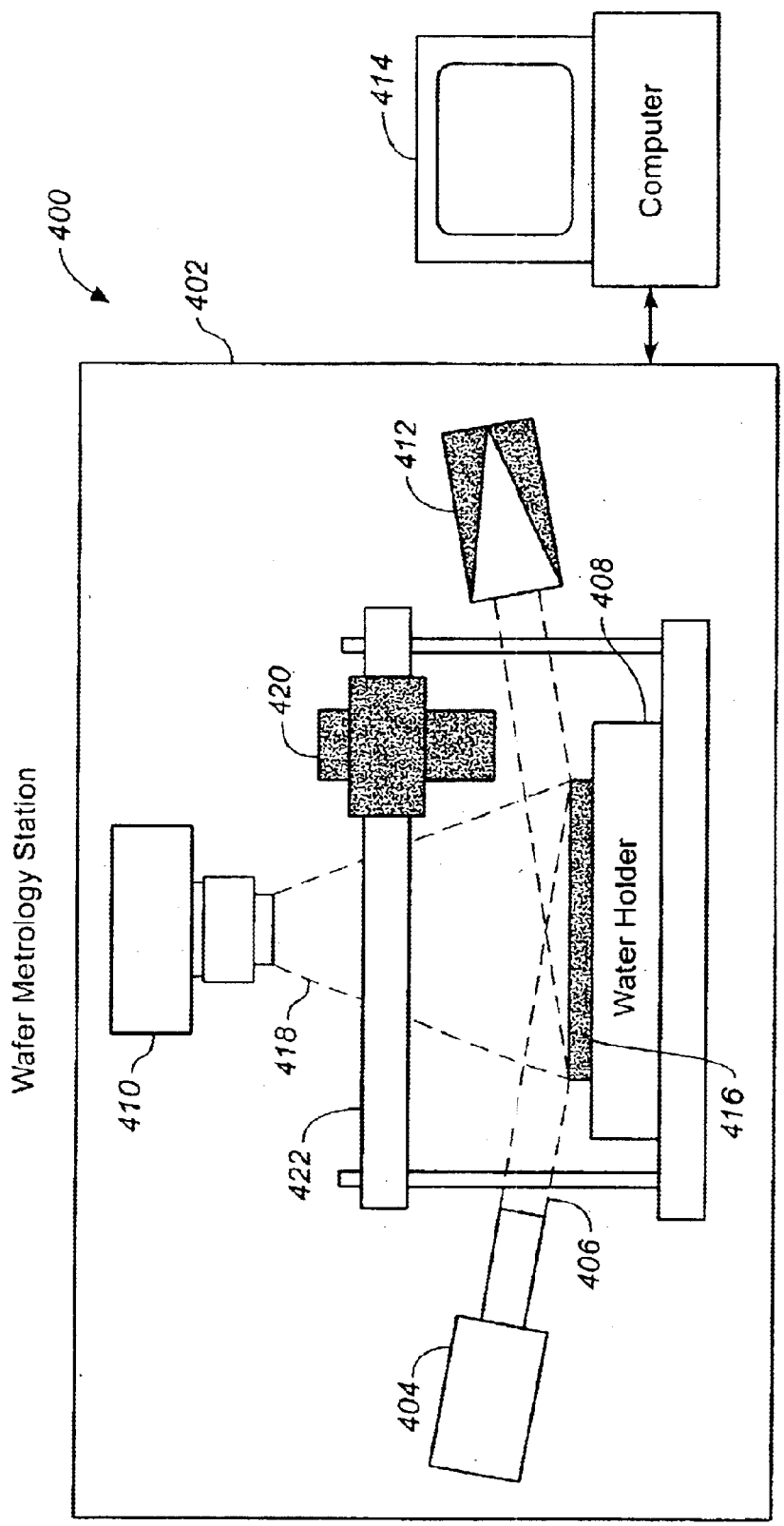
FIG._8

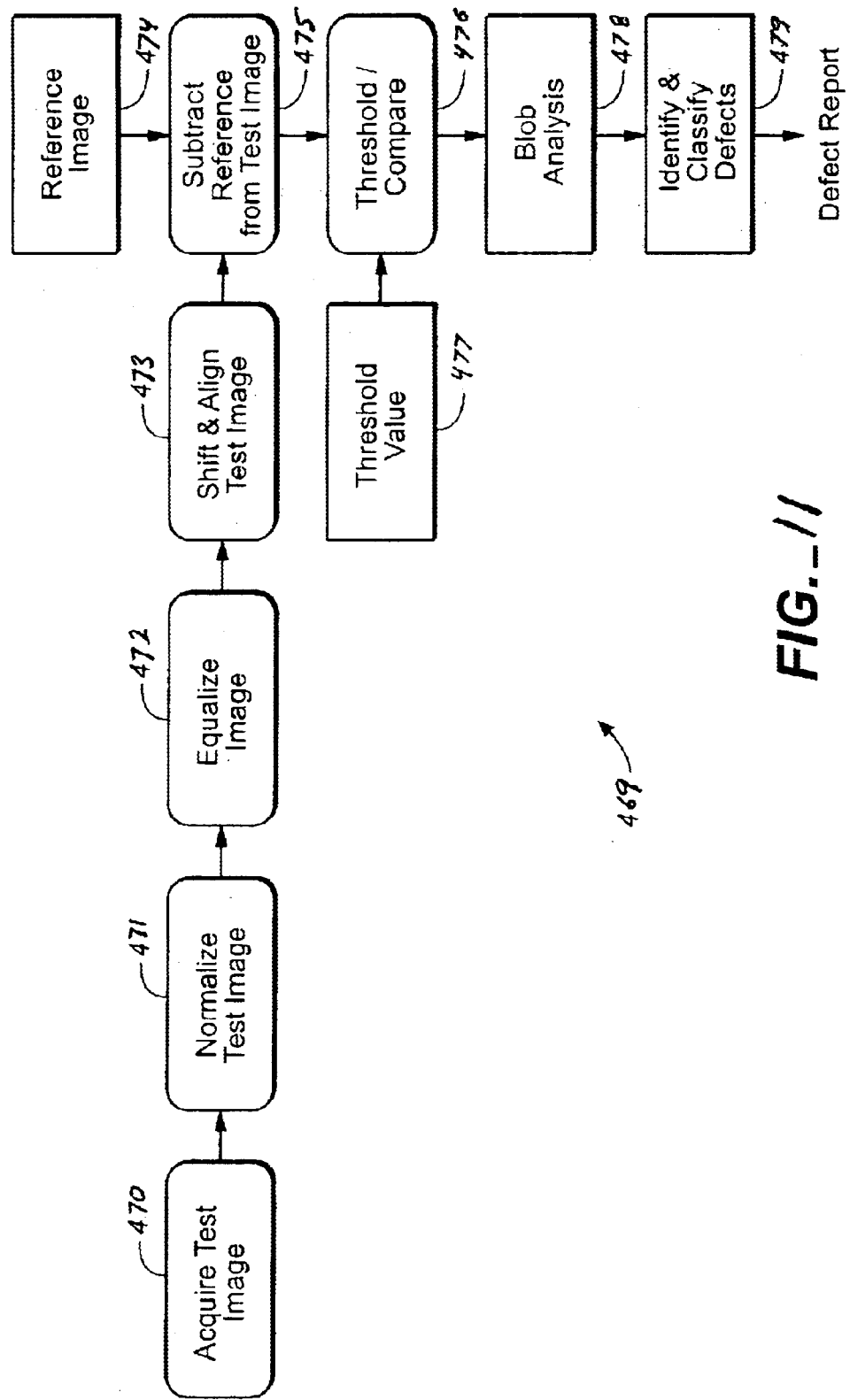
FIG._11

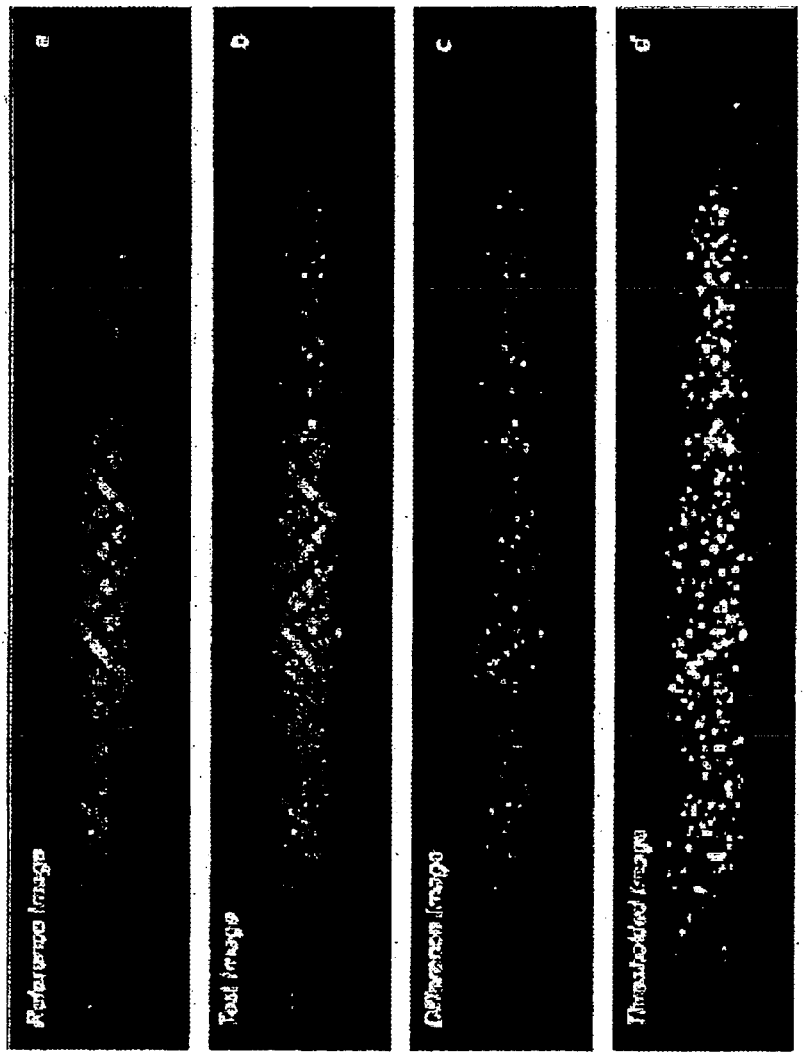
FIG._12A
FIG._12B
FIG._12C
FIG._12D

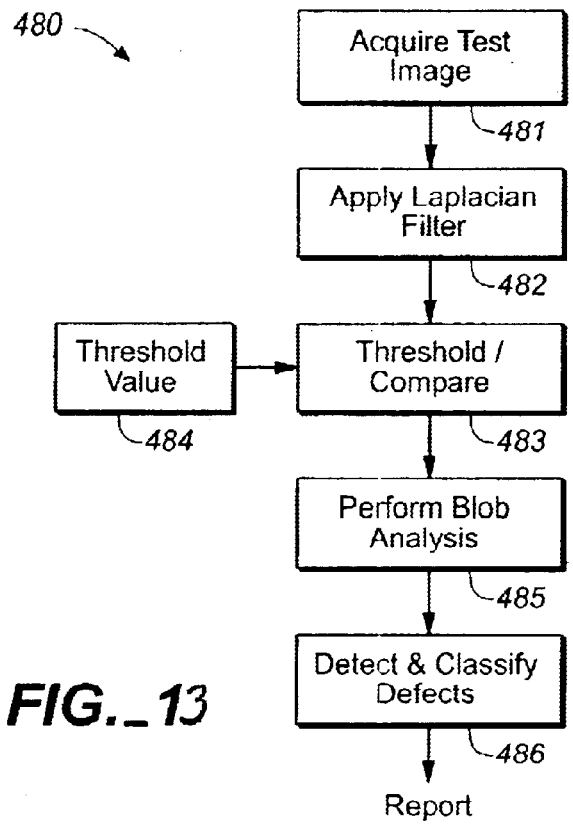
FIG._13
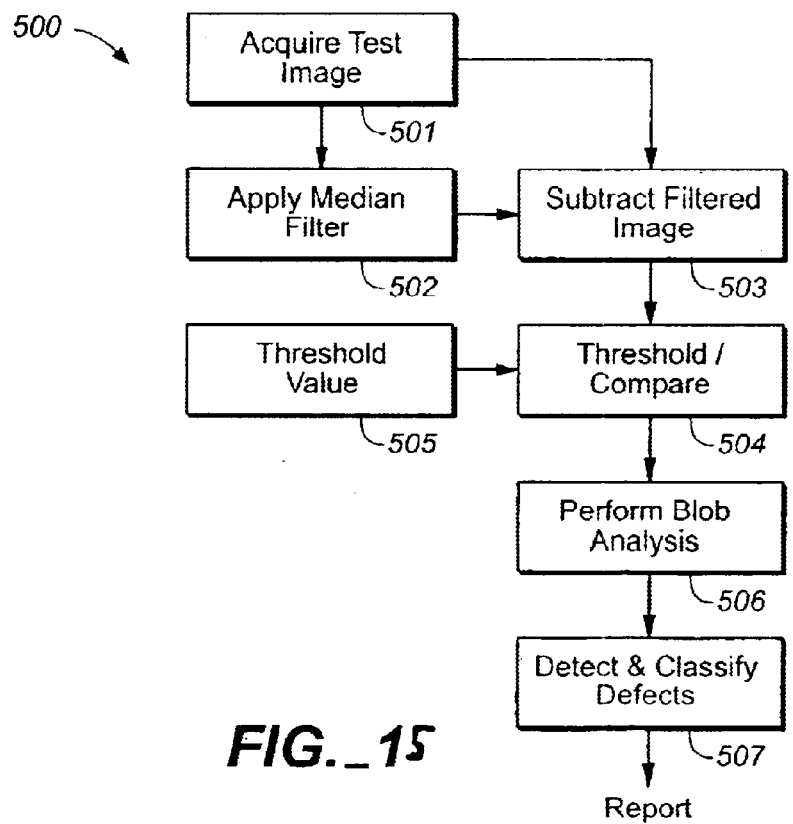
FIG._15

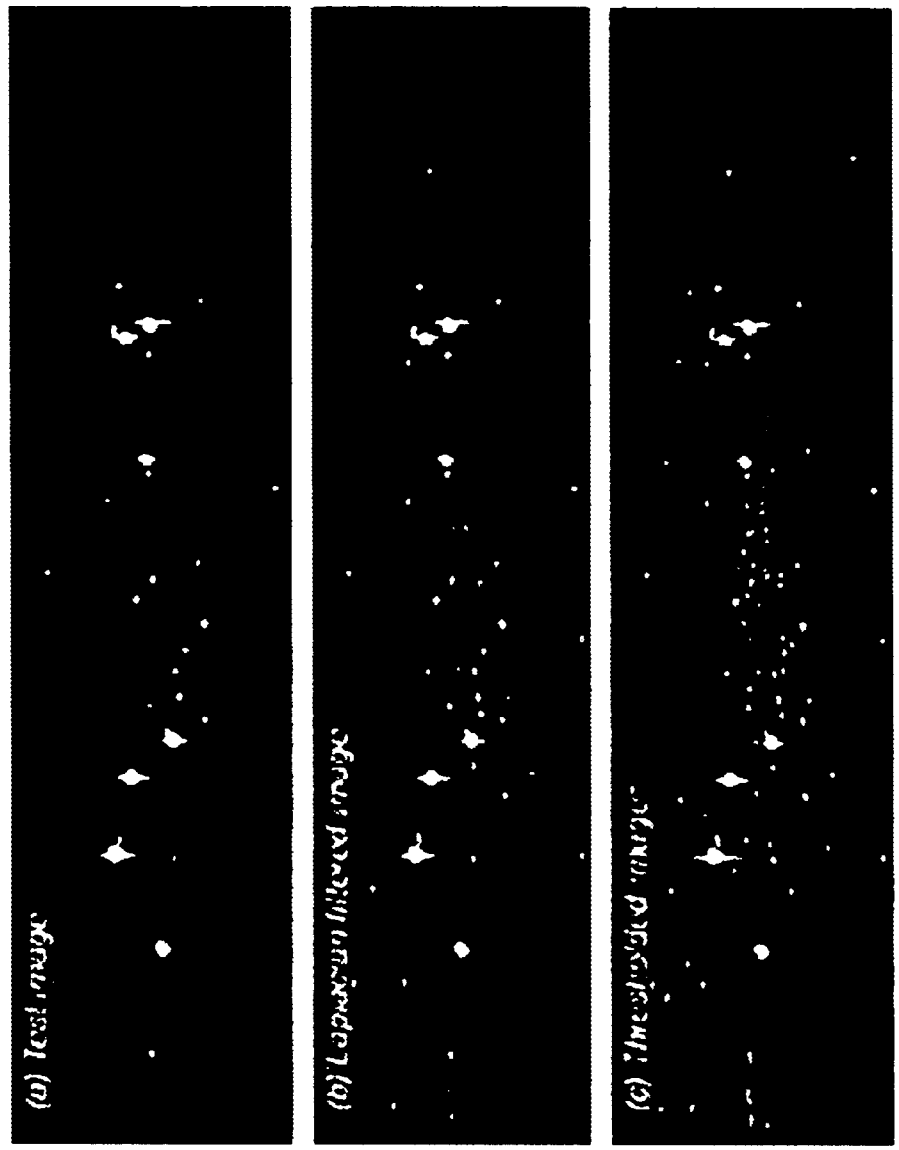
FIG._14A  FIG._14B  FIG._14C

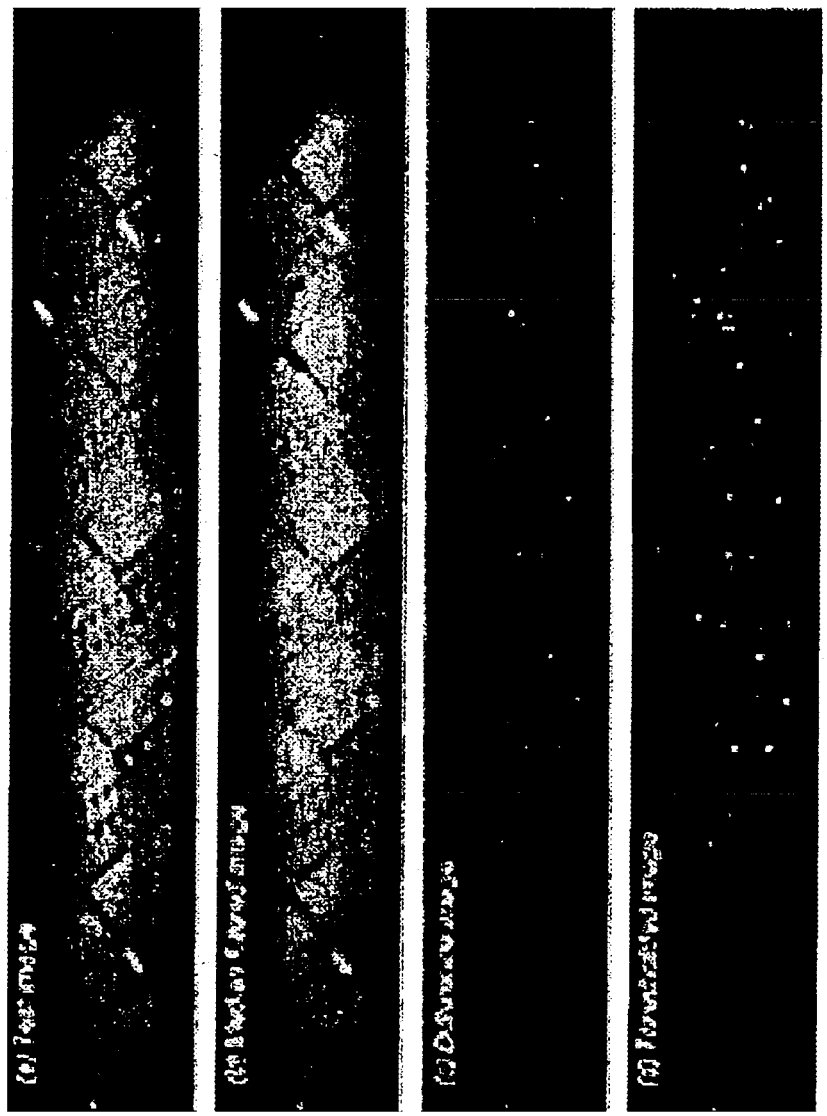
FIG._16A
FIG._16B
FIG._16C
FIG._16D

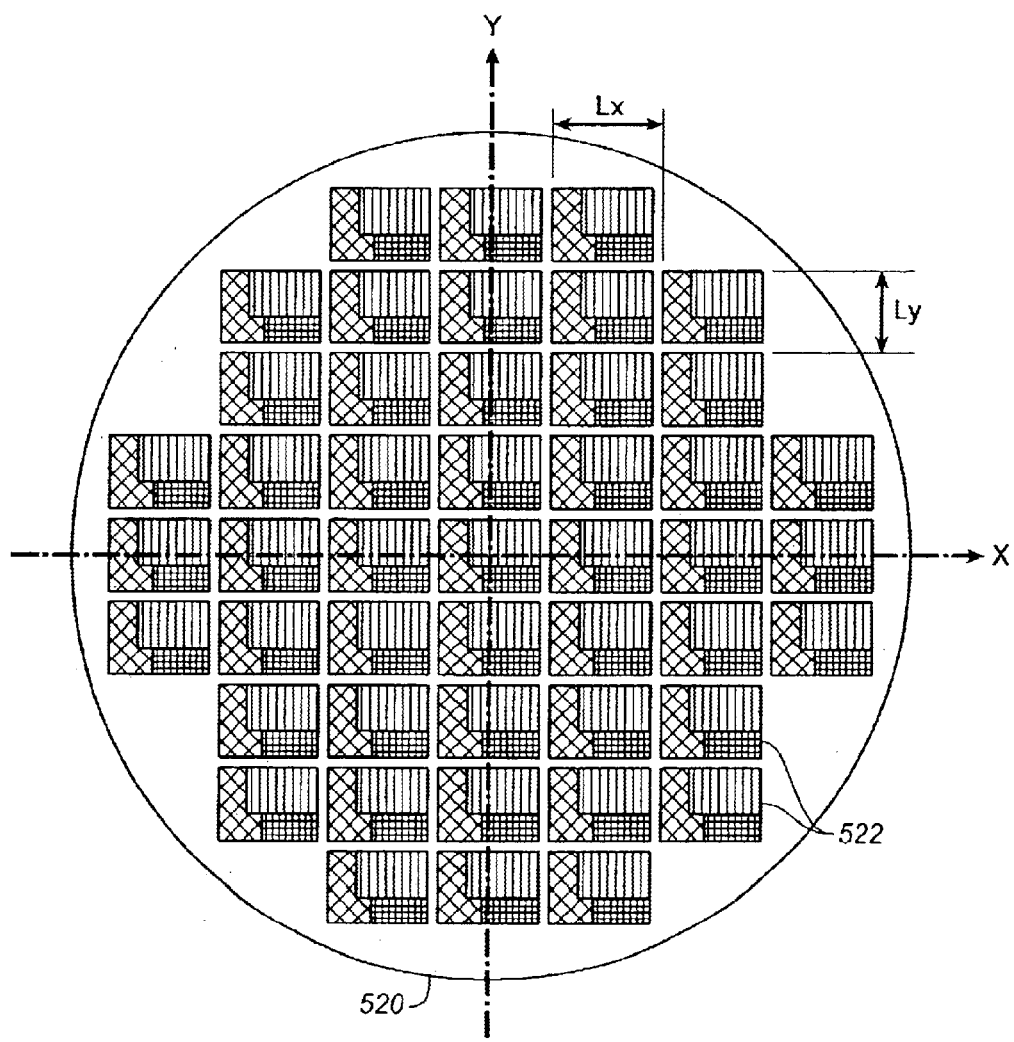
FIG._17

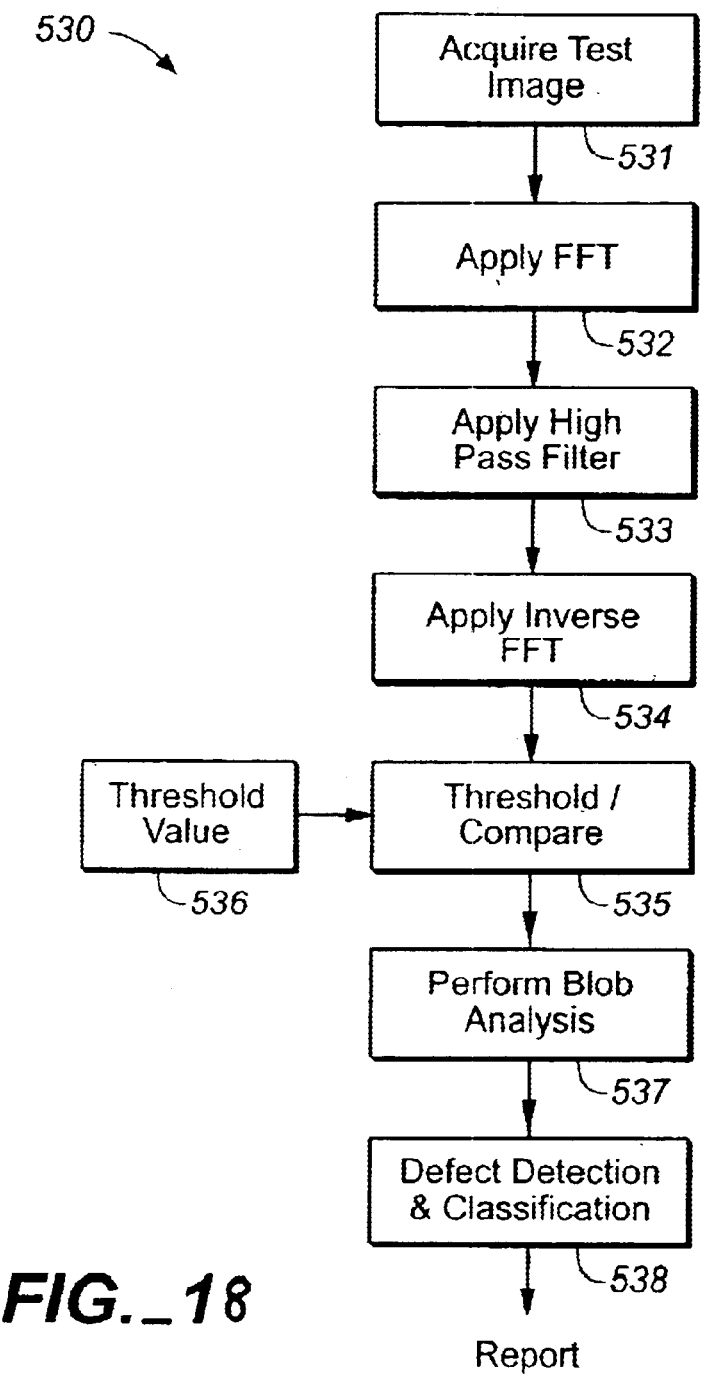
FIG._18

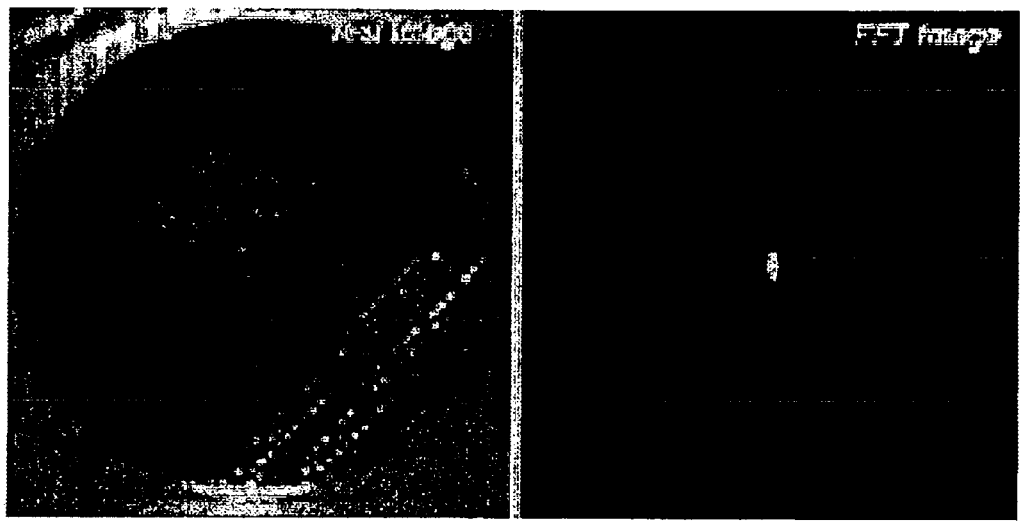
FIG._19A  FIG._19B

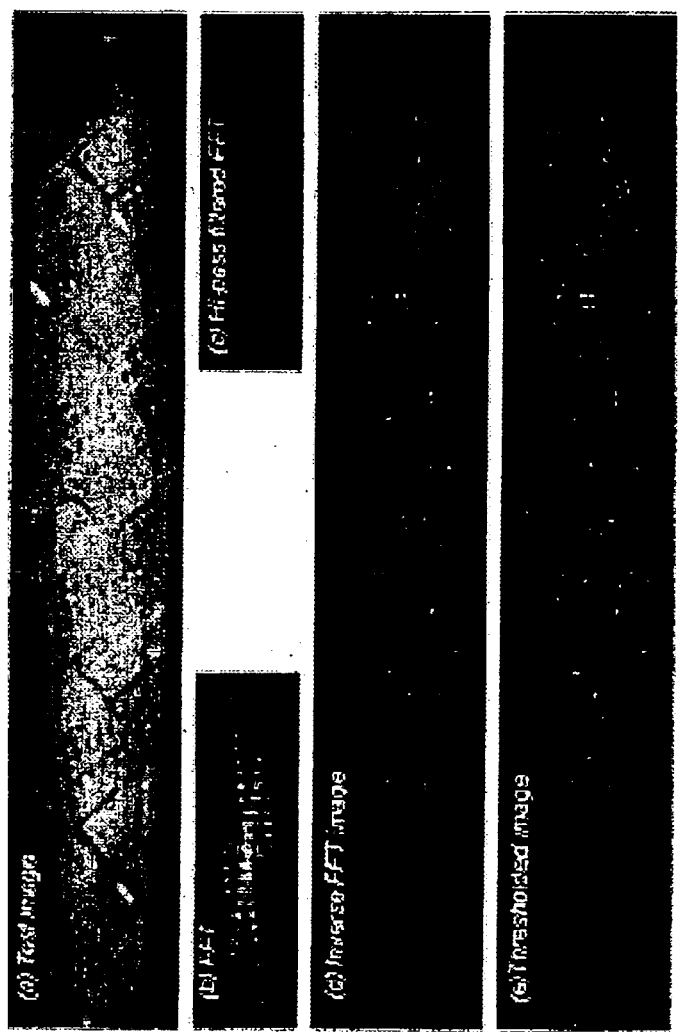
FIG._20A  FIG._20B  FIG._20C  FIG._20D  FIG._20E

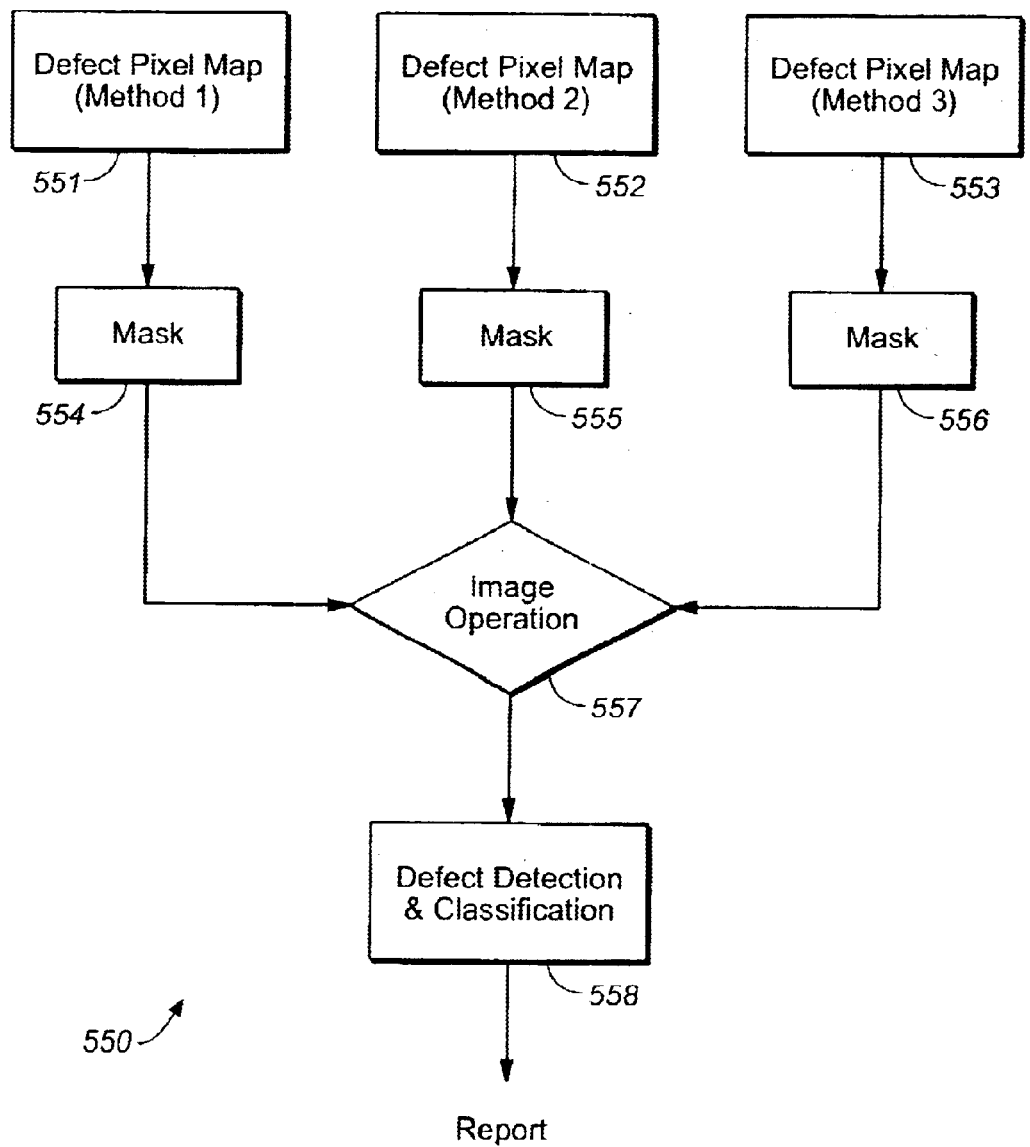
FIG._21

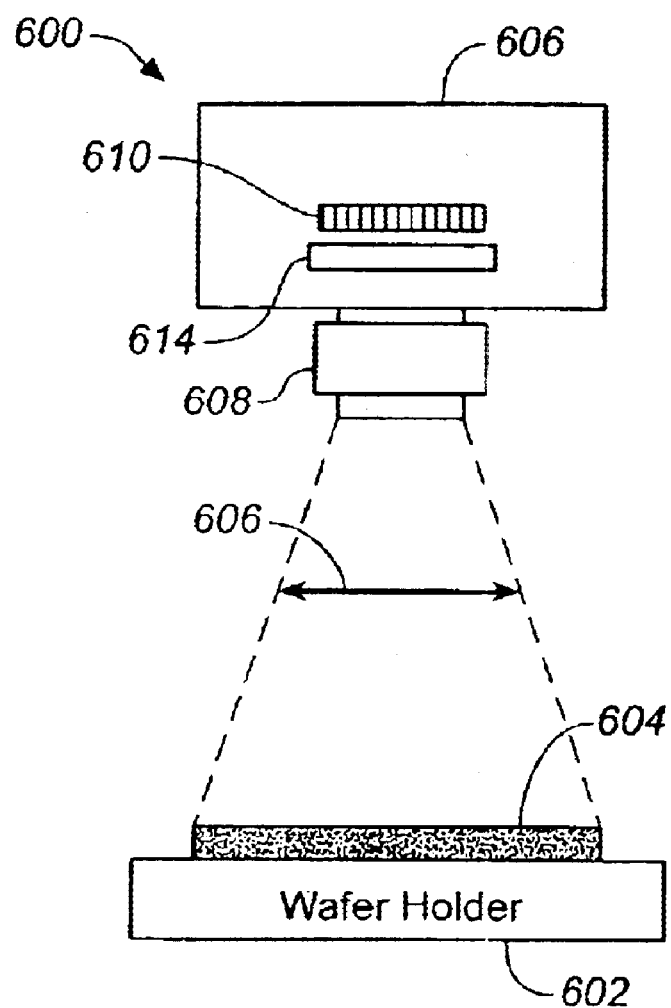
FIG._22

OPTICAL METHOD AND APPARATUS FOR INSPECTING LARGE AREA PLANAR OBJECTS

CROSS-REFERENCE TO RELATED APPLICATIONS

The present application claims the benefit of U.S. Provisional Application No. 60/361,799, filed Mar. 5, 2002 and is a continuation-in-part of U.S. application Ser. No. 09/994,021, filed Nov. 14, 2001, now U.S. Pat. No. 6,630,996, which is based on and claims the benefit of U.S. Provisional Application No. 60/249,000, filed Nov. 15, 2000, and U.S. Provisional Application No. 60/297,660, filed Jun. 12, 2001, the contents of which are hereby incorporated by reference in their entirety.

FIELD OF THE INVENTION

The present invention relates to optical metrology for large-area substrates. In particular, the present invention relates to methods and apparatus used to detect defects and particle contamination on such substrates.

BACKGROUND OF THE INVENTION

It is well known that the presence of contaminant particles on the surface of electronic substrates such as semiconductor wafers can lead to the formation of defects during the microelectronics fabrication process. In order to maintain high manufacturing yield and thus low manufacturing costs, it is necessary that contaminated wafers be identified during the manufacturing process. Several automated optical inspection systems are commercially available for the purpose of detecting particles and defects on wafers and like substrates.

In general, wafer inspection systems can be divided into two broad classes: (i) those that detect particles by light scattering as the wafer surface is scanned by a laser; and (ii) those that detect particles and defects through processing of a captured digital image. In both these approaches, generally only a small portion of the wafer is illuminated at a time, therefore requiring the wafer to move relative to the illuminating beam to enable the entire surface to be inspected. The laser light scattering systems have traditionally been used mainly for inspecting un-patterned wafers, while the digital image processing systems have been used mainly for inspecting patterned wafers. Recently, laser scanning and light scattering systems have also been used for detecting defects on patterned wafers.

Wafer inspection tools such as those described above have been configured as specialized stand-alone inspection systems designed to provide sensitivity to extremely small defects and particles, and are thus complex in design and expensive. In semiconductor production fabs, patterned wafer inspection tools are used to monitor defects on product wafers. Many of these tools are digital image processing systems, which typically use microscope objectives to image a small portion of the wafer at a time. The pixel size is typically on the order of the minimum feature size, requiring an enormous number of pixels to be processed. For example, detection of 0.5 micrometer ($\mu$m) minimum defects on a 150 millimeter (mm) wafer requires about $2.8 \times 10^{11}$ pixels. For 200 mm wafers the corresponding number of pixels to be processed is on the order of $5 \times 10^{11}$ or higher. Since the inspection throughput of such systems is fairly low, only a few wafers per lot are normally inspected. Additionally, the high cost of these inspection systems necessarily means that the number of such systems present in production lines used in microelectronics manufacture is low, with the result that inspections for particles and defects are relatively few and far between. Since a very large number of process steps are involved in the manufacture of microelectronics and semiconductor devices, a sparse sampling of wafers in the production line may lead to contaminated wafers remaining undetected for a long period of time, leading to lower yield and increased rework costs.

More recently, wafer inspection tools designed for integration into microelectronics processing equipment have been disclosed. These integrated metrology tools are designed to perform in-line inspection of wafers, and therefore provide rapid feedback of process excursions and other problems. A related class of fast wafer inspection tools is known in the industry as "macro-inspection" tools, which are also available for in-line inspection of wafers in the manufacturing line.

At present, the wafer inspection tools available for integrated metrology have the drawbacks of being either too slow (inspection taking greater than 60 seconds per wafer) or too insensitive (less than 25 micrometer defect sensitivity), and these drawbacks limit the application of such prior art methods. Furthermore, presently available wafer inspections systems inspect only one surface of the wafer, usually the top (or active) surface, onto which the integrated circuits are etched. In general, wafer inspection systems also exclude the wafer edges from inspection. They are thus not suited for some of the newly emerging applications such as the inspection of the wafer's edges, back surface and bevels.

Copper contamination of the wafer back surface has the potential to contaminate process metrology and handling equipment, which could in turn contaminate wafers that come into contact with them. Additionally, copper deposited on the wafer bevel can flake off in subsequent processing steps such as annealing and chemical mechanical polishing (CMP). Particles on the back surface of the substrate can cause focal problems during lithography and can result in rejected wafers. According to the International Technology Roadmap for Semiconductors, the backside particle requirement for optical lithography is less than 94 particles per 300 millimeter wafer for 0.18 micrometer technology, and less than 63 particles per wafer for 0.13 micrometer technology for particles that are greater than 0.2 micrometers.

There have been recent attempts to develop tools capable of inspecting both surfaces of a semiconductor wafer. For example, U.S. Pat. Nos. 6,156,580 and 6,401,008 disclose a wafer review system and method in which the front and back surfaces of a semiconductor wafer are inspected sequentially. First, the front surface of the wafer is scanned by an optical inspection tool. Then, the wafer is flipped using a wafer inverter to present the back surface for inspection. Although both the front and back surfaces are inspected, sequential inspection results in a low inspection throughput.

U.S. Pat. No. 6,204,918 discloses an optical device for simultaneously inspecting the front and back surfaces of a semiconductor wafer for defects. The system rotates the wafer while the front and back surfaces of the wafer are simultaneously scanned for defects. An air bearing is used to float the wafer on a cushion of air to eliminate contamination of the wafer surface due to contact with a wafer support surface. The wafer is rotated using motor-driven rollers that are positioned at the circumference of the wafer so that the rollers contact the wafer only at its beveled edges, thereby reducing edge contamination and permitting inspection of the entire wafer surface. While this wafer inspection system enables simultaneous inspection of wafer front and back surfaces, only a portion of the wafer surface is scanned at a time. This also limits inspection throughput. Further, the need for air bearing and wafer rotation mechanisms add complexity, bulk and cost to the system, making it less suitable for integrated metrology applications.

U.S. Pat. No. 6,392,738 discloses a backside inspection system for integrated metrology applications. In this system, a scanning laser-based backside inspection tool is integrated into a lithographic projection apparatus. However, this system also uses relatively complex mechanisms for rotating the wafer and translating the illuminating laser beam, and is capable of inspecting only a portion of the wafer at a time.

Thus, there is a need for new and improved inspection systems for inspecting both sides of a substrate. These systems should be flexible enough to handle the existing and immerging demands of the semiconductor industry, such as high speed, low cost, in-line inspection of the sub-micron defects.

SUMMARY OF THE INVENTION

One embodiment of the present invention is directed to an optical inspection module for inspecting a substrate having first and second opposite planar surfaces. The module includes a substrate holding position and first and second measurement instruments. The first measurement instrument includes a first illumination path extending to the substrate holding position and having a grazing angle of incidence with respect to the first surface of the substrate when the substrate is held in the substrate holding position. The first illumination path illuminates substantially the entire first surface. A first optical element is oriented to collect non-specularly reflected light that is scattered from the first illumination path by the first surface. A first photodetector has a plurality of pixels, which are positioned within a focal plane of the first optical element. Each pixel corresponds to an area on the first surface and the plurality of pixels together form a field of view that covers substantially the entire first surface. The second measurement instrument includes a sensor oriented for sensing a physical characteristic of the second surface when the substrate is held in the substrate holding position and the first surface is being illuminated.

Another embodiment of the present invention is directed to an optical inspection module for inspecting a substrate having first and second opposite planar surfaces. The module includes a substrate holding position and a first illumination path extending to the substrate holding position and having a grazing angle of incidence with respect to the first surface of the substrate when the substrate is held in the substrate holding position. The first illumination path illuminates substantially the entire first surface. A first optical element is oriented to collect non-specularly reflected light that is scattered from the first illumination path by the first surface. A first photodetector has a plurality of pixels, which are positioned within a focal plane of the first optical element. Each pixel corresponds to an area on the first surface, and the plurality of pixels together form a field of view that covers substantially the entire first surface. The module further includes a second illumination path extending to the substrate holding position and having a grazing angle of incidence with respect to the second surface when the substrate is held in the substrate holding position. The second illumination path illuminates substantially the entire second surface. A second optical element is oriented to collect non-specularly reflected light that is scattered from the second illumination path by the second surface. A second photodetector has a plurality of pixels, which are positioned within a focal plane of the second optical element. Each pixel corresponds to an area on the second surface, and the plurality of pixels together form a field of view that covers substantially the entire second surface.

Another embodiment of the present invention is directed to an optical inspection module for detecting defects on a substrate having an active surface and an opposite, back surface. The module includes a substrate holding position and first and second measurement instruments. The first instrument includes a first illumination path extending to the substrate holding position and having a grazing angle of incidence with the back surface when the substrate is held in the substrate holding position. The first illumination path illuminates substantially the entire back surface. A first optical element is oriented to collect non-specularly reflected light that is scattered from the first illumination path by defects on the back surface. A first photodetector has a plurality of pixels, which are positioned within a focal plane of the first optical element. Each pixel corresponds to an area on the back surface and the plurality of pixels together form a field of view that covers substantially the entire back surface. The second measurement instrument includes a second illumination path extending to the substrate holding position and illuminating at least a portion of the active surface when the substrate is held in the substrate holding position. A second optical element is oriented to collect light reflected from the second illumination path by the active surface. A second photodetector has at least one pixel, which is positioned within a focal plane of the second optical element. The second measurement instrument has a defect sensitivity that is greater than that of the first measurement instrument and is capable of detecting smaller defects on the active surface than the first measurement instrument is capable of detecting on the back surface.

BRIEF DESCRIPTION OF THE DRAWINGS

FIG. 1 is a schematic representation of a large area optical inspection module for detecting particles and other features on a substrate according to one embodiment of the present invention.

FIG. 2 is histogram illustrating an example of the number of pixels in a substrate image as a function of pixel intensity.

FIG. 3 is a schematic representation of an optical inspection module having an alternative illuminator.

FIGS. 4A–4C are photographs showing a sequence of images obtained by inspecting a patterned wafer through the detection of de-polarized scattered light with the module shown in FIG. 1.

FIG. 5A is a schematic illustration of an optical inspection module for imaging at an oblique angle to the substrate surface.

FIG. 5B is a schematic top plan view of the optical inspection module shown in FIG. 5A, as viewed from above the substrate.

FIG. 5C is a schematic illustration of an optical inspection module for brightfield imaging at an oblique angle to the substrate surface, wherein the substrate is illuminated by a uniformly illuminated panel.

FIG. 5D is a schematic illustration of an optical inspection module for imaging at two oblique angles at one time.

FIG. 6 is a schematic illustration of a multi-process cluster tool system in which an inspection module is integrated into a load/unload port of the system, according to one embodiment of the present invention.

FIG. 7 is a schematic illustration of the inspection module shown in FIG. 6, which shows the insertion of a substrate by a wafer handling robot.

FIG. 8 is a schematic illustration of an integrated metrology station having two measurement instruments according to one embodiment of the present invention.

FIG. 11 is a flow chart, which shows an image acquisition and analysis process used to extract defects from a test image using a previously stored reference image according to one embodiment of the present invention.

FIGS. 12A–12D are photographs showing a sequence of images produced in the process shown in FIG. 11 for the case of a patterned wafer.

FIG. 13 is flow chart illustrating an example of an image acquisition and analysis process, which uses a convolution filter.

FIGS. 14A–14C are photographs showing a sequence of images produced in the process shown in FIG. 13 for the case of a bare wafer.

FIG. 15 is a flow chart illustrating an example of an image acquisition and analysis process, which uses spatial filtering.

FIGS. 16A–16D are photographs showing a sequence of images where spatial filtering has been used according to the process shown in FIG. 15 for the case of a patterned wafer.

FIG. 17 is schematic representation of a typical patterned wafer showing the regular placement of individual die.

FIG. 18 is flow chart illustrating an image acquisition and analysis process which uses computerized frequency filtering to detect defects on patterned wafers.

FIG. 19A shows a test image of a patterned 200 millimeter wafer.

FIG. 19B shows the corresponding frequency spectrum image obtained by computing a fast Fourier Transform of the test image shown in FIG. 19A.

FIGS. 20A–20E are photographs showing a sequence of images where computer pattern filtering has been used to detect particles on a 150 millimeter patterned wafer according to the method shown in FIG. 18.

FIG. 21 is flow chart, which shows an example procedure for combining results from two or more image acquisition and analysis processes.

FIG. 22 is schematic illustration of a portion of an inspection module having a programmable LCD mask according to another alternative embodiment of the present invention.

DETAILED DESCRIPTION OF ILLUSTRATIVE EMBODIMENTS

1. Optical Inspection Module

Figure 9:
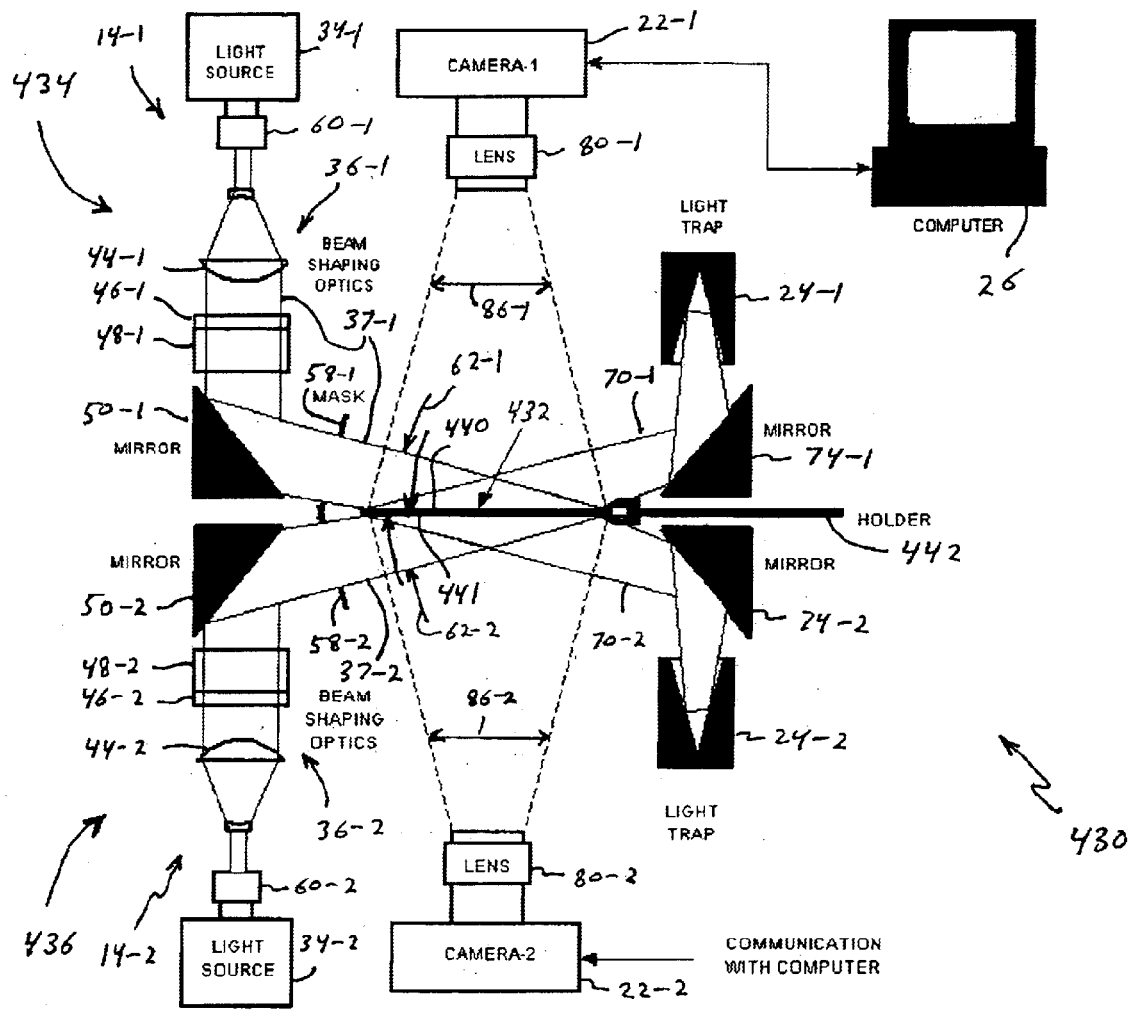
FIG. 9 is a schematic illustration of a dual surface defect inspection system, according to one embodiment of the present invention.

FIG. 1 is a schematic representation of a large area optical inspection module 10 according to one embodiment of the present invention. Inspection module 10 is useful for detecting particles and other defects on the front (e.g., active) side or back side of large patterned or un-patterned substrates such as semiconductor wafers, flat panel displays, magnetic recording discs and electronic packages substrates, for example. Inspection module 10 can also be modified or duplicated to inspect both the front side and back side of a substrate either simultaneously or sequentially, as described in more detail below with reference to FIGS. 9 and 10.

Inspection module 10 includes enclosure 12, illuminator 14, substrate holder 20, imaging camera 22, light trap 24 and computer controller 26. Enclosure 12 is preferably light-proof and has light-absorbing internal surfaces 30 for minimizing deleterious effects of internal and external stray light during inspection. In one embodiment, enclosure 12 forms a vacuum chamber, and the components internal to enclosure 12 are vacuum-compatible components. Enclosure 12 can have one or more walls 32 for forming compartments that optically and physically isolate various components of module 10. Enclosure 12 can further include an entrance, gate or door (not shown) through which substrates, such as substrate 33, are loaded into and unloaded out of enclosure 12.

Illuminator 14 is housed within a first compartment of enclosure 12. Illuminator 14 includes light source 34 and beam shaping and conditioning components 36 which define a light beam path 37. Beam shaping and conditioning components 36 include optical integrator mixer rod 38, baffle 39, cold mirror 40, aperture 42, lenses 44 and 46, stray light baffle 48, cold mirror 50, polarizing filter 52, band pass filter 54, wedge filter 56 and mask 58. Mirrors 40 and 50 are provided in the light beam path 37 so that beam conditioning components 36 can be arranged in a compact space to reduce the overall size of illuminator 14.

Depending on the application, different types of light sources 34 can be used. For inspection based on light scattering detection, monochromatic laser light may be used when it is necessary to minimize chromatic aberration in the imaging optics. In some cases, laser light is easier to collimate and its use also enables better discrimination between scattered light and external stray light by incorporating a narrow laser band pass filter into the path of the detected light. The laser band-pass filter transmits light only in the illuminating laser wavelength range while rejecting stray light in all other wavelengths. Laser light may also be advantageous for photo-luminescence measurements, as it is easier to reject the excitation light using a narrow band-stop filter, such as a holographic notch filter. Lasers also have a short warm-up time and generally have a long operational life, often greater than 10,000 hours. However, the use of lasers requires compliance with stringent safety regulations, and requires a greater degree of care in operation.

In one embodiment, light source 34 includes a broad-band light source such as an arc lamp or a flash lamp. For measurements in photo-luminescent mode, high pressure arc amps with a broad available excitation wavelength range offer greater output in the blue and UV wavelength range as compared to laser light sources. Arc lamps unfortunately have an output that tends to decay over time, and have a long warm-up time and relatively short life. Exceptions to these are the recently available high-pressure, short arc lamps designed for use in liquid crystal display projectors and similar devices. Flash lamps have the ability to produce more UV light (for photo-luminescence) and also permit intermittent operation, which extends operational life. Flash lamps also do not have warm-up time problems.

For example, light source 34 can include a high-pressure mercury or metal-halide short-arc lamp. The desirable characteristics of these types of lamps include high radiance, long life, and high color temperature. An example of such a lamp is the 100 Watt Phillips UHP lamp, which has a rated lifetime of 10,000 hours, an arc gap of 1.3 millimeters, and a color temperature of around 9,000 degrees Kelvin. Similar lamps are available from Osram, PEC Lamp Corp., and Ushio. Since the light output of these lamps is incoherent, they also avoid problems associated with laser sources when inspecting rough or patterned surfaces, such as speckle and bright diffraction patterns. These lamps also have high output in the low wavelength range (e.g., 400–500 nanometers), which is useful in obtaining high resolution images and in improving detection sensitivity. Furthermore, these lamps also output significant ultraviolet radiation and therefore enable operation in the fluorescent detection mode described in more detail below. For example, light output from a 100 Watt Phillips UHP Lamp is reported to be 25 Watts in the visible band and 6 Watts in the UV band.

Other types of light sources can also be used, such as a commercially available 75–300 Watt xenon arc lamp or a 50–250 Watt quarts tungsten halogen (QTH) lamp, which emits a collimated, one-inch or larger diameter circular light beam of uniform intensity.

Referring back to the figure, light source 34 has a light beam port 60, which is optically coupled to an input face of mixer rod 38. In one embodiment, light source 34 includes an integral elliptical reflector to efficiently collect and focus the emitted light. Alternatively, an integral parabolic reflector can be used to generate a collimated beam and then a condenser lens to focus the beam onto a small area. To reduce the transmission of heat into the illumination zone on substrate 33, the integral reflector preferably has a di-chroic cold mirror surface to selectively reflect a visible light component (with a wavelength range of 400–700 nanometers) as opposed to the infrared (IR) radiation at wavelengths greater than 700 nanometers. A hot mirror surface can be used in the light beam path 37 to further attenuate infrared radiation to acceptable levels. Cold mirrors 40 and 50 also attenuate IR radiation. One or more fans (not shown) can be used to provide convection cooling and maintain the illumination housing at a controlled temperature.

Mixer rod 38 collects and homogenizes the focused light beam emerging from light source 34. In one embodiment, the cross-section of mixer rod 38 (or clad glass rod) is rectangular. To maximize light beam throughput, mixer rod 38 has an aspect ratio approximately equal to that of the cross-section of the light beam that is projected on to the substrate being inspected. For example, when inspecting a 300 millimeter wafer which is illuminated at a 5 degree angle of incidence to the wafer surface, a mixer rod having a three millimeter thickness, a 33 millimeter width and a 66 millimeter length could be used, with an input face placed at the focal point of the output reflector in lamp 34. Mixer rod 38 can be replaced by alternative optical integrators such as lens arrays (a fly-eye lens) and holographic diffusers.

The light beam emerging from mixer rod 38 is passed to an anamorphic lens assembly through baffle 39, mirror 40 and aperture 42. The anamorphic lens assembly is formed by one or more cylindrical lenses 44, which further shape the light beam traveling along light beam path 37 so that the aspect ratio of the light beam cross-section is substantially close to a desired value. The diverging light beam exiting the anamorphic lens assembly is collimated using a second lens assembly 46. The second lens assembly 46 has a large aperture and can include a Fresnel lens, for example. Fresnel lens 46 can be replaced by other lenses, such as a full-aperture cylindrical lens in alternative embodiments.

In order to prevent stray light from reaching substrate 33, illuminator 14 includes one or more stray light baffles 48. In one embodiment, stray light baffle 48 has a honeycomb structure with optically absorbing surfaces, which are aligned with light beam path 37 so as to trap stray light without substantially hindering the passage of collimated light. The light beam exiting stray light baffle 48 is passed to cold mirror 50, which projects the light beam onto an upper surface of substrate 33 through filters 52, 54 and 56 and mask 58. In one embodiment, the light beam illuminates substantially the entire upper surface of substrate 33 and is oriented to form a grazing angle of incidence 62 relative to the upper surface of substrate 33. A grazing angle of incidence is defined as an incidence angle between zero degrees and ten degrees from a vector parallel to the upper surface of substrate 33. The final collimating elements (lens 46 and mirror 50) can be replaced by a parabolic or spherical reflector in alternative embodiments.

Polarizing filter 52 polarizes the light beam, while band-pass filter 54 limits the wavelength range of the illuminating light. A variable density "wedge" filter 54 compensates for uneven distribution of incident light on substrate 33. When the substrate to be inspected is circular, such as in the case of a semiconductor wafer, a mask 58 with an elliptical aperture is used to illuminate the wafer. To minimize the deleterious effects of stray light, it is preferred that the illuminating beam be shaped so that only the substrate surface (and edges if desired) is illuminated. For example, in the case of 300 millimeter semiconductor wafer being illuminated at a 5 degree angle of incidence to the surface, the collimated beam from illuminator 14 can have a cross-section in the shape of an ellipse with dimensions of approximately 300 millimeters by 26 millimeters, corresponding to an aspect ratio of 11.5:1. Illuminator 14 can include various other beam-shaping optics in various arrangements in alternative embodiments of the present invention. The illumination scheme shown in FIG. 1 could also be used in a photo-luminescence mode. In this mode, ultraviolet (UV) cold mirrors would be used in place of visible light mirrors 40 and 50.

In addition, the light beam and the light beam path can have various other shapes and angles of incidence relative to substrate 33 in alternative embodiments of the present invention. For example, the light beam can be collimated, non-collimated and can be generated by an active source or a passive source. The term active source refers to a primary light source, which actively generates light through an energy conversion process, whereas the term passive light source refers to source, which emits light by specular or diffuse reflection. The light beam path can be oriented at a grazing angle or a non-grazing, larger angle of incidence for acquiring images in a brightfield mode, as opposed to a darkfield mode. The light beam path can also be oriented normal to substrate 33. In one embodiment, illuminator 14 is replaced with a conical beam source positioned above substrate 33 an illuminating the entire substrate. Alternatively, a uniformly illuminated white panel can be placed in the background, with camera 22 imaging substrate 33 from an angle not normal to the substrate surface. The camera image includes the substrate pattern superimposed on the reflected white background. This method effectively produces a bright field image free of diffraction.

In the embodiment shown in FIG. 1, as the light beam from light source 34 reflects off of the active surface of substrate 33 particles or other surface defects residing on the active surface scatter light from the light beam path. The scattered light from the active surface is referred to as non-specularly reflected light. The intensity of the scattered light due to a defect is a function of the size of the defect.

Specularly reflected light 70 is trapped by light trap 24. In one embodiment, light trap 24 is contained in a separate compartment than substrate 33. A window 72 transmits the specularly reflected light 70 through enclosure wall 32 to mirror 74, which directs the light toward light trap 24. Light trap 24 has light absorbing surfaces (optical baffles). The inside surfaces 75 surrounding light trap 24 are also provided with light absorbing surfaces to trap stray light from the substrate being inspected.

Camera 22 is supported above substrate 33 and is oriented to acquire images of the non-specularly reflected light that is scattered from particles and other defects and features on the active surface of substrate 33. Camera 22 preferably has a variable exposure to enable the detection to be optimized with respect to particle size and surface conditions. In one embodiment, camera 22 includes a scientific grade, slow-scan, cooled CCD camera, such as a commercially available Photometrics Model Sensys 1400 series camera, which is operated in a high signal-to-noise mode for detection of weak signals on bright backgrounds. Cooled CCD cameras have an active cooling device, such as a thermoelectric cooling device, for cooling the photodetector array. Cooled CCD cameras have lower dark current. Slow-scan CCD cameras have image readout times that are much slower than video cameras, such as 0.1 frames per second to 10 frames per second, depending on the size of the photodetector array. Slow-scan CCD cameras also do not need to operate continuously, and inspection module 10 can therefore acquire snapshot images on command. Slow-scan CCD cameras have low read-out noise. In an alternative embodiment, camera 22 includes a video camera. Conventional video cameras produce images at 30 frames/second, and operate in a continuous mode.

Camera 22 includes a lens 80 and an internal charge-coupled device photodetector array 81. Lens 80 collects a fraction of the light scattered from the active surface of substrate 33 and applies the collected, scattered light to photodetector array 81. Lens 80 can include a commercially available high resolution camera lens for providing adequate light collection for the selected spatial resolution, such as a Navitar model DO-1213 CCTV lens with an aperture of F/1.3 and a focal length of 12.5 mm. Lenses with variable magnification ranges may be used to image differently sized substrates. One or more optional filters 82 can be positioned between lens 80 and the surface of substrate 33.

Photodetector array 81 defines an image plane 84 for camera 22, which lies within a focal plane of lens 80. The term "focal plane" refers to the surface (plane) on which an image transmitted by lens 80 is brought to sharp focus. Photodetector array 81 is divided into a plurality of pixels, with each pixel corresponding to a unit area on the active surface of substrate 33. The plurality of pixels together have a field of view 86 which covers substantially the entire active surface of substrate 33. A large photodetector array is desired for good spatial resolution. In one embodiment, photodetector array 81 includes an array of 1024 by 1024 pixels, wherein each pixel has an area of 24 µm by 24 µm on the photodetector array.

Camera 22 also includes digitizing and computer interfacing circuitry in which the light intensities detected within each pixel of the photodetector array are converted to form a grey level image. The grey level image is coded in a standard format, such as an 8-bit or 16-bit TIFF format, which is provided to output 90. Output 90 can include an 8-bit, 12-bit or 16-bit output, for example. A 12-bit output provides a high definition image with a 4096 grey level image depth. A 16-bit output provides a 65,536 grey level image depth.

In one embodiment, computer controller 26 preferably includes an microprocessor-based workstation having standard communications interfaces 92 and 94. Interface 92 is coupled to output 90 to enable computer controller 26 to communicate with camera 22. Interface 92 can include an RS 232 or an IEEE 488 interface, for example. Interface 94 can include an SECS interface, for example, to enable computer controller 26 to communicate with other computers in a multi-process cluster tool system. The information communicated to the other computers can include inspection status, inspection data, analysis results, a pass/fail signal or test scheduling information for example. Computer controller 26 can also include an interface 96 for controlling light source 34. Additional interfaces can also be included for controlling any transport arms for loading and unloading each substrate 33 into and out of module 10.

Computer controller 26 is provided with software drivers for controlling the operation of camera 22, communicating with other computers and analyzing images acquired by camera 22. All software is stored in a computer-readable medium-such as a hard disc drive, a CD-ROM, a floppy disc, or random access memory, which is associated with computer controller 26. During inspection, the images acquired by camera 20 are processed by computer controller 26 to identify and count particles and other defects, such as scratches, stains, residue, fingerprints and pits. Computer controller 26 can be used to control a single inspection module or multiple inspection modules at the same time. During operation, camera 22 captures images of substrate 33 while the substrate is illuminated by light source 34 at a grazing angle of incidence. These images are analyzed by computer controller 26 to determine the number and location of particles and other defects on the active surface. The presence of particles and other defects and features within each unit area of substrate 33 is identified as a function of the measured intensity within the corresponding pixel in the photodetector array. In one embodiment, the measured intensity, or grey level value, within each pixel is compared with an intensity threshold. This allows light scattering caused by particles to be distinguished from light scattering caused by surface roughness or other background features. Each pixel having a measured intensity that exceeds the intensity threshold corresponds to an area on substrate 33 having a particle or other defect or feature. A list of particle or defect locations on substrate 33 is generated based on the location of each of these pixels relative to the other pixels in photodetector array 81. Multiple intensity threshold levels can also be used.

A count of the total number of particles residing on the active surface of substrate 33 is generated based on a count of the number of pixels having a measured intensity that exceeds the intensity threshold. In one embodiment, groups of these pixels that are spatially contiguous with one another in photodetector array 81 are considered as representing a single defect or feature on the active surface. The shape of the defect or feature can be analyzed to classify the type or source of the defect, such as a particle, a stain, a fingerprint or a scratch, or the type of feature.

FIG. 2 is histogram illustrating an example of the number of pixels in an image of substrate 33 as a function of grey level value for the case of an un-patterned wafer. Line 110 represents an intensity threshold. Pixels having a grey level value above intensity threshold 110 are activated by light scattered from particles (or other surface features) above a predetermined size. Pixels having a grey level value below intensity threshold 110 are activated by light scattered from particles or surface roughness below the predetermined size.

Image enhancement techniques may be used to obtain the highest sensitivity to particles and detects for particular applications.

Referring back to FIG. 1, inspection module 10 can further include an additional brightfield illumination source (not shown), which generates a light beam that is oriented substantially at a non-grazing angle of incidence to the active surface of substrate 33 and illuminates substantially the entire active surface, in an alternative embodiment. Specularly reflected light from the surface of substrate 33 from the brightfield illumination source is then collected by lens 80 and applied to photodetector array 81 within camera 22. The image acquired under brightfield illumination can be analyzed by computer 26 to detect the perimeter and orientation of substrate 33 by using edge detection software, for example.

2. Alternative Illumination Arrangement

FIG. 3 is a schematic representation of a large area optical inspection module 150 according to an alternative embodiment of the present invention. The same references numerals are used in FIG. 3 as were used in FIG. 1 for the same or similar elements. Inspection module 150 is essentially the same as inspection module 10, but includes an alternative illuminator 152.

Illuminator 152 includes a high-pressure short-arc lamp 154 with in integral elliptical reflector, a cold mirror 156, a mixer rod 158, a projector lens 160, a cold mirror 162, stray light baffles 164 and 166, a cold mirror 168, a polarizing filter 52, a band-pass filter 54, a wedge filter 56 and a mask 58. These components are arranged to form a light beam path 170 from arc lamp 154 to the surface of substrate 33 for illuminating substantially the entire area of the substrate at a grazing angle of incidence. Once again, mixer rod 158 is an optical integrator used to collect and homogenize the output of lamp 154, while multiple cold mirrors 156, 162 and 168 are used to "steer" the beam and attenuate the infra-red component of the emitted light.

Projector lens 160 is a "relay" lens that projects an image at the output face of mixer rod 158 onto substrate 33. Projector lens 160 can include a commercially available camera lens, such as an f/2 100 millimeter focal length lens designed for 35 mm format cameras, with an added plano-convex element preceding the lens to provide telecentric light collection. A suitable camera lens can include a six-element double Gauss relay lens, for example. Such telecentric light collection achieves efficient collection of light emerging from mixer rod 158. A spherical mirror (not shown) could be used to collimate the diverging beam if necessary. As in the embodiment shown in FIG. 1, stray light baffles 164 and 166, mask 58 and filters 52, 54 and 56 are placed in light beam path 170 to suitably condition and shape the beam.

3. Measurement of De-Polarized Scattered Light

The optical inspection modules shown in FIGS. 1 and 3 can be adapted to measure depolarized light scattered from the substrate surface, which can be advantageously used to inspect patterned wafers having high background scattering levels. Referring back to FIG. 1, filter 82 is replaced with a cross-coupled polarizing filter (analyzer). Polarizing filter 52 in illuminator 14 is placed in the illumination light beam path to linearly polarize the light beam that is incident on the substrate surface. Defects on the substrate surface alter the polarization state of the reflected/scattered light, and are detected with high contrast using cross-coupled polarization filter 82. In one embodiment, the polarization axis of filter 82 is perpendicular to that of polarizing filter 52. Filter 82 transmits the depolarized light from defects, while attenuating the polarized light from the background surface. In one embodiment, polarizing filter 52 illuminates substrate 33 with s-polarized light, while filter 82 enables detection of p-polarized light.

FIGS. 4A–4C show example results obtained by inspecting a patterned wafer through depolarized light with an optical inspection module such as that shown in FIG. 1. While the entire surface of substrate 33 was imaged, FIGS. 4A–4C show only a small portion of the image. In each image, a patterned wafer was illuminated by linearly polarized light. FIG. 4A is an image of the wafer taken without cross-polarizing filter 82 in the detection beam path. FIG. 4B is an image of the wafer taken with cross-polarizing filter 82 in the detection beam path. The image shown in FIG. 4C represents the image shown in FIG. 4B after being filtered by a two-stage computerized filtering process to highlight defects with respect to the background. It is seen that the detection of depolarized light (the image shown in FIG. 4B) improves the contrast between defects and background.

4. Measurement of Photo-Luminescent Light

Photo-luminescence measurements, including molecular fluorescence and phosphorescence, have been used for analysis of chemical compounds and other materials. Fluorescence measurements have been used in the semiconductor industry for particle contamination and defect detection, for measurement of critical dimensions, for film thickness measurements, for end-point detection and for etch rate measurements.

The optical inspection modules shown in FIGS. 1 and 3 can be adapted for making photo-luminescence measurements while imaging the entire wafer at one time. These measurements can be used for inspecting semiconductor wafers for the presence of contaminants such as photo-resist residue, skin flakes, fiber from clothes, and flakes of polymeric dielectric materials such as polyimids, etc. Such contaminants emit longer wavelength fluorescent light when irradiated with ultraviolet light (having wavelengths less than 400 nanometers) or with blue or green light (having wavelengths of 400–520 nanometers). For example, module 250 can be used to inspect a wafer for residual photo-resist after an oxygen plasma ashing operation.

For making photo-luminescence measurements, light source 34 can include any light source, such as an arc lamp, that is capable of emitting light in the UV wavelength range. In an alternative embodiment, a "line source" such as a fluorescent tube (e.g., a germicidal lamp) or a linear flash tube fitted with a parabolic reflector is used to produce a beam with a substantially rectangular cross-section. Light source 34 can alternatively include a laser with suitable collimating optics to produce a light sheet with a rectangular cross-section.

Polarizing filter 52 is removed, and band-pass filter 54 is adapted to transmit excitation light within a selected wavelength range (such as in the range 250–500 nanometers), that contains wavelengths known to excite fluorescence from a broad range of organic materials including for example, specific photo-resists. The incident UV light excites fluorescent emission in the visible wavelength range from selected organic compounds on the wafer surface, and a portion of the emitted light is collected by camera 22. Specifically, these organic compounds absorb energy from the excitation light and emit photons of lower energy in a different wavelength range than the excitation light.

To distinguish the fluorescent light emission from scattered light, filter 82 is replaced with a long pass filter, which blocks substantially all non-fluorescent light. In one embodiment, long pass filter 82 has a cut-on frequency above 500 nanometers. If a laser light source is used, long pass filter 82 may be replaced by a holographic notch filter to reject the scattered laser light and transmit only the fluorescent light. For flexibility, inspection module 10 may also be provided with multiple sets of excitation and emission filters optimized for fluorescence measurements with specific target materials. Such filter sets may be obtained commercially, for example from Spindler and Hoyer, Inc. of Milford, Mass.

To prevent stray light or artifacts from influencing camera 22, enclosure 12 preferably has non-fluorescing surfaces, and is constructed using components made of non-fluorescing materials. Since the background fluorescence emission is then essentially zero, this technique provides a very sensitive technique for detecting organic contaminants on the surface of the substrate being inspected, with the entire wafer surface being imaged at one time.

In one embodiment, a variety of different types of filters 52, 54 and 82 are physically moved into and out of the illumination and detection paths to switch between a variety of different modes of operation. For example, module 10 can be operated to detect i) unpolarized light scattering; ii) cross-polarized light scattering; and iii) flourescence. The filters can be moved manually by an operator or automatically under the control of process controller 26. Also, one or more images can be taken in each operating mode and can be later combined or compared by software to enhance detection or analysis.

5. Operation in Off-Axis (Scheimpflug) Imaging Mode

In the embodiments discussed above, the optical axis of the camera lens is normal to the image plane of the camera, and also to the object plane on the substrate surface. In an alternative embodiment, the camera is arranged in a Scheimpflug imaging mode, where the camera lens axis is not normal to the substrate plane. Rather, the lens axis is oriented at an oblique angle to the substrate surface. In this configuration, the entire substrate can be illuminated at any angle of incidence to the substrate, and the incident light beam can be collimated or not collimated. Also, the illumination source can be passive or active. The camera lens can be positioned relative to the substrate to collect forward scattered light, backward scattered light, or side scattered light while avoiding the specularly reflected light.

FIG. 5A schematically illustrates a simplified optical inspection module 260, which is configured for detection of an active surface 272 of a substrate 270 at an oblique angle. Substrate surface 272 defines an object plane 274. Module 260 includes a camera 276, a lens 278 and additional components such as those shown and discussed with respect to the previous figures for illuminating substrate surface 272 and imaging light scattered from the surface.

Camera 276 has an image plane 280, which is not parallel to object plane 274 as in the previous figures. In the embodiment shown in FIG. 5A, image plane 280 is substantially perpendicular to object plane 274. Other angles can be used in alternative embodiments. Lens 278 has an optical axis 279, which is oriented at an oblique angle 281 relative to object plane 274. As a result, lens plane 282 is not parallel to object plane 274. Lens plane 282 is tilted relative to image plane 280 so that the entire substrate surface 272 remains in focus on image plane 280. This allows the use of a wide aperture imaging lens with high light collecting ability despite having a small depth of field. In this configuration, object plane 274, image plane 280 and lens plane 282 all intersect along a line going into the page in FIG. 5A, at point 284. Oblique angle 281 can be any oblique angle, such as 40–45 degrees from the substrate surface. In one embodiment, the illuminating light beam (not shown in FIG. 5A) is oriented at a grazing angle of incidence relative to substrate surface 272.

FIG. 5B is a simplified schematic illustration of module 260 as viewed from a direction normal to substrate surface 272, which defines the object plane 274. Arrow 285 schematically represents the illuminating light beam and its directional component in object plane 274. Camera 276 and lens 278 are oriented at an angle relative to the directional component of light beam 285 within object plane 274. The optical axis 279 of lens 278 is oriented at a non-zero azimuthal angle 286 to the directional component of light beam 285 relative to object plane 274. When module 260 is configured in a "dark-field" imaging mode, any azimuthal angle 286 can be used as long as lens 278 avoids collection of specularly reflected light. The azimuthal angle 286 can be set to collect forward scattered light (less than +/−90 degrees), backward scattered light (greater than +/−90 degrees), or side-scattered light (at about 90 degrees) while avoiding the specularly reflected light.

Example configurations for inspecting 200 millimeter and 300 millimeter diameter semiconductor wafers using the off-axis Scheimpflug imaging mode shown in FIGS. 5A and 5B are given below in Table 1.

TABLE 1

| Wafer Size, mm | Camera or CCD chip | CCD chip Resolution | Lens Focal Length and Aperture | Nominal Magnification | Working Distance | Angle From Normal |
| --- | --- | --- | --- | --- | --- | --- |
| 200 | Sensys 1400 | 1315 × 1035 | Navitar 12.5 mm F1.3 | 1/23 | 30 cm | 50° |
| 200 | Sensys 1600 | 1536 × 1024 | Navitar 12.5 mm F1.3 | 1/16.7 | 30 cm | 45° |
| 300 | Sensys 1600 | 1536 × 1024 | Navitar 12.5 mm F1.3 | 1/25 | 32.5 cm | 40° |
| 300 | Kodak KAF-6300 | 3072 × 2048 | Nikkor 28 mm F1.4 | 1/12 | 36.5 cm | 40° |

Off-axis imaging enables higher sensitivity when inspecting microelectronic substrates with high levels of background scattering. Such a configuration can also be used in an integrated metrology system when optical access to the substrate is only possible from an oblique view, such as from a window on the side wall of a process chamber. In the case of rectangular format imaging detectors, it enables a greater fraction of the detector surface area to be used for imaging the active surface of the substrate. It should be noted that the image shape is distorted when operating in this imaging mode, and coordinate transformations should be used to map defects accurately.

The off-axis imaging configuration shown in FIGS. 5A and 5B enables better signal-to-noise performance analogous to that achieved by so called "double-dark field" detection configurations used in prior art laser wafer scanners. In these scanners, a small laser spot is raster scanned across the wafer surface. A single photodetector detects the scattered light at an oblique angle. These scanners are not capable of imaging the entire active surface at one time. Rather, only a small portion of the wafer is illuminated at a time, therefore requiring the wafer to move relative to the illuminator beam to enable the entire surface to be inspected. In the embodiment shown in FIGS. 5A and 5B, the entire active surface is imaged at one time, with the entire active surface remaining in focus on the image plane 280. This provides a significant increase in efficiency and sensitivity of the inspection module.

In an alternative embodiment of the present invention, lens axis 279 (shown in FIG. 5A) is oriented at an oblique imaging angle relative substrate surface 272 while the substrate is illuminated at a relatively large angle of incidence, such as substantially normal to the substrate surface. For example, substrate surface 272 can be illuminated from above (at any angle) with a conical beam eminating from a point source while imaging in an off-axis mode to avoid specular reflection into camera 276.

In another alternative embodiment, shown schematically in FIG. 5C, inspection module 260 includes a uniformly illuminated white panel 288, which is placed to the side of substrate, opposite to lens 278. Lens 278 and camera 276 image substrate 270 from an angle not normal to the substrate surface. In this example, panel 288 is oriented perpendicular to substrate surface 272 and emits diffuse light 289 that illuminates the entire substrate surface 272. The image acquired by camera 276 includes the substrate pattern superimposed on the reflected white background from panel 288. This method effectively produces a bright field image free of diffraction from substrate surface 272.

In yet another alternative embodiment shown in FIG. 5D, optical inspection module 260 includes a plurality of detectors, wherein each detector has an optical lens axis that is not perpendicular to the object plane. The same reference numerals are used in FIG. 5D as were used in FIG. 5A for the same or similar elements. Module 260 has an additional CCD camera 290 having an image plane 292 and an additional lens 294 having a lens plane 296, which is tilted relative to image plane 292. Image plane 292, lens plane 296 and object plane 274 intersect along a line going into the page in FIG. 5D at point 298. Lens 294 has an optical axis 297, which is oriented at an oblique angle relative to substrate surface 272. The optical axis 297 of lens 294 is also oriented at a non-zero azimuthal angle to the directional component of the illuminating light beam relative to object plane 274, similar to that shown in FIG. 5B for camera 276 but at a different azimuthal angle. This angle can be set to collect forward scattered light, backward scattered light, or side-scattered light while avoiding the specularly reflected light. In an alternative embodiment, the second camera 290 and lens 294 are positioned on-axis, above substrate 270, similar to camera 22 and lens 80 shown in FIG. 1.

The use of two or more detectors allows the entire active surface of substrate 270 to be imaged at one time from two or more different angles. The plurality of images can then be used to further enhance the detection software. One advantage of acquiring images at different angles is that the images may allow for differentiation between scratches and pits from surface defects. Another advantage is that scratches might show up in the acquired image in one imaging direction but not in another due to the directionality of the scattering signal. Also, the diffraction hot spot problem discussed below with respect to inspection of patterned wafers can be solved by imaging the wafer at several different angles. Regardless of the detector setup, each imaging angle produces a unique view of the surface for patterned wafers. The good image data from the images acquired from the different angles can then be stitched together in software to form a combined image that is free of diffraction hot spots caused by the background wafer pattern. In addition, to cameras 276 and 290, a further camera such as those shown in FIGS. 1 and 3 can be used, which have an image plane and a lens plane that are parallel to the object plane. The use of two or more images at different angles also enables improved false defect count rejection and on-the-fly defect characterization by using combinations or comparisons of the multiple images.

In yet another alternative embodiment, one or more off-axis detectors such as those shown in FIGS. 5A–5D can be used while rotating substrate 270 about an axis 299 relative to the light beam path and the detectors. As substrate 270 is rotated about axis 299, images are collected from the camera (or cameras) at each substrate position. This can further enhance the ability of the inspection module to detect light scattered from particles and other defects on the substrate surface relative to background scattering and can enhance the ability to classify the defects. In addition, rotation of substrate 270 can be used to achieve a desired substrate orientation. For example, an image of substrate 270 can be taken (on-axis or off-axis) to measure its rotational orientation. Substrate 270 is then rotated to the desired orientation and another image (on-axis or off-axis) is taken for defect measurement and detection.

Alternatively, substrate 270 can remain fixed and the position of the camera (or cameras) can rotate about axis 299. As the camera (or cameras) is rotated about axis 299, images are collected from the camera (or cameras) at each camera position. This has the additional effect of moving the detection angle relative to the direction of illumination.

6. In-Line Wafer Inspection

In addition to the use of the optical inspection module as a stand-alone wafer inspection tool, the high throughput and compact footprint of the module make it ideal for use as an in-line wafer inspection device for cluster tools. U.S. Pat. No. 5,909,276 to Kinney et al. discloses a wafer inspection module, which is integrated as one of several processing modules in a multi-process "cluster tool" system. A cluster tool is a manufacturing system that includes a set of environmentally isolated process chambers or modules, which are linked by a material handling interface and a computer communications interface. The material handling interface transports a workpiece between the various modules in the system. The computer communications interface controls the sequential steps. Clustering multiple operations within a single manufacturing system leads to benefits such as increased process yield (due to less wafer handling and improved process control) and reduced process cycle time. There are several types of clustering systems, such as vacuum cluster tools for deposition and etching, lithography tools, chemical-mechanical polishing systems, and ion implant tools, etc. While each of these tools may have widely differing arrangements, they are collectively referred to as "cluster tools" within the present specification and claims.

Integrating an inspection module as one of several processing modules in a cluster tool system could require different mechanical, electrical, computer communications and software interfaces for each unique cluster tool system. The customization associated with such an integration approach increases developed costs when integrating the module into a wide range of cluster tools made by different original equipment manufacturing (OEM) vendors.

In one embodiment of the present invention, these difficulties are avoided by integrating the inspection module at the wafer load/unload port of the cluster tool. The semiconductor equipment industry, for example, has evolved standard wafer loading/unloading modules, which are commonly used by most OEM vendors in their equipment. One example of such a standard is the "front-end" wafer handling systems based on the SEMI standard front opening unified pod (FOUP) carrier for 300 millimeter wafers. Another example is the standard mechanical interface (SMIF) system.

FIG. 6 is a schematic illustration of a multi-process cluster tool system 300 in which an inspection module 302 has been integrated. Cluster tool system 300 includes a wafer loading/unloading module 304 with load/unload ports 305 and 306. In one embodiment, inspection module 302 is "docked" at load/unload port 305, and a standard front opening unified pod (FOUP) 308 is "docked" at load/unload port 306. Pod 308 holds a plurality of wafers in horizontally oriented slots to be loaded into or unloaded out of cluster tool system 300. Wafer loading/unloading module 304 includes a wafer handling robot for transporting individual wafers to and from ports 305 and 306 and load lock chambers 310 and 312 of cluster tool system 300.

Cluster tool system 300 further includes a plurality of substrate processing stations 314–317. Each process station 314–317 has a process chamber entrance 318 for providing access to the respective process station. A common material transport arm 320 interfaces with load lock chambers 310 and 312 and process stations 314–317 along a predefined substrate travel path. In FIG. 6, transport arm 320 is shown transporting a substrate 322 into process station 316. Cluster tool controller 324 controls cluster tool system 300 and its transport arm 320. Controller 324 also controls the wafer handling robot within module 304 and communicates with optical inspection module 302 to schedule an inspection step in the overall process sequence determined by controller 324.

Inspection module 302 has an entrance 330 through its enclosure, which communicates with wafer load/unload port 305 to allow access by the wafer handling robot within module 304. For example, entrance 330 is configured consistently with a standard wafer mechanical and electrical handling interface, such as the FOUP or the SMIF interfaces. Since inspection module 302 holds only a single wafer at the inspection position at a time, module 302 is configured to appear to the wafer handling robot within module 304 as having only a single empty "slot" into which the wafer to be inspected may be placed. Other equivalent approaches could also be used in integrating an optical inspection module into a wafer load/unload system. One general approach is to integrate the optical inspection module as a dedicated wafer inspection station into a wafer load/unload port as shown in FIG. 6.

FIG. 7 is a schematic illustration of inspection module 300, which shows the insertion of substrate 322 by the wafer handling robot of wafer load/unload module 304 shown in FIG. 6. Inspection module 300 includes enclosure 350, illuminator 352, illumination light beam path 354, light trap 356, detector 358 and computer controller 360. Wafer handling robot arm 362 has a retracted position 364 (shown in phantom) relative to inspection module 300 in which substrate 322 is positioned external to enclosure 350. Robot arm 362 has an extended position 366 in which substrate 322 is positioned internal to enclosure 350. In extended position 366, robot arm 362 extends through entrance 330 and supports substrate 322 at a predetermined substrate holding position relative to light beam path 354 and detector 358 during the inspection process. A separate holder, such as holder 20 shown in FIG. 1 can be used in alternative embodiments. The substrate holding position is viewed by robot arm 362 as a single empty "slot" into which substrate 322 may be placed. As in the previous embodiments, illuminating light beam path 354 illuminates substantially the entire active surface of substrate 322 at a grazing or non-grazing angle of incidence. Detector 358 has a field of view, which is capable of imaging substantially the entire active surface of substrate 322 at one time. Detector 358 can have an optical axis that is either normal to the substrate surface or at an oblique angle relative to the substrate surface.

7. Inspection Module with Multi-Measurement Function

When processing semiconductor wafers and similar micro-electronic substrates, it is often useful to monitor more than one variable relating to the substrate being processed. For example, during a chemical vapor deposition (CVD) process for depositing a thin film of dielectric or metal on a semiconductor wafer, it may be advantageous to monitor film parameters such as thickness, refractive index, resistivity and stress, in addition to the number of particles on the wafer being processed. In integrated metrology applications, since the available area within a cluster tool is limited, it is advantageous to provide a capability for multiple integrated metrology within a single compact platform. The platform can be configured as a stand-alone system or as one of the processing stations in a cluster tool such as that shown in FIG. 6.

FIG. 8 is a schematic illustration of an integrated metrology station 400 according to one embodiment of the present invention. Similar to the previous embodiments, station 400 includes an enclosure 402, a light source and beam shaping objects 404, an illumination light beam path 406, a substrate holder 408, a large array, cooled CCD camera 410, a light trap 412 and a computer controller 414. Illumination light beam path 406 illuminates substantially the entire surface of a wafer 416 at one time, and camera 410 has a field of view 418 which is capable of imaging the substantially the entire surface of substrate 416 at one time.

In addition, station 400 includes a second instrument 420, such as a film metrology head or microscope, which enables measurement station 400 one or more measurements in addition to defect detection, such as detect review and film property measurements. Film metrology head or microscope 420 is mounted on an X-Y (or r-θ) stage 422, for example, which positions the sensor over the substrate 416 being measured. Station 400 is preferably provided with a transparent window (not shown) placed over substrate 416 to protect the substrate from particle contamination generated by motion of the X-Y stage 422. When the film metrology head or microscope 420 is not being used, it can be positioned out of the field of view 418 of camera 410. This configuration permits both defect detection and film property measurements to be independently performed. In one embodiment, the film metrology head or microscope 420 measures film properties using a spectral reflectance technique. The film metrology head can also incorporate a microscope, so that it can be used for defect review and mapping in addition to film property measurements.

8. Dual Surface Defect Inspection System

FIG. 9 is a schematic illustration of a dual surface defect inspection system 430 according to one embodiment of the present invention. Inspection system 430 is capable of inspecting both the front and back surfaces of a substrate 432 simultaneously or sequentially. Inspection system 430 is an extension of the single surface inspection tools shown in FIGS. 1, 3, 5A–5D, 7 and 8. Inspection system 430 includes a first measurement instrument 434 for inspecting a front (e.g., active) surface 440 of substrate 432 and a second measurement instrument 436 for inspecting a back surface 441 of substrate 432. Measurement instruments 434 and 436 can include any one or a combination of the inspection tools shown in FIGS. 1, 3, 5a–5d, 7 and 8, for example. In the example shown in FIG. 9, both measurement instruments 434 and 436 are similar to the inspection module 10 shown in FIG. 1 for inspecting surfaces 440 and 441 at a grazing angle of incidence where substantially the entire surfaces 440 and 441 are illuminated and imaged at one time. The same reference numerals are used in FIG. 9 as were used in FIG. 1 for the same or similar elements.

Measurement instrument 434 includes an illuminator 14-1, which includes light source 34-1 and beam shaping and conditioning components 36-1 that define an illumination light beam path 37-1 extending from light source 34-1 to the front surface 440 of substrate 432. Among other elements, beam shaping and conditioning components 36-1 can include lenses 44-1 and 46-1, light baffle 48-1, mirror 50-1 and mask 58-1, for example. A variety of other beam shaping elements and arrangements can also be used.

Light source 34-1 includes a light beam port 60-1, which is optically coupled to light beam path 37-1. The light beam exiting port 60-1 is passed to mirror 50-1, which projects the light beam onto front surface 440 through mask 58-1. In one embodiment, the light beam in path 37-1 illuminates substantially the entire front surface 440 and is oriented to form a grazing angle of incidence 62-1 relative to front surface 440. In an alternative embodiment, light beam path 37-1 illuminates only a portion of front surface 440, and one or both of the light beam path 37-1 and substrate 432 are rotated or otherwise moved to scan front surface 440.

In addition, the light beam and the light beam path 37-1 can have various other shapes and angles of incidence relative to front surface 440 in alternative embodiments of the present invention. For example, the light beam can be collimated, non-collimated and can be generated by an active source or a passive source. Light beam path 37-1 can be oriented at a grazing angle or a non-grazing angle of incidence for acquiring images in a darkfield mode or a brightfield mode. Light beam path 37-1 can also be oriented to normal to substrate 432.

In the embodiment shown in FIG. 9 as the light beam from light source 34-1 reflects off of front surface 440, mirror 74-1 directs specularly reflected light 70-1 into light trap 24-1. Particles or other surface defects residing on surface 440 scatter light from light beam path 37-1. The scattered light from front surface 440 is referred to as non-specularly reflected light.

Camera 22-1 is supported above front surface 440 and is oriented to acquire images of the non-specularly reflected light that is scattered from particles and other defects and features on front surface 440. Camera 22-1 can include any one of a variety of different types of cameras, such as those discussed above. Camera 22-1 includes a lens 80-1, which collects a fraction of the light scattered from front surface 440 and applies the collected scattered light to the photodetector array 81 (shown in FIG. 1) within camera 22-1. Again, the photodetector array in camera 22-1 defines an image plane for camera 22-1, which lies within a focal plane of lens 80-1. The photodetector array is divided into a plurality of pixels, which each pixel corresponding to a unit area on front surface 440. The plurality of pixels together have a field of view 86-1, which covers substantially the entire front surface 440. In an alternative embodiment, field of view 86-1 covers only a portion of front surface 440 and is scanned along front surface 440 with illumination path 37-1. The images collected by camera 22-1 are passed to computer controller 26 for analysis as discussed above. In embodiments where the first measurement instrument 434 illuminates only a portion of front surface 440, and scans the front surface by rotating or otherwise moving substrate 432, such as with a laser wafer scanner, the scattered light can be collected by suitable optics and detected by a suitable a non-imaging photodetector, such as a photomultiplier or a photodiode, for example. The photodetector has at least one element or pixel that is positioned in a focal plane or focal point of the optics that collects the scattered light. Similarly, the second measurement instrument 436 includes an illuminator 14-2, which includes light source 34-2 and beam shaping and conditioning components 36-2 that define an illumination light beam path 37-2 extending from light source 34-2 to the back surface 441 of substrate 432. A variety of beam shaping elements and arrangements can be used.

Light source 34-1 includes a light beam port 60-2, which is optically coupled to light beam path 37-2. The light beam exiting port 60-2 is passed to mirror 50-2, which projects the light beam onto back surface 441 through mask 58-2. In one embodiment, the light beam in path 37-2 illuminates substantially the entire back surface 441 and is oriented to form a grazing angle of incidence 62-2 relative to back surface 440. In an alternative embodiment, light beam path 37-2 illuminates only a portion of back surface 441, and one or both of the light beam path 37-2 and substrate 432 are rotated or otherwise moved to scan back surface 440.

The light beam in path 37-2 can be collimated, non-collimated and can be generated by an active source or a passive source. Light beam path 37-2 can be oriented at a grazing angle or a non-grazing angle of incidence for acquiring images in a darkfield mode or a brightfield mode. Light beam path 37-2 can also be oriented to normal to substrate 432.

As the light beam from light source 34-2 reflects off of back surface 441, mirror 74-2 directs specularly reflected light 70-2 into light trap 24-2. Particles or other surface defects and features residing on surface 441 scatter light from light beam path 37-2.

Camera 22-2 is supported below back surface 441 and is oriented to acquire images of the non-specularly reflected light that is scattered from particles and other defects and features on back surface 441. Camera 22-2 can include any one of a variety of different types of cameras, such as those discussed above. Camera 22-2 includes a lens 80-2, which collects a fraction of the light scattered from back surface 441 and applies the collected scattered light to the photodetector array 81 (shown in FIG. 1) within camera 22-2. Again, the photodetector array in camera 22-2 defines an image plane for camera 22-2, which lies within a focal plane of lens 80-2. The photodetector array is divided into a plurality of pixels, which each pixel corresponding to a unit area on back surface 441. The plurality of pixels together have a field of view 86-2, which covers substantially the entire back surface 441. In an alternative embodiment, field of view 86-2 covers only a portion of back surface 441 and is scanned along front surface 441 with illumination path 37-2. The images collected by camera 22-2 are passed to computer controller 26 for analysis as discussed above. In embodiments where the second measurement instrument 4346 illuminates only a portion of back surface 440, and scans the back surface by rotating or otherwise moving substrate 432, the scattered light can be collected by suitable optics and detected by a suitable a non-imaging photodetector, such as a photomultiplier or a photodiode. The photodetector has at least one element or pixel that is positioned in a focal plane or focal point of the optics that collects the scattered light.

In order for both surfaces 440 and 441 to be inspected at the same time, substrate 432 is held by a substrate holder 442 that allows maximum optical access to both surfaces, including the substrate edges and bevel. FIG. 9 schematically shows one method for holding substrate 432 in which contact with substrate 432 occurs only along a small portion of the outer edge, along the direction of illumination. Substrate holder 442 is positioned "downstream" of light beam paths 37-1 and 37-2 relative to substrate 432. This substrate holding position minimizes the substrate surface area that is obscured from cameras 22-1 and 22-2 and also minimizes contamination of surfaces 440 and 441 due to contact with holding surfaces.

Cameras 22-1 and 22-2 are positioned above and below substrate 432 so as to detect light emitted from front surface 440 and back surface 441, respectively. The images recorded by cameras 22-1 and 22-2 are analyzed in real time, for example, by computer controller 26 to detect and report flaws and defects on both surfaces substantially simultaneously. In embodiments where substrate rotation or movement is required for one of the two measurements, it may be desirable to perform the first and second measurements in sequence rather than in parallel. In such situations, the substrate holding position for measurement instrument 434 may be different from the substrate holding position for measurement instrument 436.

Computer controller 26 can be configured so that measurement instruments 434 and 436 can work independently, sequentially or simultaneously in concert. An advantage of having measurement instruments 434 and 436 operate independently is that the sensitivities of the two measurement instruments can be set differently. Also, different defect detection and surface analysis techniques can be used for each surface. For example, the sensitivity of measurement instrument 434 can be tailored to effectively detect particles and other defects on patterned surfaces, while the sensitivity of measurement instrument 436 can be set to effectively detect particles and other defects on un-patterned surfaces (i.e, the back side of a wafer). In one embodiment, inspection instrument 434 has a defect sensitivity that is greater than the defect sensitivity instrument 436 such that instrument 434 is capable of detecting smaller defects than instrument 436.

Further, computer controller 26 can use different analysis techniques to process the images collected from front surfaces 440 and 441. The dual surface defect inspection system 430 shown in FIG. 9 therefore permits a broad range of applications within the confines of a single inspection module. As in the previous embodiments, system 430 can be used as a stand alone system or can be integrated as one of several processing modules in a multi-process "cluster tool" or a robotic wafer handling interface to enable in-line metrology as described above. The dual surface defect inspection system shown in FIG. 9 provides a simple, cheap and compact inspection tool with a minimum of moving parts and is capable of rapid inspection of substrates under a variety of different illumination and detection modes. The inspection tool can be used for particles-per-wafer-pass (PWP) measurements as well as for monitoring particle contamination and defects on product wafers.

Figure 10:
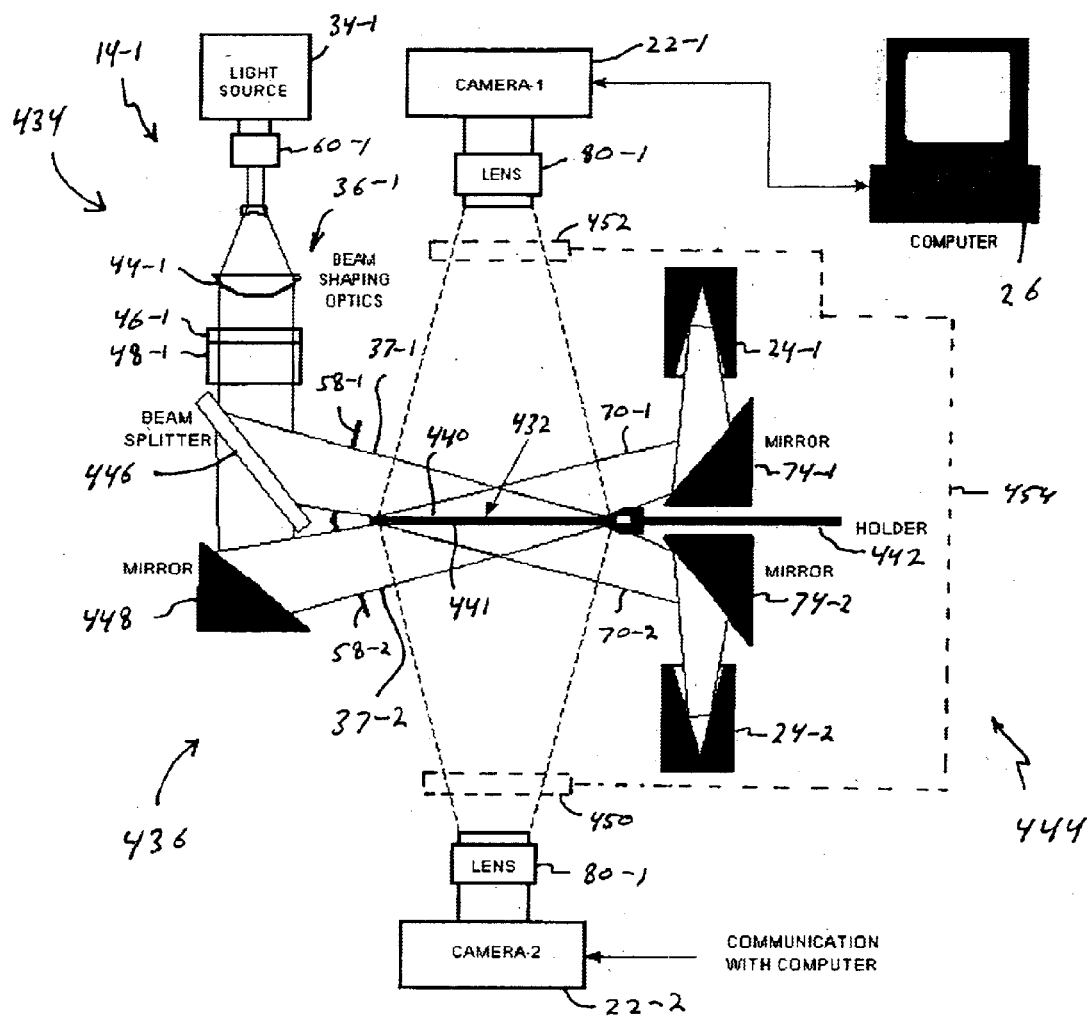
FIG. 10 is a schematic illustration of a dual surface defect inspection system having a single light source, according to an alternative embodiment of the present invention.

FIG. 10 is a schematic illustration of a dual surface defect inspection system 444 according to an alternative embodiment of the present invention. The same reference numerals are used in FIG. 10 as were used in FIG. 11 for the same or similar elements. Inspection system 444 has only a single illuminator 14-1 for illuminating booth surfaces 440 and 441 of substrate 432. In order to illuminate both surfaces, illuminator 14-1 further includes a beam splitter 446, for example, for creating the two light beam paths 37-1 and 37-2. Beam splitter 446 redirects a first portion of the light beam emitted from light source 34-1 toward front surface 440 and allows a second portion to pass to mirror 448. Mirror 448 reflects this portion of the light beam toward back surface 441. The remainder of measurement instruments 434 and 436 operate the same as discussed above with reference to FIG. 9.

In a further alternative embodiment, inspection system 444 has a single camera 22-1 and suitable relay optics represents by boxes 450, 452 and arrow 454 to switch between views of front surface 440 and back surface 441. Images of both surfaces of substrate 432 can then be taken in succession by camera 22-1. Box 450 corresponds to an optical element, which is oriented to collect non-specularly (or specularly) reflected light from back surface 441. Arrow 454 represents an optical path extending from optical element 450 to optical element 452 for passing the light collected from back surface 450 to lens 80-1. When the back surface 441 is selected, each pixel of the photodetector array in camera 22-1 corresponds to an area on back surface 441 and the plurality of pixels together form a field of view that covers substantially the entire back surface 441.

In the embodiments shown in FIGS. 9 and 10, both measurement instruments 434 and 436 detect scattered light from defects under darkfield illumination. However, one or both of the measurement instruments 434 and 436 can be modified as discussed above to operate in alternative detection modes, such as detection of reflected light under bright field illumination and detection of photo-luminescent emissions.

Also, measurement instruments 434 and 436 inspect the substrate as the substrate lies in a horizontal plane, with the two imaging cameras 22-1 and 22-2 placed above and below the substrate for viewing the substrate surfaces along a substantially vertical optical axis. In some applications, it maybe desirable to hold substrate 432 in a vertical plane while imaging cameras 22-1 and 22-2 are disposed on either side of substrate 432 and view the respective surfaces along substantially horizontal optical axis.

In addition, cameras 22-1 and 22-2 view substrate 432 from directions that are normal to the substrate surfaces. In these configurations, the object plane (i.e., substrate surfaces 440 and 441), the lens plane and the image plane (i.e., the photodetector array) are all parallel with one another. In some embodiments it may be advantageous to configure one or both of the measurement instruments 434 and 436 to view the respective substrate surface at an oblique angle, as shown in FIGS. 5a and 5d. In these configurations the object plane, lens plane and image plane intersect along a line.

In another alternative embodiment, the dual surface defect inspection system includes a second metrology tool, such as a high sensitivity wafer scanner or a film thickness monitor. In this embodiment, one of the wafer surfaces is inspected by a single camera-based wafer inspection module corresponding to either the upper or lower half of the system shown in FIG. 9. The other wafer surface is inspected by the second metrology tool. For example, the active, front surface of a wafer can be inspected by a sensitive patterned-wafer scanner, while the un-patterned back surface is inspected by a simpler, cheaper wafer inspection module similar to one of the measurement instruments shown in FIG. 9. This type of system can be used for wafer backside inspection during critical processing steps and semiconductor manufacturing, such as photolithography.

Alternatively, both metrology subsystems could be used to inspect only the active surface of the substrate with the sensitive but slower wafer scanner inspecting only a sample of the substrates, while the simpler, but faster camera-based wafer inspection sub-system inspects all wafers routed to the tool. For example, metrology tool 420 shown in FIG. 8 can be part of a sensitive but slower wafer scanner for inspecting the active surface. In this mode, the faster camera-based measurement instrument can be used as a pre-screening tool for the more sensitive wafer scanner by selecting a small number of defective wafers for a more thorough inspection by the wafer scanner.

In yet another alternative embodiment, the dual surface defect inspection system includes a single camera-based measurement instrument corresponding to either the upper or lower half of the system shown in FIG. 9. Substrate holder 442 includes a robotic wafer handler, for example, that is capable of flipping the substrate to present each surface of the substrate for inspection in succession. A simpler system, without a robotic flipper could also be used for dedicated backside inspection applications.

9. Digital Image Analysis for Defect Detection

The digital images acquired by the detection cameras shown in the above-embodiments are collected and analyzed by the associated computer controller during inspection of each substrate. Each image is a record of the intensity of scattered light arriving at the camera from different points on the substrate surface. Defects are extracted from the scattered light images through image analysis techniques.

Various analysis techniques can be used to process the images. In one embodiment of the present invention, a pixel-to-pixel comparison is made between the test image and a known good reference image stored in computer memory. Those pixels with intensity "difference" values outside a local variance or tolerance range are flagged. The tolerance range accounts for substrate-to-substrate variation, and temporal variation in illumination intensity and camera response, and represents the allowable signal spread for "good parts". The tolerance range may vary in a non-uniform manner over the substrate image, for example, due to variation in illumination intensity and lens resolution over the entire substrate surface and/or due to varying pattern signatures in patterned wafers. For convenience, the pre-computed tolerance range may be stored in memory as a variance image. This variance image can include the individual tolerance range for each pixel in the image. For grey-scale comparison, typically one reference image and one variance image is associated with each different type of substrate being inspected. Different substrate types are classified as those having a surface with a different film, a different pattern, or a similar pattern at a different processing stage or level. For color images, it may be convenient to breakdown the images into their color components resulting in multiple reference/variance images being used during the comparison process.

FIG. 11 is a flow chart, which shows the basic image acquisition and analysis process 469 used to extract defects with the use of a previously stored reference image, according to one embodiment of the present invention. The process shown in FIG. 11 can be implemented through programmed software instructions by the computer controller associated with the inspection module. The computer controller can include dedicated image processing hardware, such as pipe-line processors. The programmed software instructions can be stored on any computer-readable medium, either internal or external to the controller.

In process 469, a test image of the substrate is acquired by the camera according to any one of the embodiments discussed above, at step 470. At step 471, the test image is normalized to compensate for changes in illumination conditions. Normalizing the test image with respect to a reference image can be accomplished through techniques such as histogram matching and normalizing mean intensities. At step 472, the normalized test image is optionally equalized by performing a gamma correction (a histogram equalization) to enhance the contrast level of the normalized test image. At step 473, the equalized test image is shifted to align it with a previously stored background reference image 474. This shifting can be based on a detected perimeter of the substrate within the test image and any reference features on the substrate. For example, substrates often include a notch on its perimeter for orientation purposes. These features are aligned with corresponding features in the stored background reference image 474. At step 475, the background reference image 474 is subtracted from the test image to produce a difference image.

At step 476, the difference image is compared with a variance image 477 to create an error image that highlights those pixels that are outside the predefined threshold tolerance range. This comparison is done by performing a binary threshold operation on each pixel in the difference image with the threshold value of the corresponding pixel in the variance image. Alternatively, a common threshold value can be used for all pixels. At step 478, a blob analysis is performed on the error image to count and quantify potential defects. At step 479, actual defects are screened, identified and classified from the error image.

In the above process, the shifting and alignment step 473 is particularly important for patterned substrate inspection, where it is needed to compensate for variations in pattern position from substrate-to-substrate. Also, slight variations in the substrate placement position can occur whenever a substrate is placed within the camera field of view by the transport arm. A small subset of pattern features (fiducial marks) may be used for pattern matching on a global scale for the entire substrate. If the pattern has been produced using a step and repeat lithography process, it may be necessary to independently align individual die in the test image with its corresponding counterpart in the reference image to account for random position alignment errors during the lithography process, as well as distortion errors caused by imaging with imperfect optics. This local alignment at the individual die scale may be performed by dividing the test image into unit cells centered around each repeating die, performing the comparison at a unit cell level and the stitching together the unit cells again to obtain the global scale difference image at step 475.

Sub-pixel accuracy in image alignment/registration at both global and local levels is important during image subtraction step 475 to avoid "ghost" differences. For un-patterned wafer surfaces, the image alignment may be performed using only global features such as the wafer edge and notch as reference features. For the case of patterned wafer surfaces, sophisticated pattern matching techniques can be used to ensure good alignment and registration of patterns to sub-pixel levels. The most powerful techniques have the capability to handle variation in contrast changes, rotation, scale and partially degraded and occluded patterns. Less robust techniques based on normalized grey-scale correlation may also be used under well-controlled conditions.

FIGS. 12A–12D show an example of defects detected using the process shown in FIG. 11 for the case of a patterned wafer surface. For convenience, only a narrow strip of the wafer is shown in each figure, even though the process is applicable to images covering the entire wafer surface. FIG. 12A shows the stored background reference image. FIG. 12B shows the test image acquired at step 470. FIG. 12C shows the difference image produced at step 475 by subtracting the reference image from the test image. FIG. 12D shows the thresholded image (error image) produced at step 476 by comparing the difference image with the variance image 477. The defects exposed in FIG. 12D can be further analyzed for classification and reporting, at steps 478–479.

10. Image Analysis for Un-Patterned Surface Inspection

The optical inspection module of the present invention can also be used to extract point defects from the image of an un-patterned substrate surface when it is impractical to use a previously created background reference image. This situation may arise when inspecting blank wafers or the wafer back side surface for contamination, for example. The surface finish on the wafer back side may vary greatly from wafer to wafer and it can become impractical to create the representative background reference image suitable for background subtraction. Nevertheless it is desirable to perform some sort of background correction on the test image in order to account for effects such as non-uniform illumination and thereby permit defects to be separated from the background by using morphological operations such as intensity thresholding. When a background reference image is not available, it is reasonable to use neighborhood pixel information in the test image itself to create a self-reference image for use in background correction.

A convenient way of creating a self-reference image is to apply a convolution filter such as a Laplacian filter to the test image. Application of such a filter is equivalent to subtracting the intensity at each pixel with a neighborhood average intensity background. Convolution filters process images by multiplying the pixel intensity values in a given portion of the image or "image neighborhood" by a matrix of filtering coefficients. This matrix of integer value elements is called a "kernel", and is the same size as the neighborhood to which the kernel is being applied. The results of this multiplication (i.e. of the pixel intensity with the corresponding kernel element) for the neighborhood are summed and divided by the sum of the filter kernel. The result replaces the center pixel in the image neighborhood. Each pixel in an image can be process in this manner. Suitable convolution filters are described in more detail in J. C. Russ, "The Image Processing Handbook", CRC Press, Ann Arbor, Mich. (1995).

The convolution filter has the property of highlighting point and line defects. Other filters with similar properties can be used for this purpose in alternative embodiments of the present invention. In one embodiment of the present invention, this filtering procedure is implemented through computer software operated by the process controller associated with the inspection module.

FIG. 13 is flow chart illustrating an example of a process 480 for implementing spatial filtering with a convolution filter. In process 480, a test image of the substrate is acquired at step 481 with any one of the inspection modules discussed above. At step 482, a Laplacian filter is applied to the test image to accentuate the bright spots, edges or areas typically caused by defects. At step 483, each pixel of the filtered test image is compared to a threshold value 484 (a common value or a value unique to that pixel) to separate pixels having intensities above the threshold value from the background. At step 485, a blob analysis is performed on the separated pixels to count and characterize defect like features. At step 486, a defect geometry selection algorithm is used to screen out "false" defects and report the actual defects found.

FIGS. 14A–14C show a sequence of images where a spatial filtering technique was used to highlight 0.5 micrometer polystyrene latex particles on a virgin 200 millimeter silicon wafer. Again, FIGS. 14A–14C show only a part of the wafer image. FIG. 14A shows the test image acquired at step 481. FIG. 14B shows the Laplacian filtered image produced at step 482. FIG. 14C shows the thresholded image produced at step 483. In this sequence of images, a Laplacian filter was used to separate pixels representing particles from background pixels representing the unblemished surface of the wafer.

The self-referenced method shown in FIG. 13 can also be applied to the inspection of other un-patterned substrates such as magnetic recording discs, flat panels, polished ceramic packaging substrates, etc. It should be understood that the process shown in FIG. 13 is exemplary, and alternative methods can be devised having a similar overall effect. This overall effect is to highlight defect information by performing a self-referencing background correction using neighborhood information.

In one embodiment, the process shown in FIG. 13 is used to create a self-referenced image for the back side of a semiconductor wafer. In order to obtain an image of the back side, the substrate can be physically inverted or "flipped" by the transport arm onto its front side so as to expose the back side to the camera. Alternatively, the substrate holder (such as holder 20 shown in FIG. 1 or holder 370 shown in FIGS. 9 and 10) can be configured to hold the substrate along its perimeter or side edges and a second camera can be positioned to image the back side of the substrate from below the substrate holder, opposite to the first camera. Images of the front and back sides can be taken simultaneously or in sequence with one another.

11. Patterned Wafer Inspection Using Image Analysis Based on Spatial Filtering

The inspection module of the present invention can also be used in a self-reference method for extracting point defects from the image of a patterned substrate surface, when a previously created background reference image is not available. This situation may arise when using the inspection module to inspect a new type of wafer introduced into the production line for the first time, for example. Aside from this, the self-reference technique can be desirable due to the following advantages. First, there is no need for a reference image database. Second, there is no need for prior knowledge about the wafer being inspected. Third, there is no need for precise wafer alignment with respect to the illumination source. Fourth, alignment and registration between the test and reference images during background correction is greatly simplified. The self-reference technique described here produces a substantially defect-free reference image from a test image of the wafer being inspected by the optical inspection module. This same technique is also applicable to inspection of un-patterned wafers.

The method is based on creating a defect-free reference image by applying a median filter (or other similar mathematical function such as an average or mean, etc.) to the test image. A median filter has the effect of replacing the intensity of a pixel by the neighborhood median intensity, as described in J. C. Russ, *The Image Processing Handbook*, CRC Press, Inc. (1995). For each pixel in the test image, a corresponding pixel is produced in a reference image, which has having an intensity equal to the mathematical median of the intensities of a selected set of pixels in the test image that surround that pixel. In the present embodiment, the median filter erases point defects from the test image to create a defect-free reference image that is already perfectly aligned with the test image. Performing the image subtraction results in a difference image in which point defects can easily be distinguished. The method is implemented through the computer software used to operate the wafer inspection module or as a subsequent processing step, as discussed above.

FIG. 15 is a flow chart illustrating a spatial filtering process 500 according to one embodiment of the present invention that can be used for processing patterned and un-patterned wafer surfaces. A test image of the substrate is acquired at step 501. At step 502, a median filter is applied to the test image to create a reference image in which the bright sharp spots and edges typically caused by defects are attenuated or blurred. At step 503, the reference image produced at step 502 is subtracted from the test image acquired at step 501 to create a "difference" image. At step 504, each pixel in the difference image is compared to a threshold value (or selected variance range) to separate those pixels having intensities above the chosen value (or outside the selected variance range) from the background. Alternatively, a variance image can be used instead of a single threshold value or variance range. At step 506, a blob analysis is performed on the separated pixels to count and characterize defect-like features. At step 507, a defect geometry selection algorithm is used to screen out "false" counts and to prepare a report of the defects found.

It should be understood that the flow chart shown in FIG. 15 is exemplary, and alternative methods can be devised for performing a self-referencing background correction, and using filtering to create a clean reference image from the test image itself.

FIGS. 16A–16D show a sequence of images where spatial filtering has been used according to the process shown in FIG. 15 to detect particles on a 150 millimeter patterned silicon wafer surface. In FIGS. 16A–16D, only part of the image is shown. FIG. 16A shows the test image acquired at step 501. FIG. 16B shows the median filtered image (reference image) produced at step 502. FIG. 16C shows the difference image produced at step 503. FIG. 16D shows the thresholded image (error image) produced at step 504. By subtracting the reference image in FIG. 16B from the test image in FIG. 16A, bright pixels representing particles can be distinguished from darker background pixels representing the patterned surface of the wafer. The self-reference method described above can also be applied to the inspection of other patterned substrates such as flat panels and ceramic packaging substrates.

12. Patterned Wafer Inspection Using Computer Pattern Filtering (Frequency Filtering)

Optical inspection of patterned wafer surfaces is often complicated by the strong localized scattering from the pattern of elements on the integrated circuit being fabricated. The pattern behaves like a diffraction grating and projects a strong diffraction pattern against which the faint scattering signal from a random defect can be difficult to distinguish. Patterned wafer inspection systems of the prior art have used optical components to perform Fourier filtering to selectively attenuate the background pattern. Prior art inspection tools generally have imaged the wafer surface at a high magnification so that only a small portion of a single die is within the field of view of the system. For such systems, it is important that the pattern on the wafer being inspected has a high degree of intra-die periodicity, such as in dynamic random access memory (DRAM) devices. In contrast, the optical inspection module of some embodiments of the present invention images the entire wafer at one time.

FIG. 17 is schematic representation of a typical patterned wafer surface 520 showing the regular placement of individual die 522. Lx and Ly are the inter-die pitch spacing in the X and Y directions, respectively. As shown in FIG. 17, a typical patterned wafer has a high degree of periodicity. Each point on a die, whether DRAM or logic, is repeated multiple times in both the X and Y directions. The optical inspection module of the present invention can exploit this periodicity to detect particles and defects on patterned wafers through computer pattern filtering, with no need for a previously created reference image of the patterned wafer.

FIG. 18 is flow chart illustrating a process 530 for computerized pattern filtering to detect defects on patterned wafer surfaces. At step 531, the optical inspection module acquires a test image of the patterned surface. For compatibility with the FFT algorithm used in step 532, the test image preferably has a resolution of $2^m \times 2^n$, where m and n are integers. At step 532, the computer controller (or a subsequent processing computer) applies a fast Fourier transform (FFT) to the test image to create a transform image. The transform image is filtered, such as by using a high-pass filter, at step 533 to remove bright spots corresponding to the pattern on the wafer surface. The transform image expresses the test image's frequency domain as a symmetrically centered cloud of points, where brightness represents the amplitude of the waveform, and position represents the frequency of the waveform. Regular, periodic features in the test image are mapped onto bright spots in the frequency domain. These "hot" spots with frequencies representing the periodic background are attenuated using a suitable high-pass filter or masking filter. Alternatively, more sophisticated filtering techniques can be used at step 533 to remove features produced by the repeating patterns of die.

The filtered transform image produced at step 533 is then subjected to an inverse FFT transform, at step 534, to recreate an image of the substrate with the background filtered out. At step 535, each pixel in the recreated image is compared to a threshold value 536, which can be a single value, a variance range or corresponding value of a pixel in a variance image. This binary threshold operation separates pixels in the recreated image having intensities above the chosen value from the background. At step 537, a blob analysis is performed on the separated pixels to count and characterize defect-like features. At step 538, a defect geometry selection algorithm is used to screen out "false" counts and to prepare a report of the defects found.

FIG. 19A shows a test image of a patterned 200 millimeter wafer surface. FIG. 19B shows the corresponding frequency spectrum image obtained by computing the FFT at step 532 in FIG. 18. The simple nature of the frequency spectrum makes it easy to filter. The test image shown in FIG. 19A can be formed using incoherent light, unlike in the case of most prior art systems where coherent light is needed to accomplish the filtering through optical hardware components.

Computer pattern filtering is often computationally intensive. Therefore, this type of filtering is unsuitable for use in prior art wafer inspection systems where a large number of images are needed to inspect a wafer. In contrast, the computer pattern filtering described in FIG. 18 is ideally suited for the optical inspection modules discussed above since only a single test image is processed per inspected wafer. FFT operations can be performed with a 1K×1K resolution image in a matter of seconds.

FIGS. 20A–20E show a sequence of images where computer pattern filtering has been used to detect particles on a 150 millimeter patterned wafer surface according to the method shown in FIG. 18. FIGS. 20A–20E show only a narrow slice of the wafer image. FIG. 20A shows the test image obtained at step 531. FIG. 20B shows the FFT transform image produced at step 532. FIG. 20C shows the high-pass filtered FFT transform image produced at step 533. FIG. 20D shows the inverse FFT image produced at step 534. FIG. 20E shows the thresholded image (error image) produced at step 535.

13. Wafer Inspection Method Using a Combination of Image Analysis Methods

Three methods for detecting particles on patterned wafer surfaces have been described in the preceding sections. The advantages and disadvantages of these three methods are summarized in Table 2 below.

TABLE 2

|  | REFERENCE IMAGE SUBTRACTION | MEDIAN FILTERING | FREQUENCY FILTERING |
| --- | --- | --- | --- |
| Stored Reference Images | Needed | Not needed | Not needed |
| Pattern Alignment & Registration | Needed | Not needed | Not needed |
| Defect Detection Capability | Most powerful, can detect point, line and area defects | Best for point defects | Periodic defects not detected |
| Periodicity of pattern | Effective for periodic and non-periodic patterns | Effective for periodic and non-periodic patterns | Effective for periodic and non-periodic patterns |
| Wafer Orientation | Prefer fixed orientation | Not fixed | Not fixed |
| Sensitivity | Best | Good | Moderate |

In many circumstances, it may be preferable to use only one of these three methods. However, it has been observed that different inspection techniques have varying degrees of effectiveness for different types of defects. One embodiment of the present invention therefore uses a suitable combination of the multiple image analysis methods for maximizing flexibility of patterned (or un-patterned) wafer inspection.

FIG. 21 is flow chart, which shows an example process 550 for combining results from two or more of analysis methods such as those described in Table 3. In one embodiment of the present invention, each of the three methods shown in Table 3 produces a defect map having a plurality of pixels. Each pixel in the defect map comprises a binary value (or other value such as an intensity) indicating whether a defect exists within a corresponding unit area on the substrate surface. The defect maps from each method are input to process 550 at steps 551, 552 and 553, respectively. Suitable masks 554–556 can be applied to defect maps 551–553, respectively, to exclude areas such as the wafer edges, etc. Also, masks 554–556 can be used to negate defects detected within certain areas on the substrate surface for purposes of false count rejection. For example, masks 554–556 can have a plurality of pixels representing a mask image, wherein each pixel has a binary masking value that can vary from one set of pixels to the next according to type and location of features on the substrate imaged by those pixels.

The masked images are then combined by an image operation at step 557. The image operation can include a logical "AND", a logical "OR" or some weighted combinatory operation, for example. A logical "AND" operation can be use to create a conservative defect data set where the number of "false positives" is minimized. With the logical "AND" operation, only those pixels in which all three defect maps indicate the presence of a defect are identified as an actual defect. A logical "OR" operation can be used when it is desirable to maximize the defect detection rate. With a logical "OR", a given pixel is identified as containing a defect if the defect map produced by any one of the three methods indicates the presence of a defect in that pixel. A weighted combinatory operation would give defects identified by one method greater weight relative to defects identified by another operation. The combined image produced a step 557 is then reviewed by the software program for defect detection and classification at step 558.

14. Detection of Defects on Substrates with Noisy Backgrounds

One of the problems associated with the inspection of patterned wafers is the high dynamic range of the background scattering that arises from the integrated circuit patterns etched on the wafer surface. When the optical inspection module of the present invention is used to inspect patterned wafers, the patterns act as diffraction gratings and the intense, highly directional scattering results in test images having a highly non-uniform intensity background. For images possessing such a high dynamic range in intensity, the bright regions limit defect sensitivity by limiting the allowable range of camera integration (exposure) times for which pixels are not saturated. When a pixel is saturated, no information on the presence or absence of defects can be obtained. In such as situation, one method to avoid a decrease in sensitivity is to maintain the long exposure times while masking out the saturated regions of the test image prior to performing the image analysis steps. This masking can be implemented through the software programs associated with the computer controller.

Diffraction from patterned wafers is highly sensitive to wafer orientation with respect to the incident light beam. One way to inspect the entire wafer surface are is to acquire multiple test images with the same wafer oriented at different angles, as shown in FIG. 5D for example, so that a region masked in one orientation will generally not be masked in another orientation. The multiple masked test images can then be combined in software to generate a complete test image with little or no pixels being masked.

Masking can also be implemented through hardware. For example, a programmable liquid crystal display (LCD) mask can be placed in front of the focal plane of the CCD camera, as shown in FIG. 22. FIG. 22 is schematic illustration of a portion of an inspection module 600 having a wafer holder 602, which holds a wafer 604, a large array, cooled CCD camera 606 and a high resolution fast video lens 608. Camera 606 has a photodetector array 610 having a field of view 612 through lens 608 that covers substantially the entire wafer 604. A programmable LCD mask 614 is positioned between photodetector array 610 and lens 608.

Camera 606 obtains a first test image of wafer 604 with LCD mask 614 turned off such that all pixels in the mask are transparent. Diffraction patterns appear as saturated regions in the first test image. Next, the first test image is electronically mapped on to LCD mask 614. The LCD pixels corresponding to the saturated regions are turned on such that those pixels are opaque. The opaque pixels mask photodetector array 610 at the bright regions. A second test image is then acquired by camera 606 through mask 614. The second test image has diffraction patterns attenuated by masking and may be analyzed using the techniques described above.

Another problem associated with high dynamic range images is that the background noise amplitude varies greatly from pixel to pixel, with the brighter regions of the image generally having a high noise level. When using image processing methods such as reference image comparison or computer filtering referred to above, it is often desirable to use a variable threshold to separate particles and defects from background across the entire image. A higher threshold is generally needed at the brighter regions of the image. Ideally, in the case of high dynamic range images, a CCD camera having a logarithmic response can be used. Alternatively CCD cameras having an anti-blooming function can be used. If a CCD camera with a linear response is used, "gamma" correction can be applied to the test image before subjecting it to image analysis. One scheme would be to reassign pixel brightness levels in the image according to a suitable transfer function. For example a logarithmic function would compress the brightness at the bright end of the scale. This image histogram equalization procedure can improve the signal-to-noise ratio for a high-dynamic range image when using some of the image analysis techniques described above.

15. Conclusion

The optical inspection module of some embodiments of the present invention illuminates the entire surface of a substrate at one time. Certain embodiments are capable of imaging or otherwise inspecting both the front and back sides of the substrate simultaneously or sequentially. Images captured by the cameras are analyzed in real time by a computer to detect and report flaws and defects. This large-area-illumination and large-area-imaging provides a simple, cheap and compact inspection tool with a minimum of moving parts and which is capable of rapid inspection of substrates under a variety of different illumination and detection modes. The various features and elements of the inspection module provide the module with considerable flexibility in function. The inspection module and methodology discussed above are adaptable for inspection of different types of substrate surfaces such as that of bare wafers, patterned wafers, back sides of wafers, film coated wafers, flat panels, magnetic recording discs, and electronic packaging substrates. The inspection methodology is also flexible enough to permit multiple optical measurement modes, such as light scattering and photo-luminescence. The inspection module is capable of being packaged as a stand-alone, bench-top or integrated metrology system for different applications.

Although the present invention has been described with reference to preferred embodiments, workers skilled in the art will recognize that changes may be made in form and detail without departing from the spirit and scope of the invention.

What is claimed is:

1. An optical inspection module for inspecting a substrate having first and second opposite planar surfaces, the module comprising:
    a substrate holding position;
    a first measurement instrument comprising:
        a first illumination path extending to the substrate holding position and having a grazing angle of incidence with respect to the first surface of the substrate when the substrate is held in the substrate holding position, wherein the first illumination path illuminates substantially the entire first surface;
        a first optical element, which is oriented to collect non-specularly reflected light that is scattered from the first illumination path by the first surface, the first optical element having a focal plane; and
        a first photodetector having a plurality of pixels which are positioned within the focal plane of the first optical element, wherein each pixel corresponds to an area on the first surface and the plurality of pixels together form a field of view that covers substantially the entire first surface; and
    a second measurement instrument comprising a sensor oriented for sensing a physical characteristic of the second surface when the substrate is held in the substrate holding position and the first surface is being illuminated.

2. The optical inspection module of claim 1 wherein the first surface comprises a back surface of the substrate, and the second surface comprises an active surface of the substrate.

3. The optical inspection module of claim 1 wherein the second measurement instrument comprises:
    a second illumination path extending to the substrate holding position and illuminating at least a portion of the second surface when the substrate is held in the substrate holding position;
    an optical element, which is oriented to collect light reflected from the second illumination path by the second surface and has a focal plane; and
    a second photodetector positioned within the focal plane of the optical element.

4. The optical inspection module of claim 3 wherein:
    the second illumination path has a grazing angle of incidence with respect to the second surface of the substrate and illuminates substantially the entire second surface;
    the optical element comprises a second lens, which is oriented to collect non-specularly reflected light that is scattered from the second illumination path by the second surface; and
    the second photodetector comprises a plurality of pixels, wherein each pixel of the second photodetector corresponds to an area on the second surface and the plurality of pixels together form a field of view that covers substantially the entire second surface.

5. The optical inspection module of claim 3 wherein the second measurement instrument has a defect sensitivity that is greater than that of the first measurement instrument and is capable of detecting smaller defects on the second surface than the first measurement instrument is capable of detecting on the first surface.

6. The optical inspection module of claim 3 wherein:
the second illumination path has a non-grazing angle of incidence with respect to the second surface of the substrate; and
the optical element is oriented to collect specularly light that reflected from the second illumination path by the second surface.

7. The optical inspection module of claim 3 and further comprising:
a first light source having a first light beam port, which is optically coupled to the first illumination path; and
a second light source having a second light beam port, which is optically coupled to the second illumination path.

8. The optical inspection module of claim 3 and further comprising:
a single light source having a light beam port, which is optically coupled to the first and second illumination paths.

9. The optical inspection module of claim 1 wherein the second measurement instrument comprises:
a second illumination path extending to the substrate holding position and having a grazing angle of incidence with respect to the second surface of the substrate when the substrate is held in the substrate holding position, wherein the second illumination path illuminates substantially the entire second surface;
a second optical element which is oriented to collect non-specularly reflected light that is scattered from the second illumination path by the second surface; and
an optical path extending from the second optical element to the first optical element for passing the non-specularly reflected light from the second surface to the first optical element, wherein each pixel of the first photodetector further corresponds to an area on the second surface and the plurality of pixels together form a field of view that covers substantially the entire second surface.

10. The optical inspection module of claim 1 wherein:
the first surface of the substrate defines an object plane at the substrate holding position;
the first optical element comprises a first lens having a lens plane; and
the plurality of pixels of the first photodetector define an image plane within the focal plane of the first lens, wherein the lens plane and the image plane are non-parallel to the object plane and intersect with the object plane along a line.

11. The optical inspection module of claim 10 wherein the first lens has an optical axis that is oriented at an oblique angle to the object plane.

12. An optical inspection module for inspecting a substrate having first and second opposite planar surfaces, the module comprising:
a substrate holding position;
a first illumination path extending to the substrate holding position and having a grazing angle of incidence with respect to the first surface of the substrate when the substrate is held in the substrate holding position, wherein the first illumination path illuminates substantially the entire first surface;
a first optical element, which is oriented to collect non-specularly reflected light that is scattered from the first illumination path by the first surface, the first optical element having a focal plane;
a first photodetector having a plurality of pixels which are positioned within the focal plane of the first optical element, wherein each pixel corresponds to an area on the first surface and the plurality of pixels together form a field of view that covers substantially the entire first surface;
a second illumination path extending to the substrate holding position and having a grazing angle of incidence with respect to the second surface of the substrate when the substrate is held in the substrate holding position, wherein the second illumination path illuminates substantially the entire second surface;
a second optical element, which is oriented to collect non-specularly reflected light that is scattered from the second illumination path by the second surface, the second optical element having a focal plane; and
a second photodetector having a plurality of pixels which are positioned within the focal plane of the second optical element, wherein each pixel corresponds to an area on the second surface and the plurality of pixels together form a field of view that covers substantially the entire second surface.

13. The optical inspection module of claim 12 and further comprising:
a first light source having a first light beam port, which is optically coupled to the first illumination path; and
a second light source having a second light beam port, which is optically coupled to the second illumination path.

14. The optical inspection module of claim 12 and further comprising:
a single light source having a light beam port, which is optically coupled to the first and second illumination paths.

15. An optical inspection module for inspecting a substrate having an active surface and an opposite, back surface, the module comprising:
a substrate holding position;
a first measurement instrument comprising:
a first illumination path extending to the substrate holding position and having a grazing angle of incidence with the back surface when the substrate is held in the substrate holding position, wherein the first illumination path illuminates substantially the entire back surface;
a first optical element, which is oriented to collect non-specularly reflected light that is scattered from the first illumination path by the back surface, the first optical element having a focal plane; and
a first photodetector having a plurality of pixels which are positioned within the focal plane of the first optical element, wherein each pixel corresponds to an area on the back surface and the plurality of pixels together form a field of view that covers substantially the entire back surface; and
a second measurement instrument comprising:
a second illumination path extending to the substrate holding position and illuminating at least a portion of the active surface when the substrate is held in the substrate holding position;
a second optical element, which is oriented to collect light reflected from the second illumination path by defects on the active surface and has a focal plane; and
a second photodetector having at least one pixel, which is positioned within the focal plane of the second optical element, wherein the second measurement instrument has a defect sensitivity that is greater than that of the first measurement instrument and is capable of detecting smaller defects on the active surface than the first measurement instrument is capable of detecting on the back surface.

* * * * *

UNITED STATES PATENT AND TRADEMARK OFFICE
CERTIFICATE OF CORRECTION

PATENT NO. : 6,809,809 B2
APPLICATION NO. : 10/379016
DATED : October 26, 2004
INVENTOR(S) : Patrick D. Kinney et al.

It is certified that error appears in the above-identified patent and that said Letters Patent is hereby corrected as shown below:

On the Title Page, Item (75)

Inventors: Change "Nagaraja P. Rao, San Carlos, CA (US) to

--Nagaraja P. Rao, San Leandro, CA (US) --.

Appearing on first page, FIG. 9 should be replaced with formal drawing of FIG. 9.

Appearing on sheet 1 through sheet 22, please replace FIGS. 1-22 with formal FIGS. 1-22.

Signed and Sealed this

Twenty-second Day of May, 2007

JON W. DUDAS
*Director of the United States Patent and Trademark Office*

United States Patent
Kinney et al.

(10) Patent No.: US 6,809,809 B2
(45) Date of Patent: Oct. 26, 2004

(54) OPTICAL METHOD AND APPARATUS FOR INSPECTING LARGE AREA PLANAR OBJECTS

(75) Inventors: Patrick D. Kinney, Hayward, CA (US); Anand Gupta, Phoenix, AZ (US); Nagaraja P. Rao, San Carlos, CA (US)

(73) Assignee: Real Time Metrology, Inc., Castro Valley, CA (US)

(*) Notice: Subject to any disclaimer, the term of this patent is extended or adjusted under 35 U.S.C. 154(b) by 0 days.

(21) Appl. No.: 10/379,016

(22) Filed: Mar. 4, 2003

(65) Prior Publication Data
US 2004/0012775 A1 Jan. 22, 2004

Related U.S. Application Data

(63) Continuation-in-part of application No. 09/994,021, filed on Nov. 14, 2001, now Pat. No. 6,630,996.
(60) Provisional application No. 60/361,799, filed on Mar. 5, 2002, provisional application No. 60/297,660, filed on Jun. 12, 2001, and provisional application No. 60/249,000, filed on Nov. 15, 2000.

(51) Int. Cl.$^7$ ................................. G01N 21/00
(52) U.S. Cl. ................... 356/237.5; 356/237.1; 356/237.4
(58) Field of Search .................. 356/237.1–237.6, 356/600–601, 609, 614; 250/201.1, 201.2, 201.3, 201.4, 250, 559.28, 559.31

(56) References Cited

U.S. PATENT DOCUMENTS

| | | | |
|---|---|---|---|
| 3,790,287 A | 2/1974 | Cuthbert et al. | 356/120 |
| 4,342,515 A | 8/1982 | Akiba et al. | 356/237 |
| 4,373,805 A | 2/1983 | Mallinson | 356/1 |
| 4,377,340 A | 3/1983 | Green et al. | 356/237 |
| 4,378,159 A | 3/1983 | Galbraith | 356/237 |
| 4,482,424 A | 11/1984 | Katzir et al. | 156/626 |
| 4,569,695 A | 2/1986 | Yamashita et al. | 134/1 |
| 4,614,427 A | 9/1986 | Koizumi et al. | 356/237 |
| 4,555,592 A | 4/1987 | Allemand | 356/237 |
| 4,592,223 A | 9/1987 | Lampert et al. | 204/34.5 |
| 4,716,299 A * | 12/1987 | Tanaka et al. | 250/559.01 |
| 4,764,969 A * | 8/1988 | Ohtombe et al. | 382/148 |
| 4,772,126 A | 9/1988 | Allemand et al. | 356/336 |
| 4,827,143 A | 5/1989 | Munakata et al. | 250/574 |
| 4,895,446 A | 1/1990 | Maldari et al. | 356/336 |

(List continued on next page.)

OTHER PUBLICATIONS

W.P. Shaw and R.P. Sopher, "High Speed Automatic Particle Counter", IBM Technical Disclosure Bulletin, vol. 17, No. 9, Feb. 1975.

(List continued on next page.)

*Primary Examiner*—Frank G. Font
*Assistant Examiner*—Sang H. Nguyen
(74) *Attorney, Agent, or Firm*—Westman, Champlin & Kelly

(57) ABSTRACT

An optical inspection module is provided for detecting defects on a substrate having first and second opposite planar surfaces. The module includes a substrate holding position and first and second measurement instruments. The first instrument includes a first illumination path extending to the substrate holding position and having a grazing angle of incidence with the first surface, which illuminates substantially the entire first surface. A first optical element is oriented to collect non-specularly reflected light scattered by the first surface. A first photodetector has a plurality of pixels positioned within a focal plane of the first lens, which together form a field of view that covers substantially the entire first surface. The second instrument includes a sensor oriented for sensing a physical characteristic of the second surface when the substrate is held in the substrate holding position and the first surface is being illuminated.

15 Claims, 22 Drawing Sheets

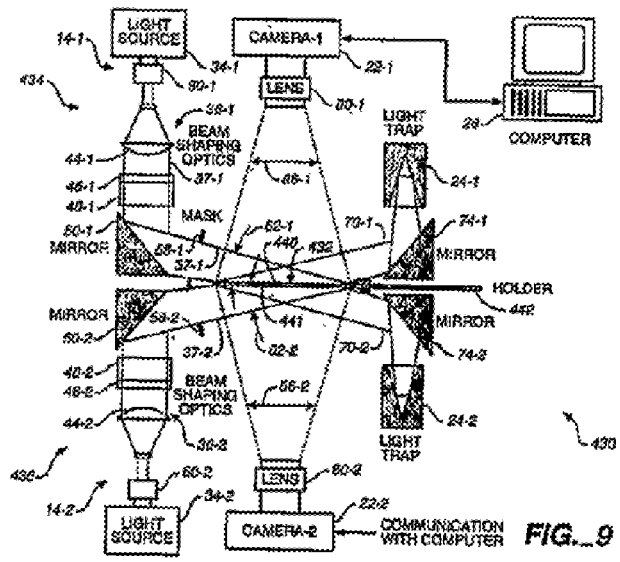

FIG._9

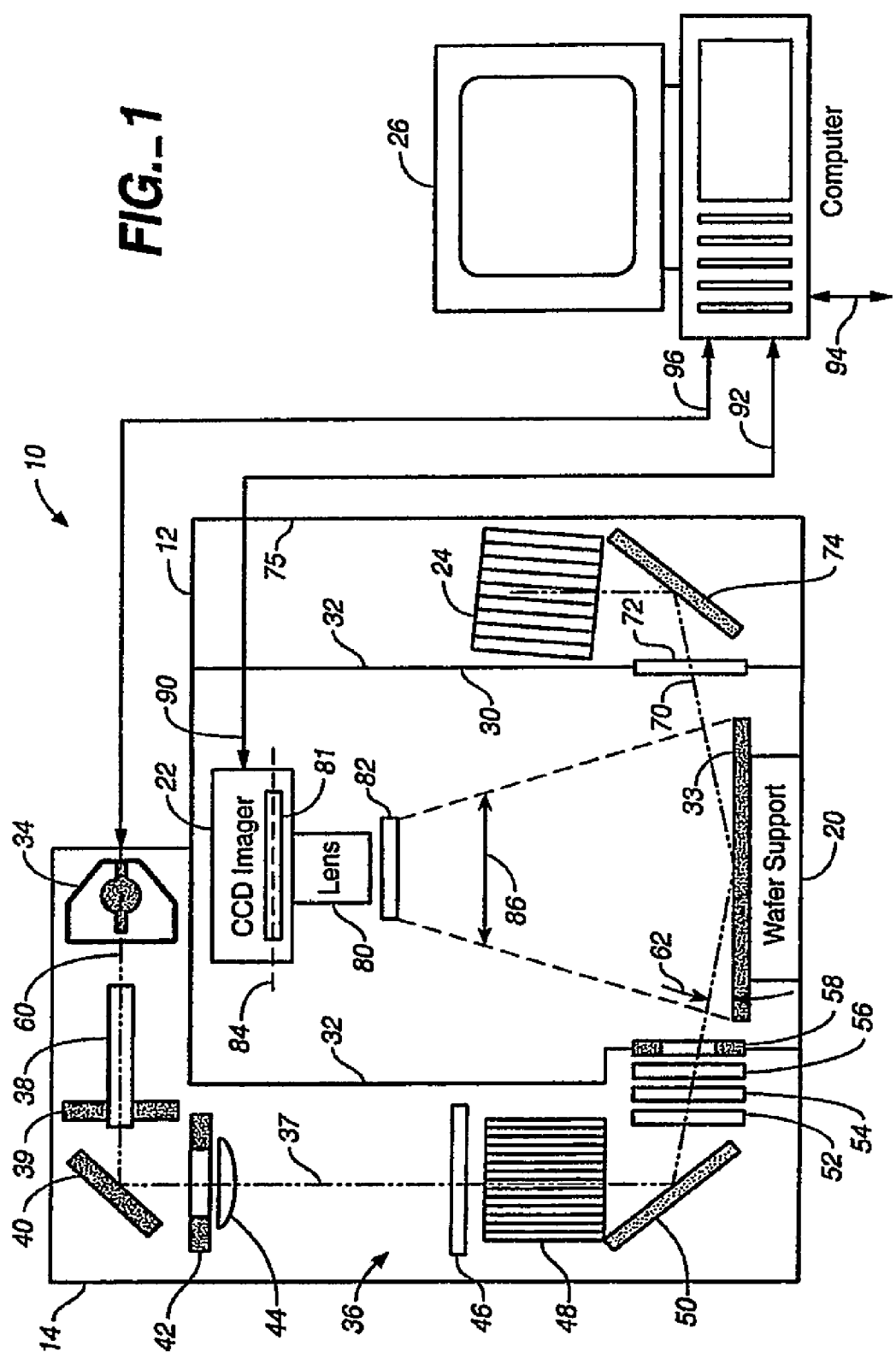
FIG._1

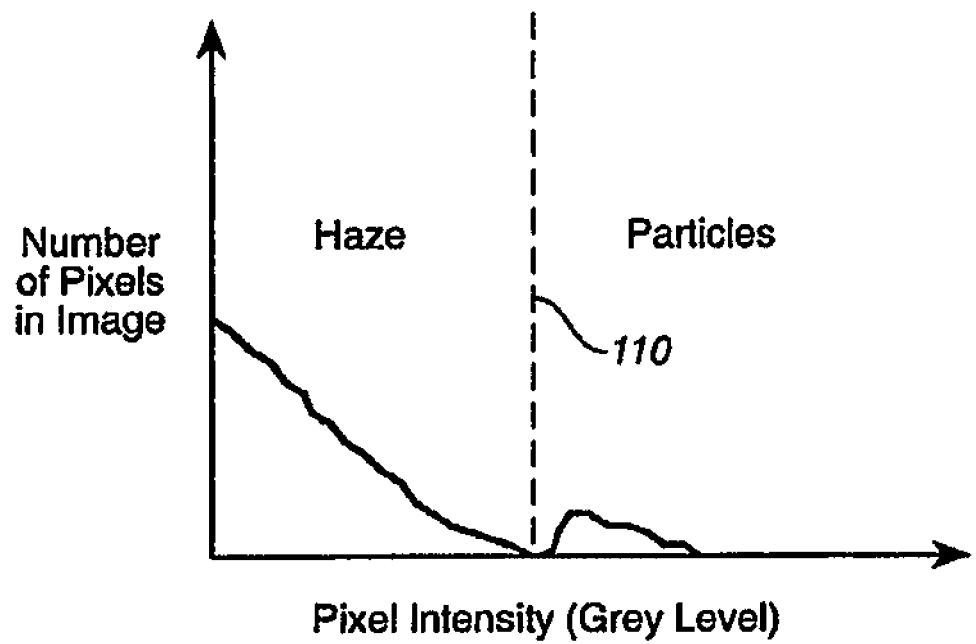
FIG._2

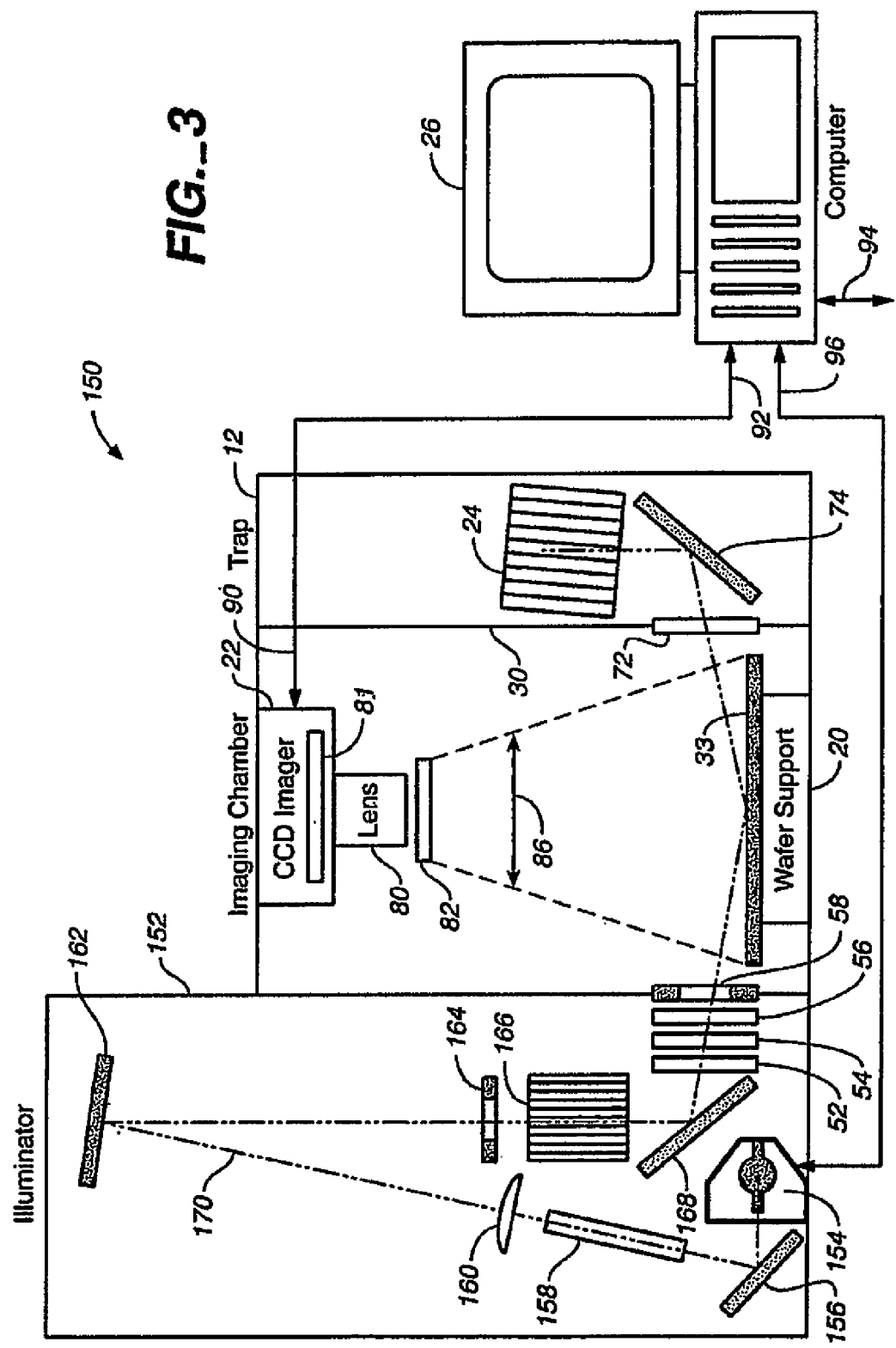

 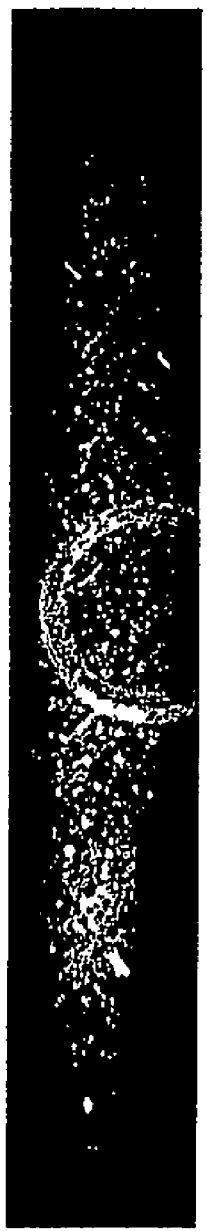 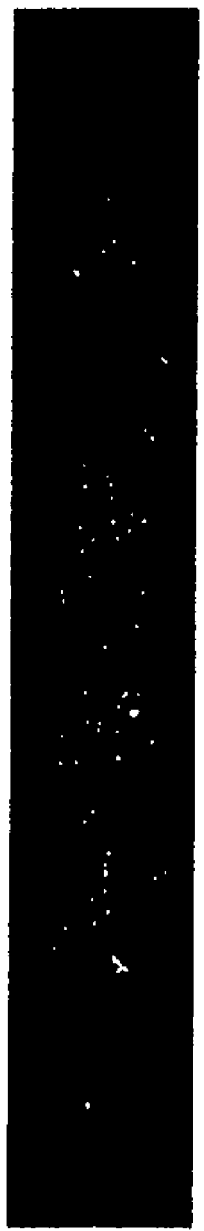
FIG._4A  FIG._4B  FIG._4C

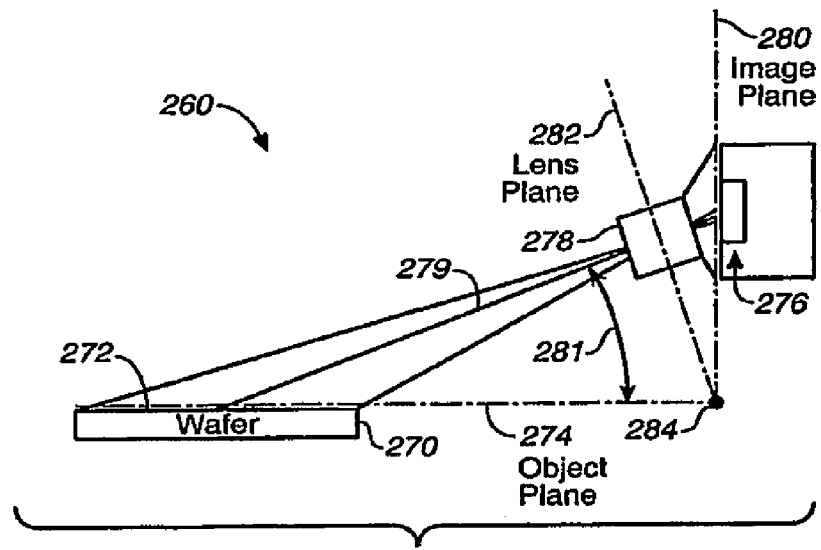
FIG._5A
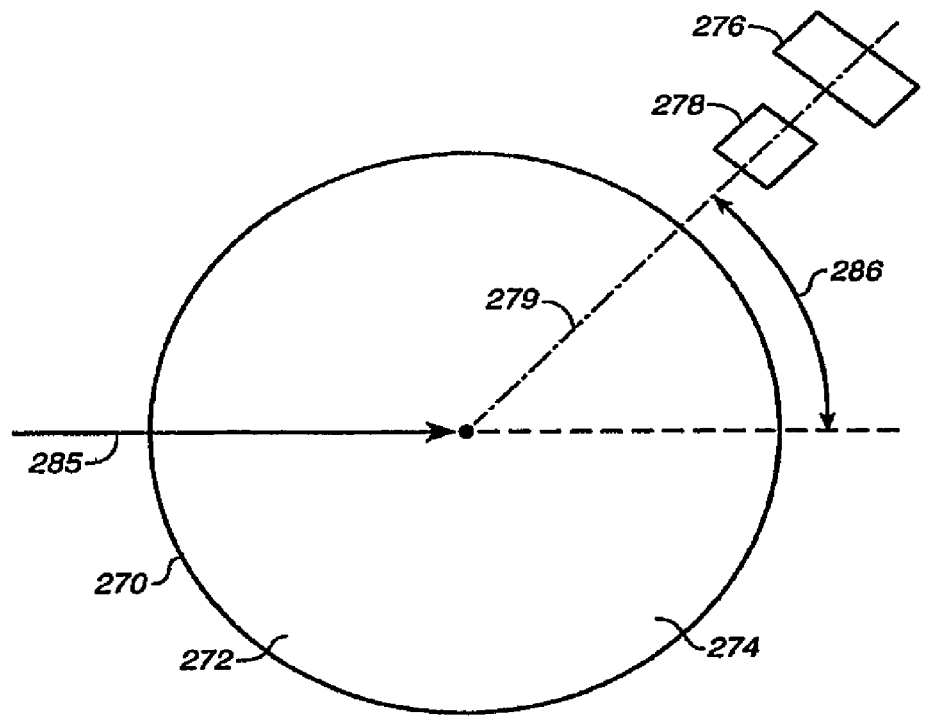
FIG._5B

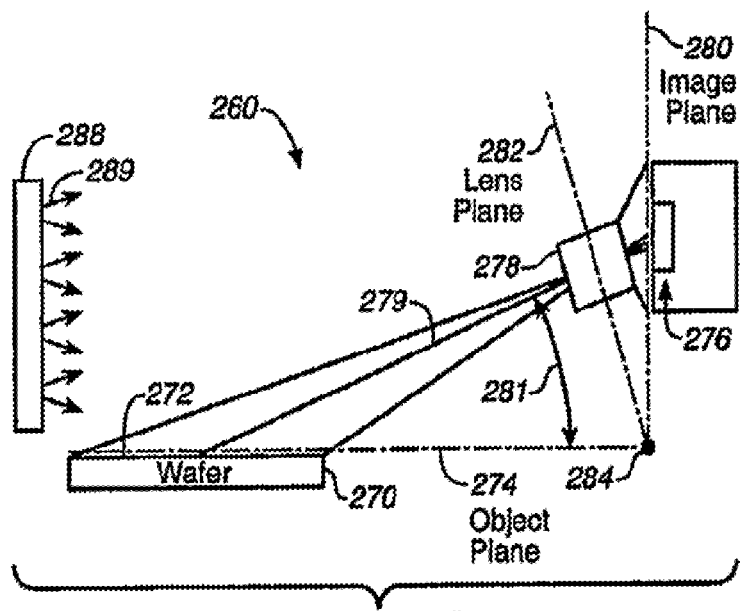
FIG._5C
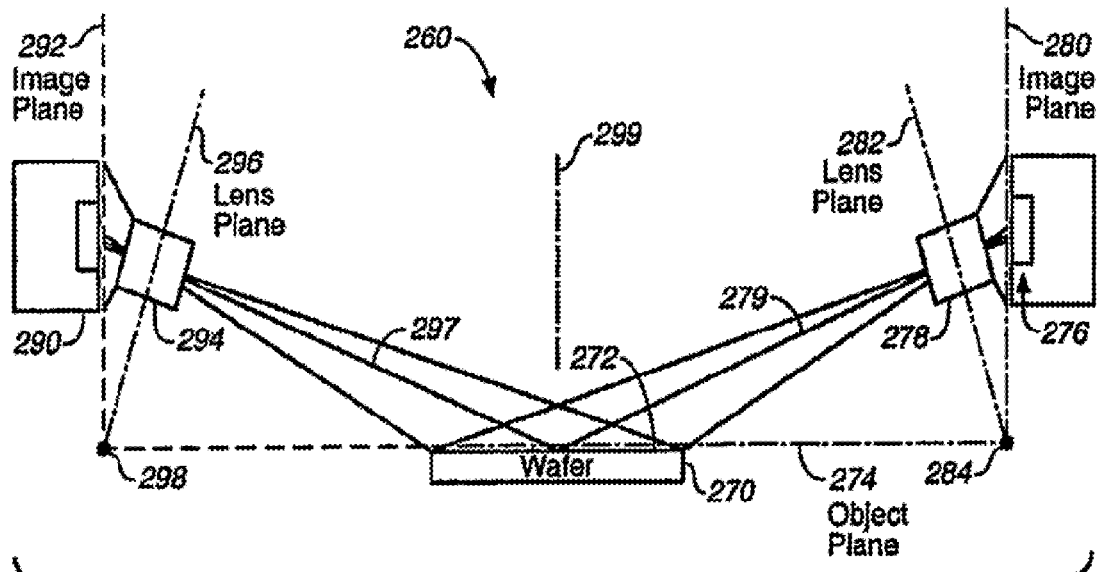
FIG._5D

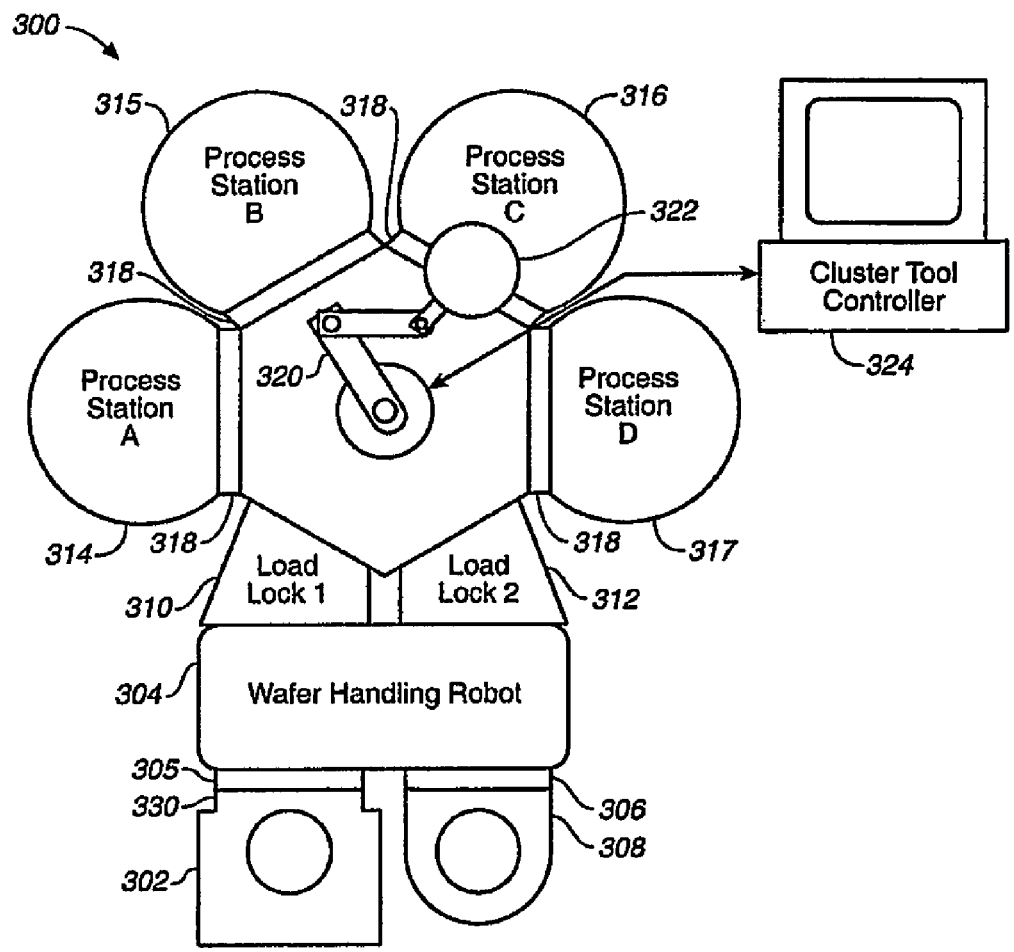
FIG._6

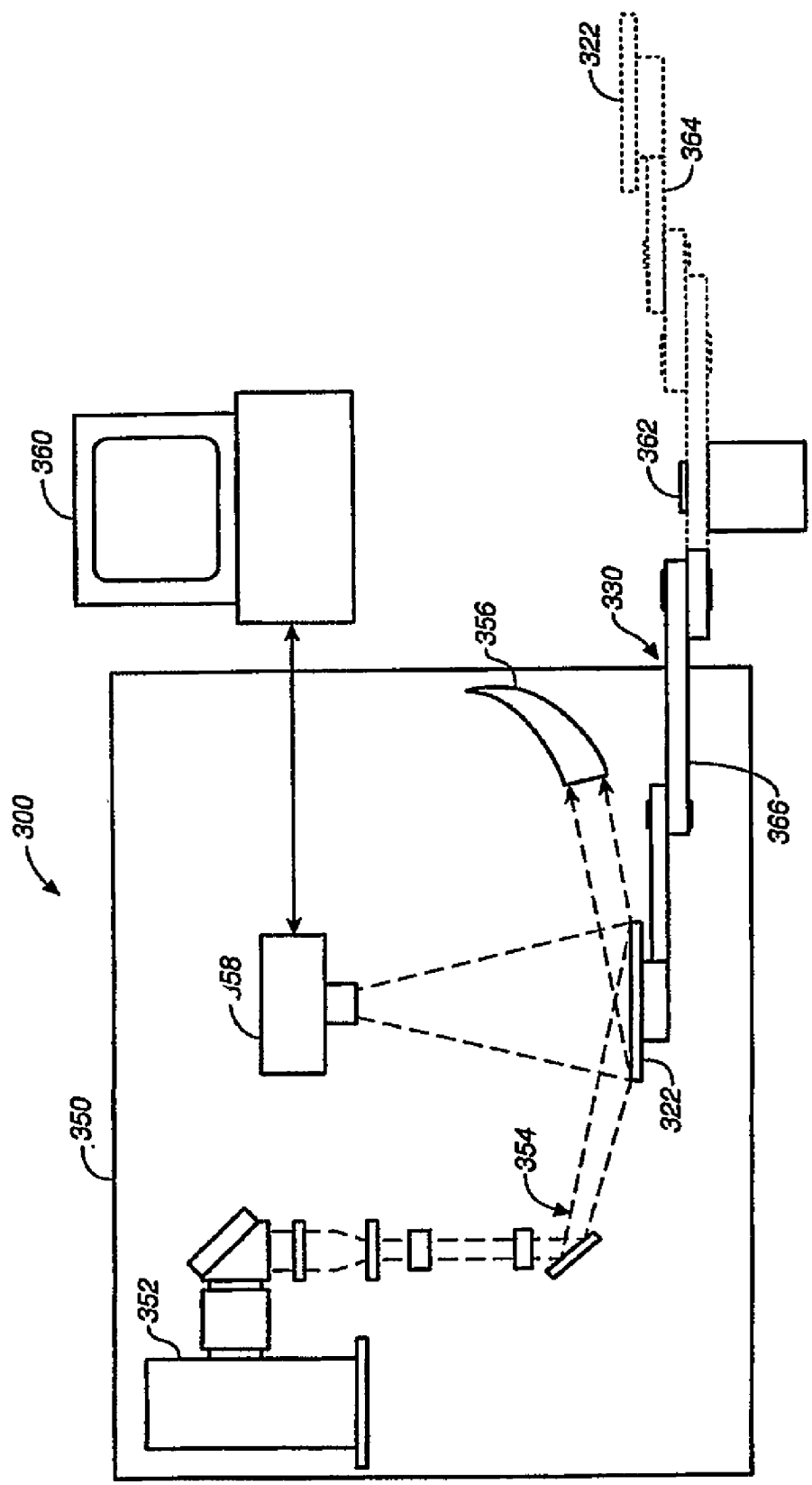
FIG._7

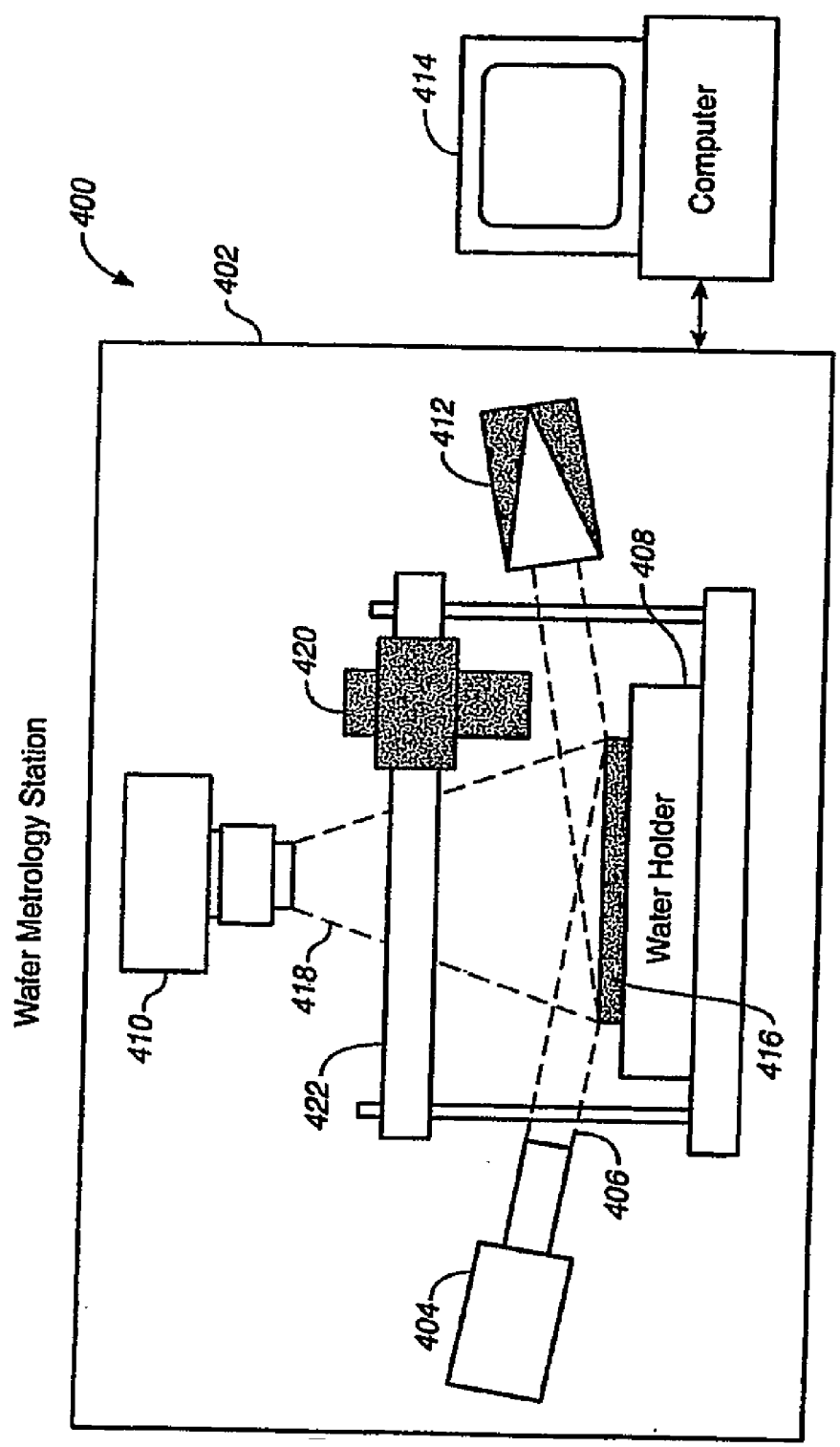
FIG._8

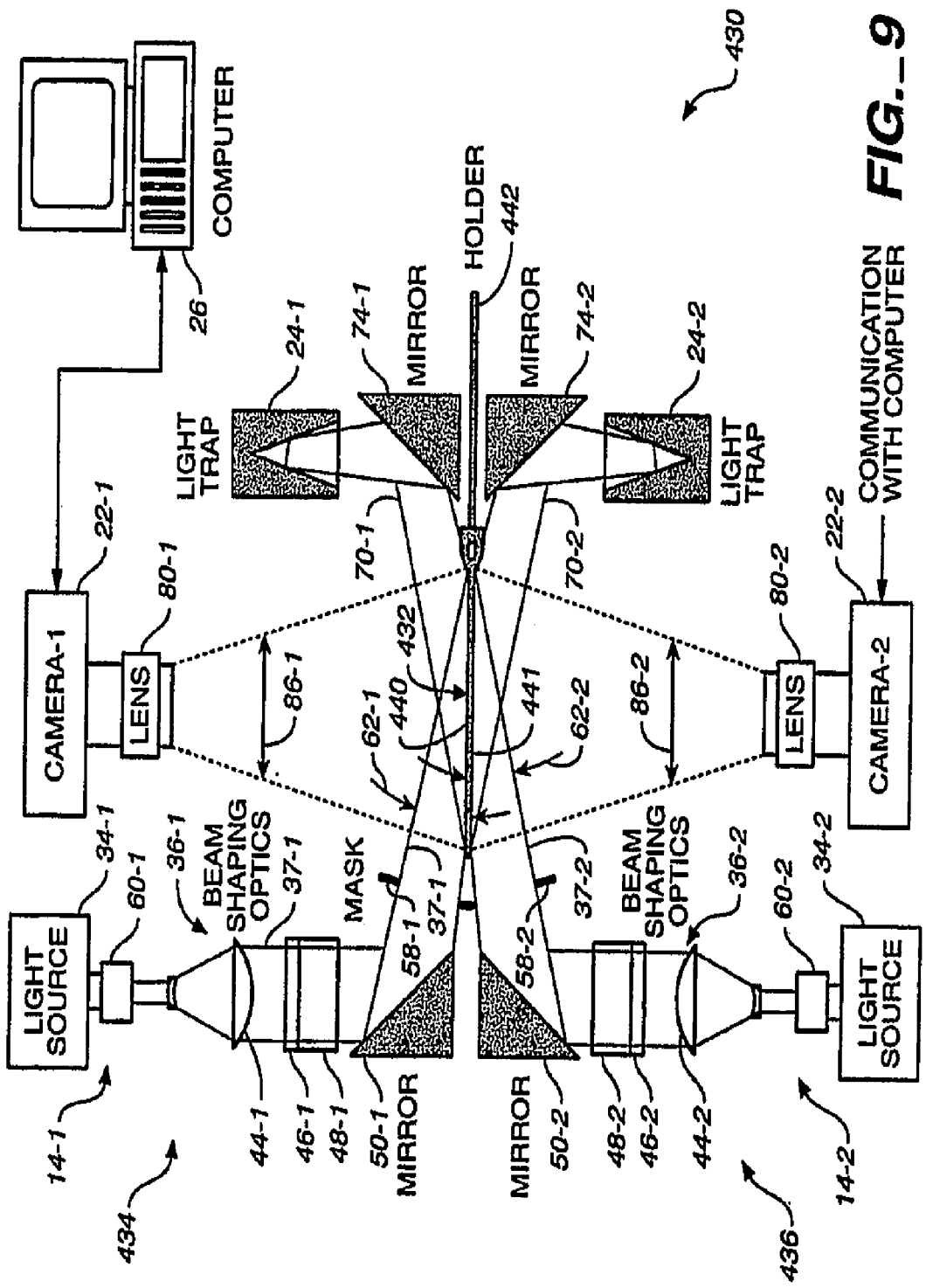
FIG._9

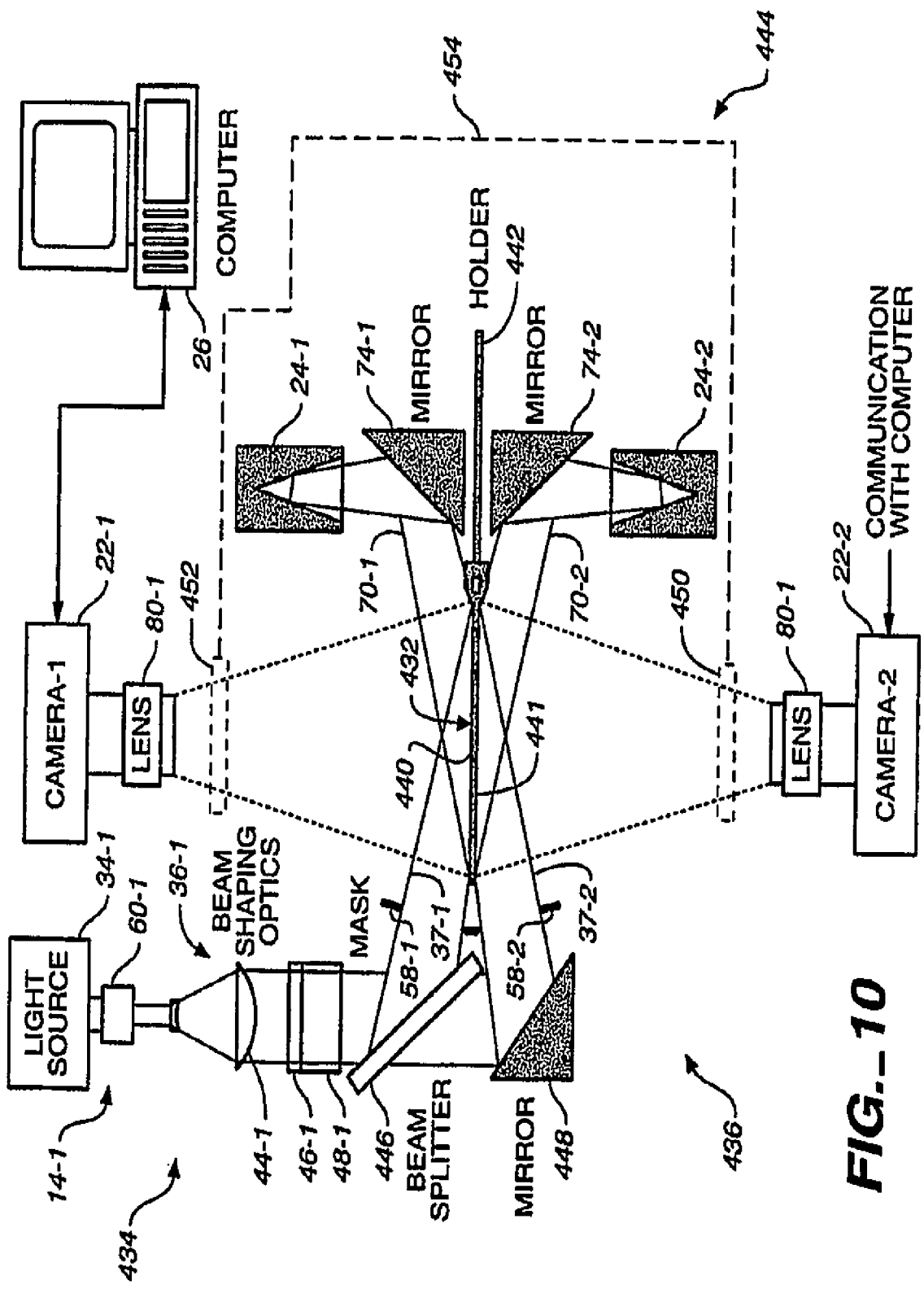
FIG._10

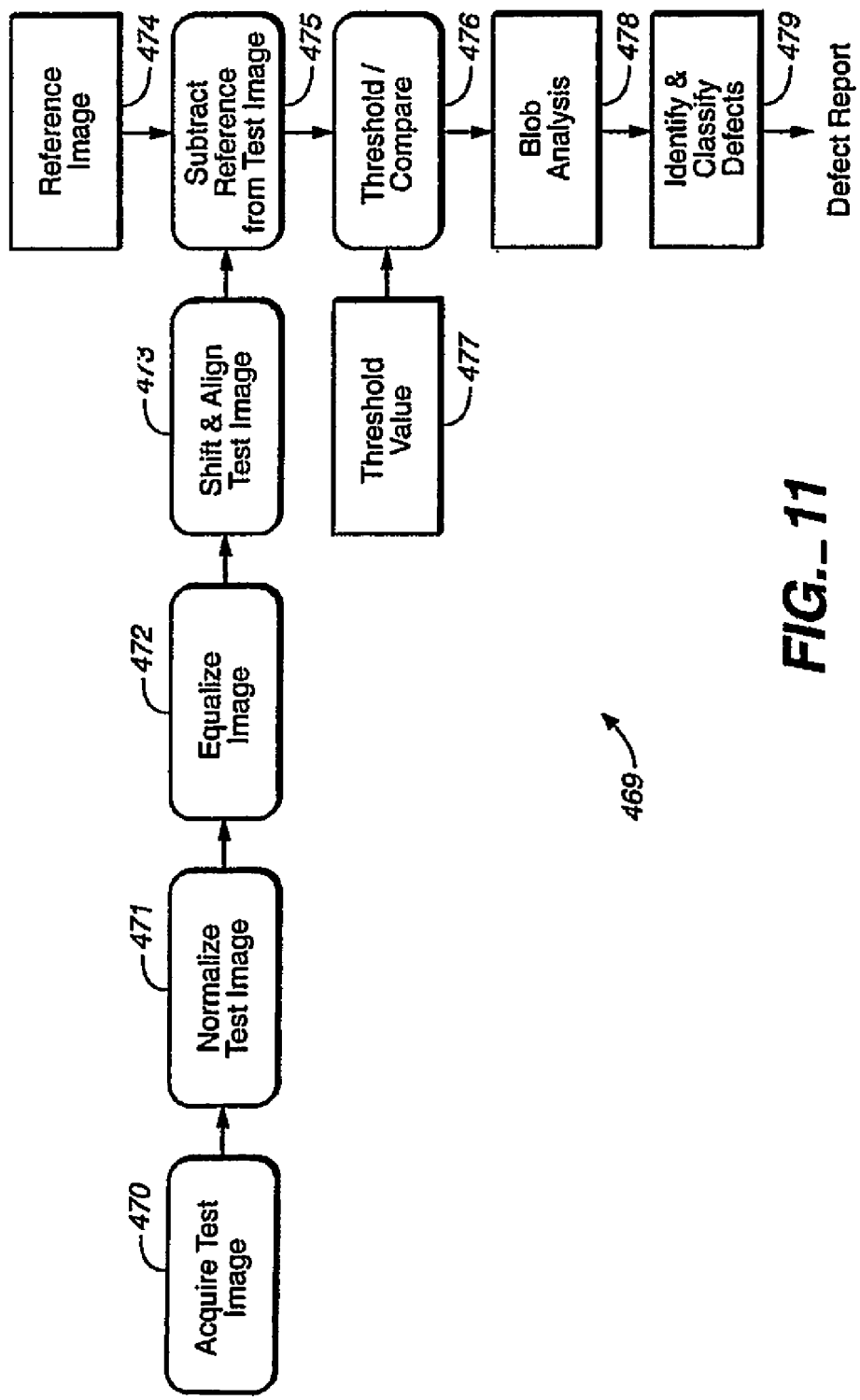
FIG._11

 FIG._12A
 FIG._12B
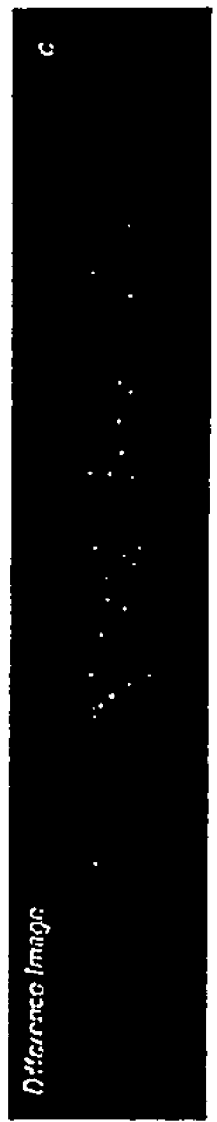 FIG._12C
 FIG._12D

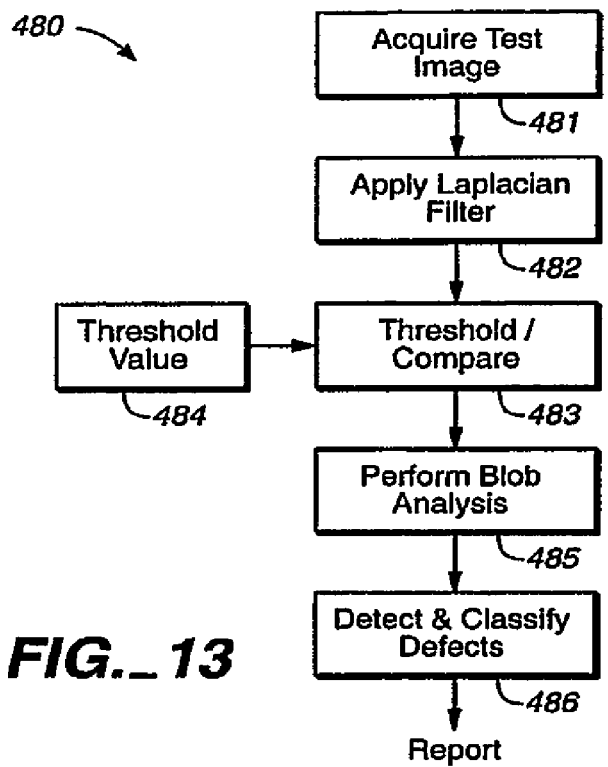
FIG._13
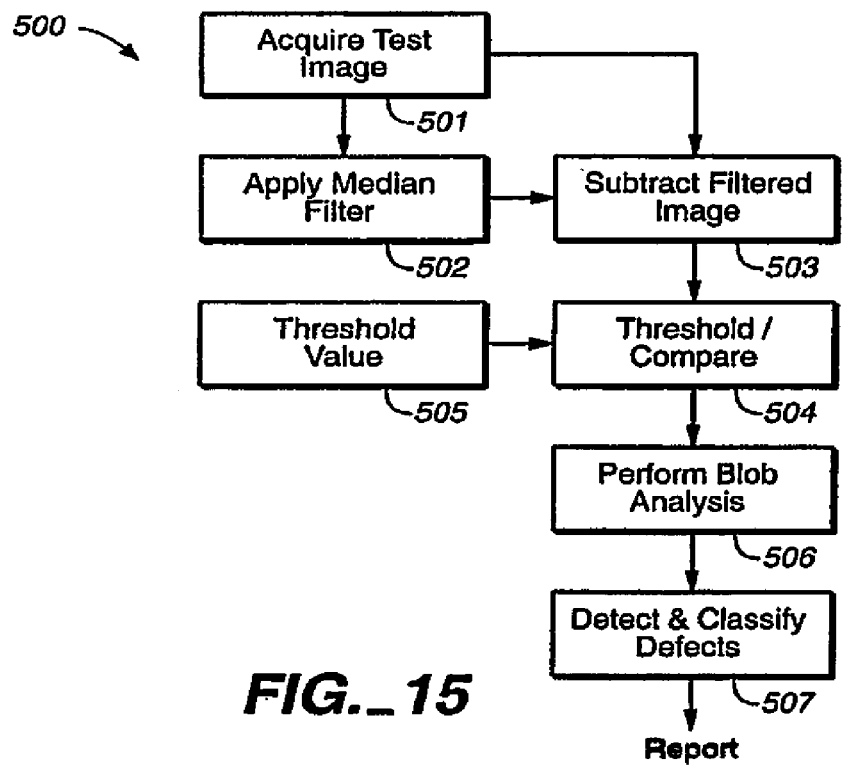
FIG._15

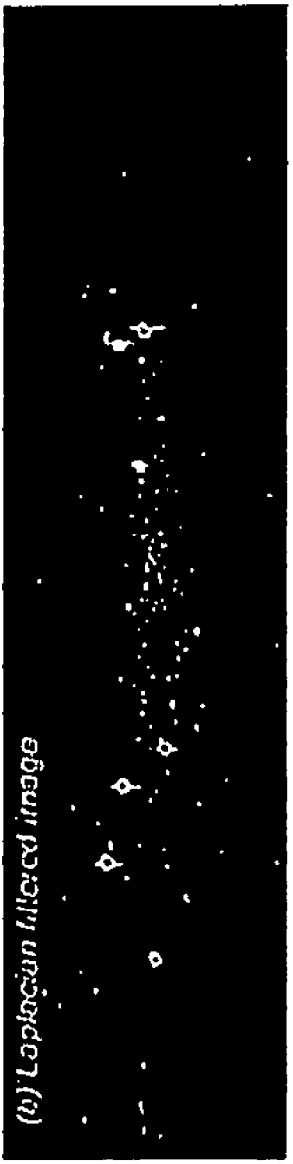
*FIG._14A*  *FIG._14B*  *FIG._14C*

   
FIG._16A  FIG._16B  FIG._16C  FIG._16D

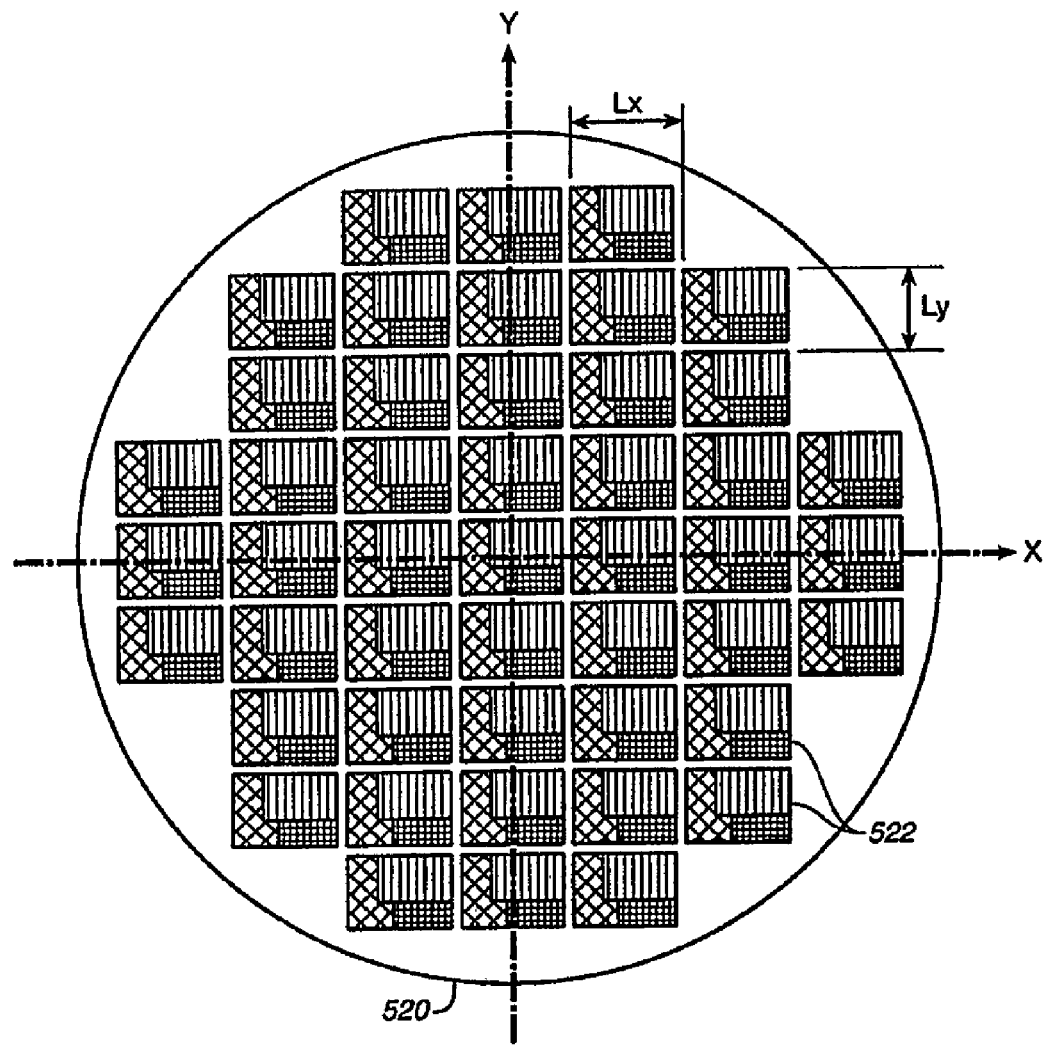
FIG._17

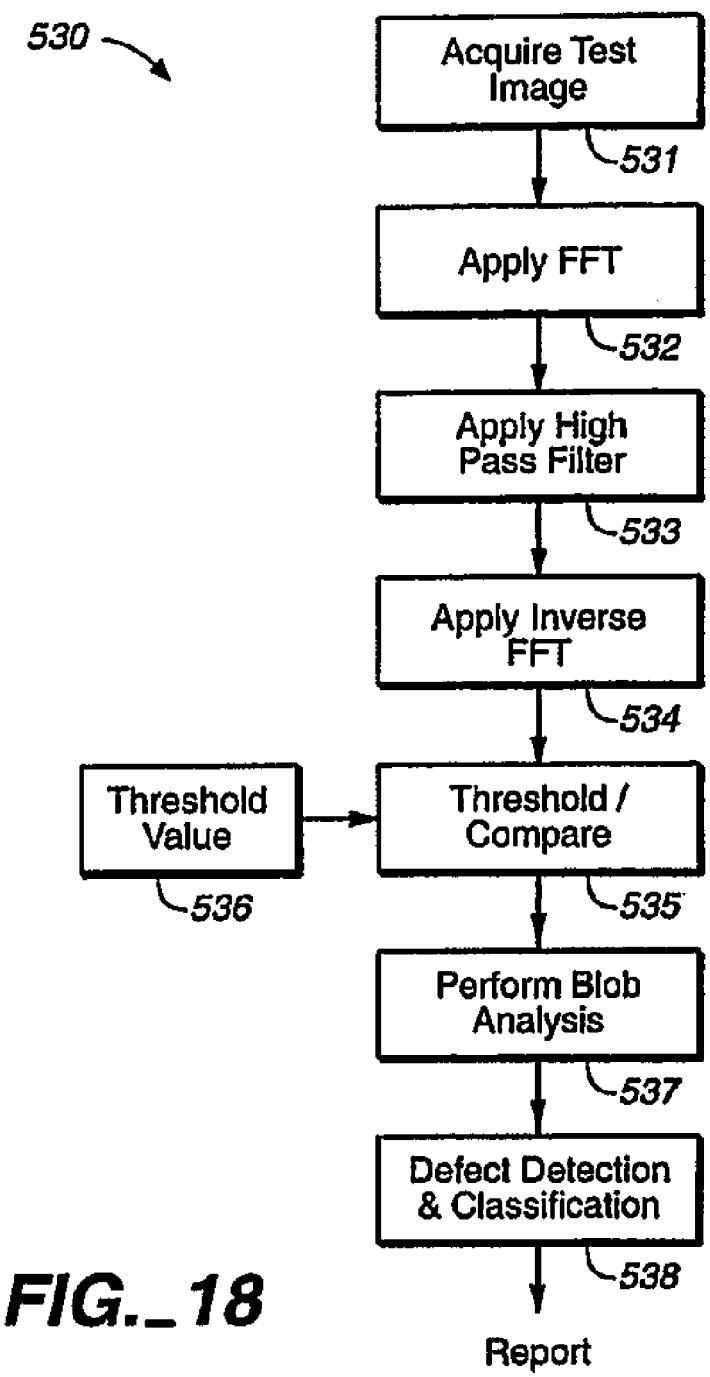
FIG._18

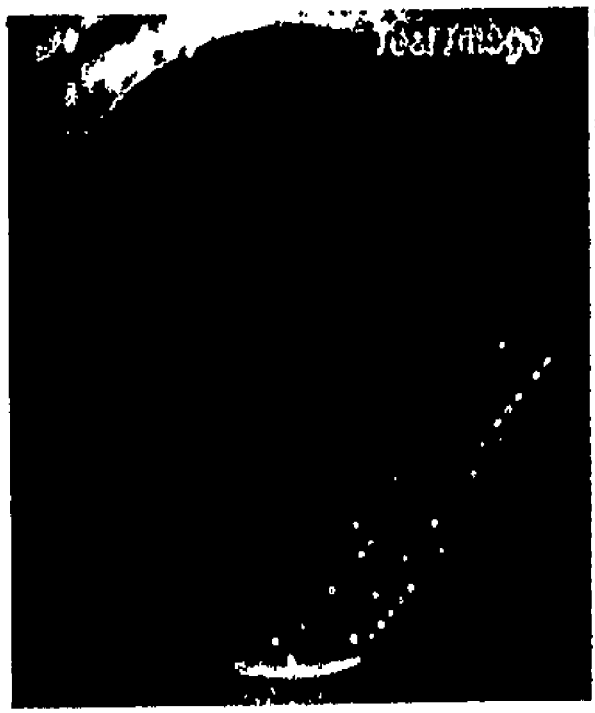 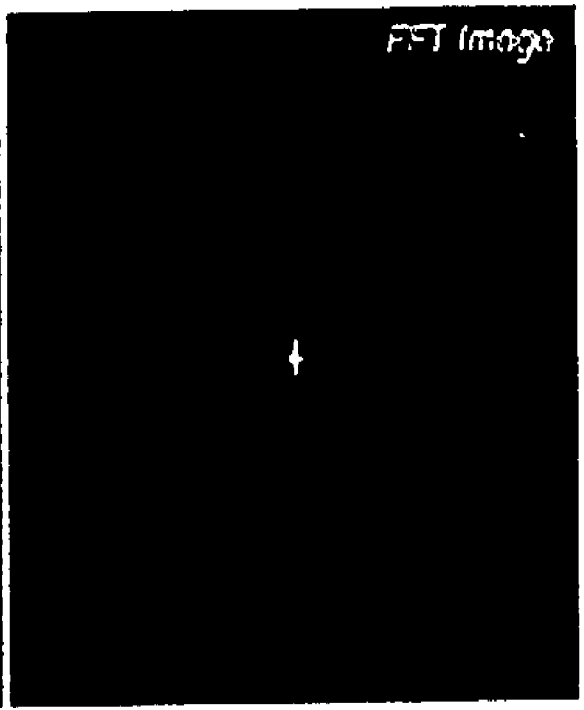
FIG._19A  FIG._19B

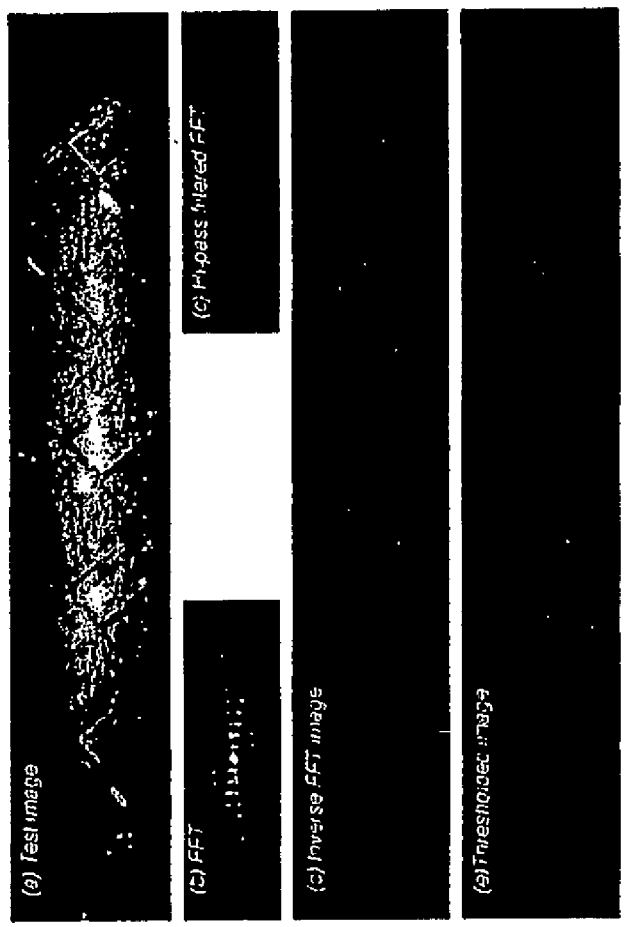
FIG._20A  FIG._20B  FIG._20C  FIG._20D  FIG._20E

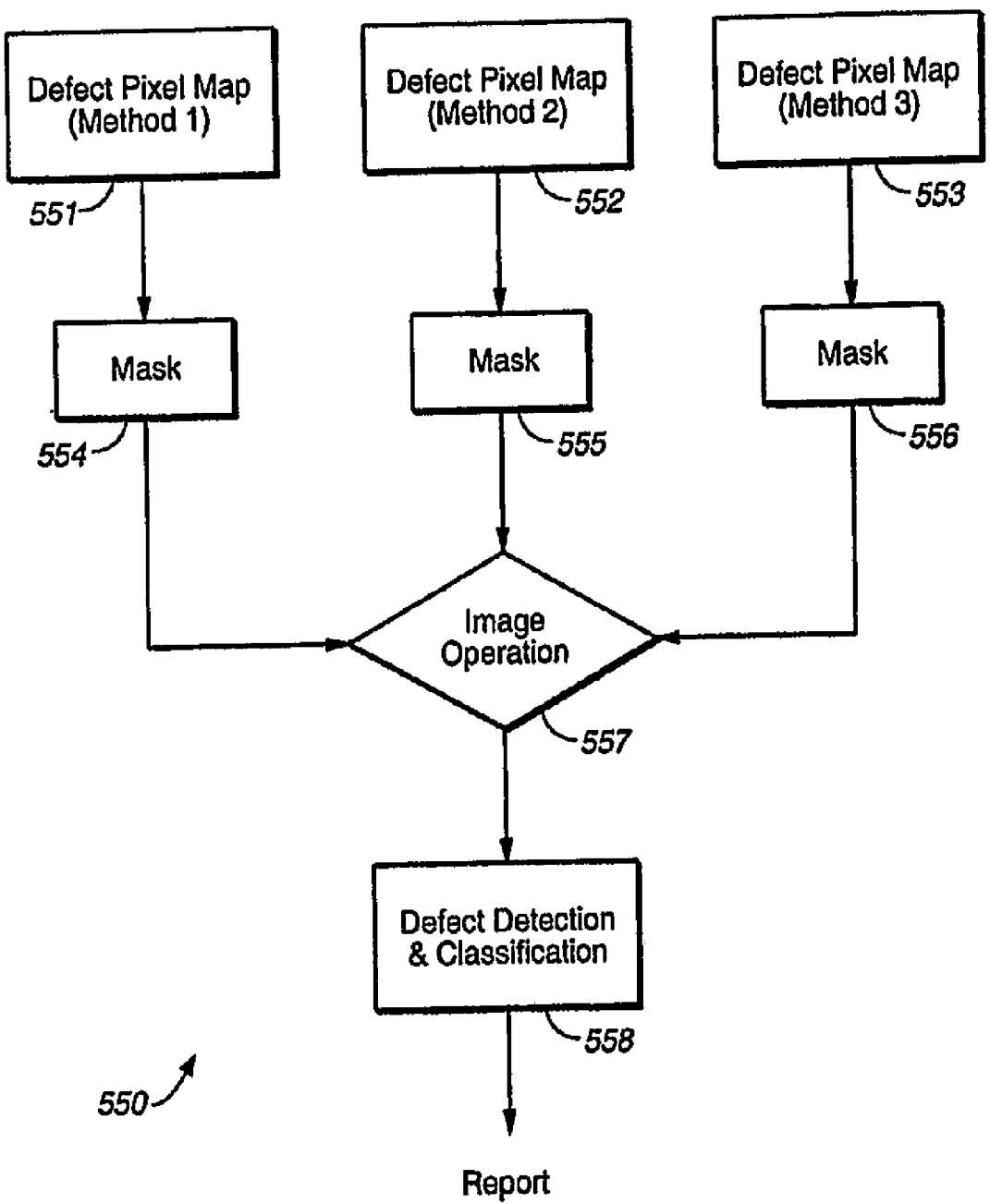
FIG._21

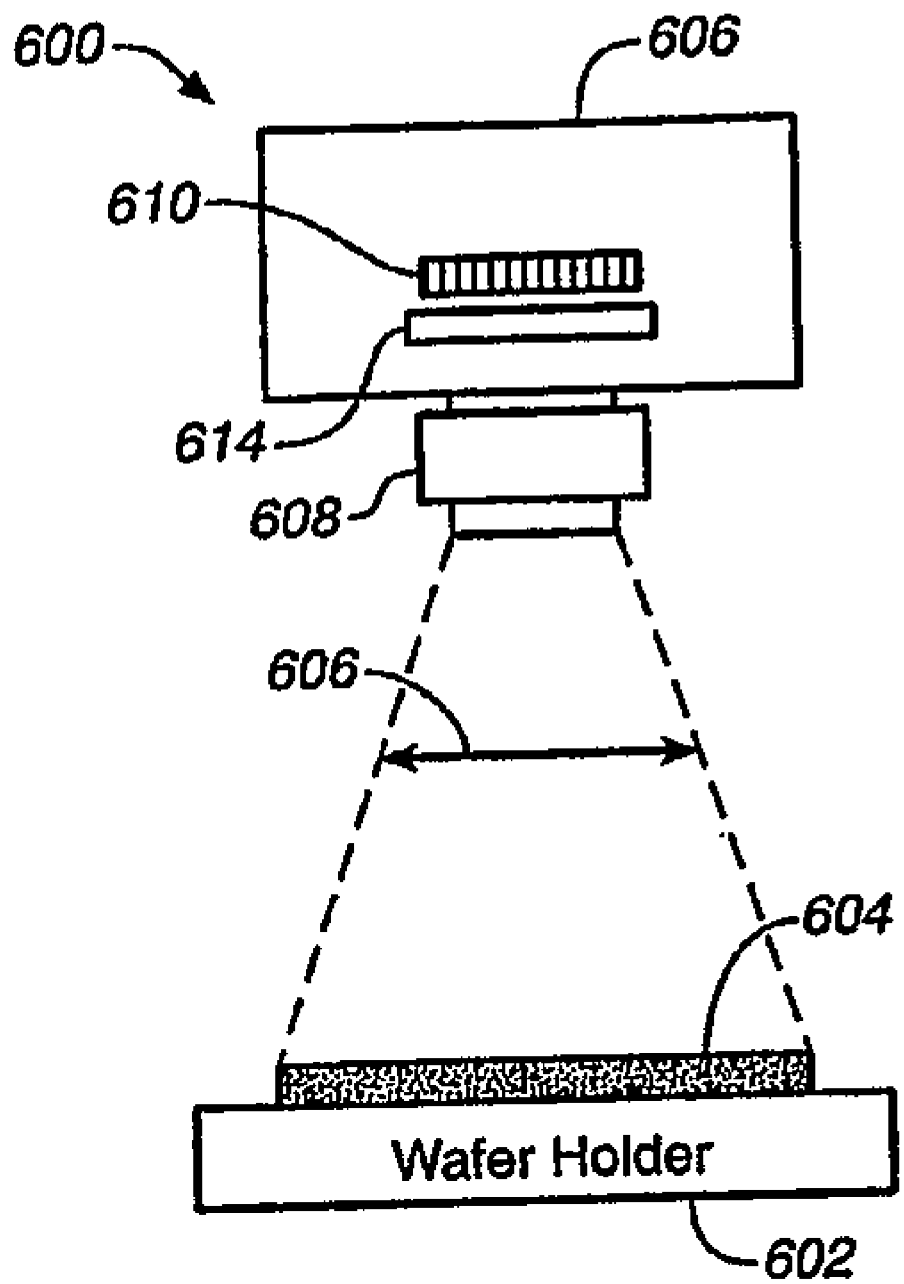
FIG._22